US010973953B1

(12) United States Patent
Semler et al.

(10) Patent No.: US 10,973,953 B1
(45) Date of Patent: Apr. 13, 2021

(54) METHODS AND COMPOSITIONS FOR PREPARING TRANSPLANT TISSUE

(71) Applicant: MUSCULOSKELETAL TRANSPLANT FOUNDATION, Edison, NJ (US)

(72) Inventors: Eric Semler, Morganville, NJ (US); Mark Spilker, Kilchberg (CH); Kevin Wu, Morganville, NJ (US); Yen-Chen Huang, East Brunswick, NJ (US); Evangelia Chnari, Scotch Plains, NJ (US); Jeffrey Cartmell, Freehold, NJ (US); Morris Jacobs, Newtown, PA (US); Alison Ling, Piscataway, NJ (US); Moon Hae Sunwoo, Old Tappan, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 15/680,012

(22) Filed: Aug. 17, 2017

Related U.S. Application Data

(60) Provisional application No. 62/376,843, filed on Aug. 18, 2016.

(51) Int. Cl.
| | |
|---|---|
| *A61L 27/38* | (2006.01) |
| *A01N 1/02* | (2006.01) |
| *A61L 27/36* | (2006.01) |
| *A61K 9/14* | (2006.01) |
| *A01N 1/00* | (2006.01) |
| *C12N 5/077* | (2010.01) |
| *C12N 5/073* | (2010.01) |
| *A61K 35/32* | (2015.01) |

(52) U.S. Cl.
CPC ........ *A61L 27/3895* (2013.01); *A01N 1/0284* (2013.01); *A61L 27/3604* (2013.01); *A61L 27/3683* (2013.01); *A61L 27/38* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,073,373 | A | 12/1991 | O'Leary et al. |
| 5,284,655 | A | 2/1994 | Bogdansky et al. |
| | | (Continued) | |

OTHER PUBLICATIONS

Huang, Hong; et al; "Deferoxamine Reduces Cold-Ischemic Renal Injury in a Syngeneic Kidney Transplant Model" American Journal of Transplantation, 3, 1531-1537, 2003 (Year: 2003).*

(Continued)

*Primary Examiner* — David W Berke-Schlessel
(74) *Attorney, Agent, or Firm* — Marcella M. Bodner; Cole Schotz, P.C.

(57) ABSTRACT

Methods and compositions for preparing and priming a tissue graft for an accelerated therapeutic effect are provided herein. In one embodiment, the method includes obtaining a tissue containing viable cells from a donor, wherein the viable cells are endogenous to the tissue and remain resident in the tissue; and priming the viable cells with one or more stimuli to produce a primed tissue, wherein when grafted to a recipient the primed tissue provides a benefit compared to non-primed tissue.

8 Claims, 30 Drawing Sheets
(30 of 30 Drawing Sheet(s) Filed in Color)

(56) References Cited

U.S. PATENT DOCUMENTS

| | | | |
|---|---|---|---|
| 5,484,601 A | 1/1996 | O'Leary et al. | |
| 7,052,856 B2 | 5/2006 | Ting | |
| 7,544,486 B2 | 6/2009 | Ting et al. | |
| 7,687,462 B2 | 3/2010 | Ting et al. | |
| 7,691,607 B2 | 4/2010 | Ting et al. | |
| 7,776,361 B2 | 8/2010 | Ting | |
| 7,807,787 B2 | 10/2010 | Ting et al. | |
| 7,833,968 B2 | 11/2010 | Soo et al. | |
| 7,884,066 B2 | 2/2011 | Ting | |
| 8,834,928 B1 | 9/2014 | Truncale et al. | |
| 8,883,210 B1 | 11/2014 | Truncale et al. | |
| 9,352,003 B1 | 5/2016 | Semler et al. | |
| 2008/0187518 A1 | 8/2008 | Ogle et al. | |
| 2009/0238801 A1 | 9/2009 | Woodbury et al. | |
| 2010/0274362 A1* | 10/2010 | Yayon | A61K 35/32 623/23.72 |
| 2012/0177615 A1 | 7/2012 | Cook et al. | |
| 2015/0010609 A1* | 1/2015 | Tom | A61K 35/50 424/423 |
| 2015/0307846 A1 | 10/2015 | Chen et al. | |
| 2017/0020927 A1 | 1/2017 | Ganey et al. | |
| 2018/0104282 A1 | 4/2018 | Sinclair | |

OTHER PUBLICATIONS

Menasche, Philippe; et al; "A promising approach for improving the recovery of heart transplants" Journal of Thoracic and Cardiovascular Surgery, 100, 13-21, 1990 (Year: 1990).*

Bartolome, Sonja; et al; "Deferoxamine Mimics the Pattern of Hypoxia-Related Injury at the Microvasculature" Shock, 31, 481-485, 2009 (Year: 2009).*

Cheng, H. et al., Osteogenic activity of the fourteen types of human bone morphogenetic proteins (BMPs), J. Bone & Joint Surgery, 2003, vol. 85, pp. 1544-1552.

Kinnaird et al., "Local delivery of marrow-derived stromal cells augments collateral perfusion through paracrine mechanisms", Circulation, 2004, vol. 109, pp. 1543-1549.

Pittenger M.F., et al., Science, "Multilineage potential of adult human mesenchymal stem cells", 1999, vol. 284, pp. 143-147.

Mariman E.C.M., et al., "Adipocyte extracellular matrix composition, dynamics and role in obesity", Cell. Mol. Life Sci., 2010, vol. 67, pp. 1277-1292.

Brown S.A., et. al., "Basic science review on adipose tissue for clinicians", Plast. Reconstr.Surg. 2010, vol. 126, pp. 1936-1946.

Gregoire F.M., et al., "Understanding adipocyte differentiation", Physiological Reviews,1998, vol. 78, pp. 783-809).

Truillo, M.E., et al. Adipose tissue-derived factors: impact on health and disease, Endocrine Reviews, 2006, vol. 27, pp. 762-778.

Kilroy G.E., et. al., "Cytokine profile of human adipose-derived stem cells: expression of angiogenic hematopoietic, and profinflammatory factors", Cellular Physiology,2007, vol. 212, pp. 702-709.

Peng et al., "Comparative analysis of mesenchymal stem cells from bone marrow, cartilage, and adipose tissue", Stem Cells and Development (2008), vol. 17, pp. 761-774, Mary Ann Liebert, Inc.

Karlsson C., et al., "Identification of a stem cell niche in the zone of ranvier within the knee joint", 2009, J. Anat., vol. 215, pp. 355-363, Anatomical Society of Great Britain and Ireland.

Murakami H., et al., "Quantitative differences in intervertebral disc-matrix composition with age-related degeneration", Med. Biol. Eng. Comput, 2010, vol. 8, pp. 469-474.

Smith L.J., et al., "Degeneration and regeneration of the intervertebral disc: lessons from development", 2011, Disease Models & Mechanisms, vol. 4, pp. 31-41.

Shamji M.D., et al. "Proinflammatory cytokine expression profile in degenerated and herniated human intervertebral disc tissues", Arthritis & Rheumatism, 2010, vol. 62, pp. 1974-1982.

Fong et al., "The crowning achievement: getting to the root of the problem", 2005, J. Dent. Educ., vol. 69, pp. 555-570.

Kurth T.B., et al., "Functional mesenchymal stem cell niches in adult mouse knee joint synovium in vivo", Arthritis & Rheumatism, 2011, vol. 63, pp. 1289-1300.

Bi Y., et al., "Identification of tendon stem/progenitor cells and the role of the extracellular matrix in their niche", Nature Medicine, 2007, Nat. Med., vol. 13, pp. 1219-1227.

Melero-Martin J.M., "Concise review: vascular stem cells and tumor angiogenesis", Stem Cells, 2011, vol. 29, pp. 163-168.

Mihu, C. M., et al., "Isolation and characterization of stem cells from the placenta and the umbilical cord", Romanian Journal of Morphology and Embryology, 2008, vol. 49, pp. 441-446.

Parolini, 0. et al., "Concise review: isolation and characterization of cells from human term placenta: outcome of the first international workshop on placenta derived stem cells", Stem Cell, 2008, vol. 26, pp. 300-311.

Miki T., et al.,"Stem cell characteristics of amniotic epithelial cells", Stem Cells, 2005, vol. 23, pp. 1549-1559.

Miki, T., et al., "Amnion-derived plutipotent/multipotent stem cells", Stem Cells, 2006, vol. 2, pp. 133-142, Humana Press, Inc.

Casey, M.L., "Interstitial collagen synthesis and processing in human amnion: a property of the mesenchymal cells", Biology of Reproduction, 1996, vol. 55, pp. 1253-1260.

Soncini, M. et al., "Isolation and characterization of mesenchymal cells from human fetal membranes", Journal of Tissue Engineering and Regenerative Medicine, 2007, vol. 1, pp. 296-305.

Wei J. et al., "Human amnion-isolated cells normalize blood glucose in streptozocin-induced diabetic mice", Cell Transplantation, 2003, vol. 2, pp. 545-552, Cognization Comm. Corp.

Alviano, F., et al, "Term amniotic membrane is a high throughput source for multipotent mesenchymal stem cells with the ability to differentiate into endothelial cells in vitro", BMC Dev Biol, 2007, vol. 7, pp. 1-14.

Zhao, P. et al, "Human amniotic mesenchymal cells have some characterisitics of cardiomyocytes", Transplantation, 2005, vol. 79, pp. 528-535.

Portman-Lanz, C.B. et al, "Placental mesenchymal stem cells as potential autologous graft for pre-and perinatal neuroregeneration", American Journal of Obstetrics and Gynecology, 2006, vol. 194, pp. 664-673.

Munn, D. et al., "Inhibition of T cell proliferation by macrophage tryptophan catabolism" J Exp Med, 1999, vol. 189, pp. 1363-1372.

Sandjieu Y., et al., "Desmosealin and other components of the epidermal extracellular matrix", 2009, J. Physiol. Pharmacal., vol. 60, pp. 23-30.

Hodde J.P., et al., "Extracellular matrix as a strategy for treating chronic wounds", Am. J. Clin. Dermatol., 2007, vol. 8, 61-66.

Blanpain C., et al., "Epidermal homeostasis: a balancing act of stem cells in the skin", Nat. Rev. Mol. Cell. Biol, 2009, vol. 10, pp. 207-217.

Gopinath et al., "Stem cell review series: aging of the skeletal muscle stem cell niche", Aging Cell, 2008,vol. 7, pp. 590-598.

Holmberg et al., "Activation of neural and pluripont stem cell signatures correlates with increased malignancy in human glioma", PLoS One., 2011, 6(3): e18454.

Hombach-Klonisch S., et al., "Adult stem cells and their trans-differentiation potential perspectives and therapeutic applications", J. Mol. Med., 2008, vol. 86, pp. 1301-1314.

Zouboulis C.C., et al., "Human skin stem cells and the ageing process", Experimental Gerontology, 2008, vol. 43, pp. 986-997, Elsevier Publishing.

Alvarez-Buylla A., et al., "For the long run: maintaining germinal niches in the adult brain", Neuron, 2004, vol. 41, pp. 683-686.

Hirshci K.K., et al., "Smooth muscle stem cells", The Anatomical Record, 2004, vol. 276, pp. 22-33.

Majumdar et al., Phenotypic and functional comparison of cultures of marrow-derived mesenchymal stem cells (MSCs) and stromal cells, J. Cell Physiol. 176: 57-66 (1998).

Baksh et al., "Adult mesenchymal stem cells: characterization differentiation, and application in cell and gene therapy", J. Cell. Mol. Med. 2004, 8(3) 301-16, 305.

Lee et al., "Mesenchymal progenitor cells derived from synovium and infrapatellar fat pad as a source for superficial zone cartilage

(56) References Cited

OTHER PUBLICATIONS tissue engineering: Analysis of superficial zone protein/lubricin expression", Tissue Engg. 2010, 16(1): 317-325.

Wilson et. al., "Proteomic analysis of cartilage proteins". 2008, Methods, 48: 22-31.

Gaissmaier et al., "Growth and differentiation factors for cartilage healing and repair", 2008, Int. J. Care Injured, 39SI: S88-S96.

Asalameh et al.,"Identification of mesenchymal progenitor cells in normal and osteoarthritic human articular cartilage", Arthritis & Rheumatism, 2004, 50(5): 1522-1532.

Hiraoka et al., "Mesenchymal progenitor cells in adult human articular cartilage", Biorheology, 2006, 43: 447-454.

Grogan et al.,"Mesenchumal progenitor cell markers in human articular cartilage: normal distribution and changes in osteoarthritis", Arthritis Res. Ther. 2009, 11(3): R85-R97.

Feng et al., "Extracellular matrix in degeneration", 2006, J. Bone Joint Surg. Am. 88: 25-29.

Hsieh A.H., et al., "Cellular mechanobiology of the intervertebral disc: New directions and approaches", Biomech., 2010, 43(1): 137-156.

Henriksson et al.,"Identification of cell proliferation zones, progenitor cells and a potential stem cell niche in the intervertebral disc region", 2009, Spine, 34(21): 2278-2287.

Ulmer et al., 2010, "Stem Cells—Prospects in Dentistry", Schweiz Monatsschr Zahnmed, 120:860-872.

Cheng et al., "Comparison of potentials between stem cells isolated from human anterior cruciate ligament and bone marrow for ligament tissue engineering", 2010, Tissue Engg. A, 16(7):2237-2253.

Koga et al., "Comparison of mesenchymal tissues-derived stem cells for in vivo chondrogenesis: suitable conditions for cell therapy of cartilage defects in rabbit" 2008, Cell Tissue Res., 333: 207-215.

Miyamoto et al., 2010, "Intradiscal transplantation of synovial mesenchymal stem cells prevents intervertebral disc degeneration through suppression of matrix metalloproteinase-related genes in nucleus pulposous cells in rabbits", Arthritis Res. Ther., 12: R206-218.

Tilki et al.,"Emerging biology of vascular wall progenitor cells in health and disease", 2009, Trends Mol. Med. 15(11): 501-509.

Non-Final Office Action for U.S. Appl. No. 16/292,584, dated Feb. 21, 2020.

Benirschke, K. and Kaufmann, P. Pathology of the human placenta. New York, Springer-Verlag, 2000, 42-46, 116, 281-297.

Zhang, X., et al., "Mesenchymal progenitor cells derived from chorionic villi of +human placenta for cartilage tissue engineering", Biochem Biophys Res Commun, 2006, 340: 944-952.

Zhang et al.,"Successful immortalization of mesenchymal progenitor cells derived from human placenta and the differentiation abilities of immortalized cells", Biochem Biophys Res Commun, 2006, 351: 853-859.

Wolbank, S. et al., "Dose-dependent immunomodulatory effect of human stem cells from amniotic membrane: A comparison with human mesenchymal stem cells from adipose tissue", Tissue Eng, 2007, 13: 1173-1183.

Int' Anker, P. et al., "The difference of breakthrough moments", Stem Cells, 2004, 22: 1338-1345.

Munn, D. et al., "Prevention of allogenic fetal rejection by tryptophan catabolism", Science, 1998, 281: 1191-1193.

Baban, B. et al., "Indoleamine 2,3-dioxygenase expression is restricted to fetal trophoblast giant cells during murine gestation and is maternal genome specific", J Reprod Immunol, 2004, 61: 67-77.

Wu et al., "Muscle-derived stem cells: isolation, characterization, differentiation, and application in cell and gene therapy", 2010, Cell Tissue Res 340: 549-567.

Mazhari, et al., "Mechanisms of action of mesenchymal stem cells in cardiac repair: potential influences on the cardiac stem cell niche",, 2007, Nat. Clin. Pract. Cardiovasc. Med., 4(S1): S21-S26.

Yun ey al., "Transcriptional regulatory networks associated with self-renewal and differentiation of neural stem cells", 2010, J. Cell. Physiol. 225: 337-347.

Issekutz et al.,"Differential roles of VLA-4(CD49d/CD29) and LFA-1(CD11a/CD18) integrins and E- and P-selectin during developing and established active or adoptively transferred adjuvant arthritis in the rat", Immunol Cell Biol. Oct. 2003; 8I(S):397-408.

Bailo M., et al., "Engraftment potential of human amnion and chorion cells derived from term placenta", Transplantation, 2004, vol. 78, pp. 1439-1448, Lippincott & Williams.

Blanpain C., "Skin regeneration and repair", Nature, 2010, vol. 464, pp. 686-687, Macmilan Publishers.

Kajstura J., et al., "Evidence for human lung stem cells", The New England Journal of Medicine, 2011, vol. 364, pp. 1795-1806.

Labarge M.A., et al., "Of microenvironments and mammary stem cells", Stem Cell Review, 2007, vol. 3, pp. 137-146, National Institute of Health.

Pacilli A., et al., "Vascular wall resident progenitor cells: A review", Experimental Cell Research, 2009, vol. 315, pp. 901-914, Elsevier.

Shoulders M.D., et al., "Collagen structure and stability", Annu. Rev. Biochem., 2009, vol. 78, pp. 929-958, National Institute of Health.

Zhang X. et al., "Periosteal stem cells are essential for bone revitalization and repair", J. Musculoskelet Neuronal Interact, 2005, vol. 5, pp. 360-362, Hylonome.

Brochhausen C. et al., "Signaling molecules and growth factors for tissue engineering of cartilage—what can we learn from the growth plate", (J. Tissue Eng. Regen. Med. 2009, 3: 416-429).

\* cited by examiner

| H&E | Donor No. 1 | Donor No. 2 |
|---|---|---|
| 2 week osteo | | |
| 4 week (7771108803) / 3 week (7771108753) osteo | | |
| 6 week osteo | | |
| 6 week control | | |

FIG. 2C

| Amnion-Alizarin Red | Osteogenic Media | Growth Media |
|---|---|---|
| 4 week |  |  |
| 6 week |  |  |
| 8 week |  |  |

| Amnion-Von Kossa | Osteogenic Media | Growth Media |
|---|---|---|
| 4 week |   |  |
| 6 week |   |  |
| 8 week |   |  |

| Amnion-H&E | Osteogenic Media | Growth Media |
|---|---|---|
| 4 week | | |
| 6 week | | |
| 8 week | | |

FIG. 3C

| Amnion-Alizarin Red | Osteogenic Media | Growth Media |
|---|---|---|
| 2 week |  |  |
| 4 week |  |  |
| 6 week |  |  |

| Amnion-Von Kossa | Osteogenic Media | Growth Media |
|---|---|---|
| 2 week |  |  |
| 4 week |  |  |
| 6 week |  |  |

| Amnion - H&E | Osteogenic Media | | Growth Media |
|---|---|---|---|
| 2 week |  |  |  |
| 4 week |  |  |  |
| 6 week |  |  |  |

| Chorion-Alizarin Red | Osteogenic Media | Growth Media |
|---|---|---|
| 2 week |   |  |
| 4 week |   |  |
| 6 week |   |  |

| Chorion-Von Kossa | Osteogenic Media | Growth Media |
|---|---|---|
| 2 week | | |
| 4 week | | |
| 6 week | | |

FIG. 4E

| Chorion-H&E | Osteogenic Media | Growth Media |
|---|---|---|
| 2 week |  |  |
| 4 week |  |  |
| 6 week |  |  |

| Amnion-Von Kossa | Osteogenic Media | Growth Media |
|---|---|---|
| 4 week |  |  |

| Amnion-H&E | Osteogenic Media | Growth Media |
|---|---|---|
| 4 week |  |  |

METHODS AND COMPOSITIONS FOR PREPARING TRANSPLANT TISSUE

CROSS REFERENCE TO RELATED APPLICATION

The present application claims the benefit of U.S. Provisional Application No. 62/376,843, filed Aug. 18, 2016, the entire disclosure of which is incorporated by reference herein.

FIELD

Compositions and methods disclosed herein relate to transplant tissue, in particular preparation of enhanced transplant tissue prior to clinical usage.

BACKGROUND

Transplantation of isolated tissue or whole organs is a critical therapeutic strategy that is widely utilized in the treatment of patients. Tissue transplants can be in the form of an allograft, autograft, or xenograft. An allograft transplant is the transplantation of cells, tissues, or organs to a recipient from a genetically non-identical recipient of the same species. An autograft is the transplantation of tissue from one site to another on located on the same patient. A xenograft is the transplantation of tissue from another species. In each case the tissue is removed from a donor, handled, and transplanted to a recipient to regenerate tissue.

Known methods and procedures for tissue and organ transplantation have significant limitations. For example, the handling and processing of transplant tissue may result in inflammation, a decreased biologic response upon transplantation, or morbidity of patients. Further, even tissues from a genetically similar donor, may contain cells that are not immunologically compatible or reactive with the recipient.

Therefore, methods and compositions for providing improved transplant tissue are urgently needed.

SUMMARY

In one aspect, a method for preparing a primed tissue graft is provided. The method can include obtaining a tissue containing viable cells from a donor, wherein the viable cells are endogenous to the tissue and remain resident in the tissue; and priming the viable cells with one or more stimuli to produce a primed tissue graft, wherein when used to treat a patient the primed tissue graft provides a benefit compared to non-primed tissue.

In various embodiments, the tissue is an allograft, autograft or xenograft tissue. The tissue can be obtained from any source, such as one or more of placenta, amnion, chorion, umbilical cord, Wharton's Jelly, bone, periosteum, cartilage, meniscus, spinal disc, muscle, tendon, ligament, adipose, skin, cardiovascular tissue, peritoneum, fascia, interstitial tissue such as intestinal submucosa, nerve, cornea, visceral organ, reproductive tissue, hair follicles, foreskin, and dental tissue.

In some embodiments, the viable cells are not isolated from the tissue and comprise non-terminally differentiated cells and/or differentiated cells.

In certain embodiments, the one or more stimuli can be a transient or prolonged exposure to one or more biochemical agents, deprivation of nutrient(s), change in oxygen level, application of mechanical stress and/or electromagnetic field, change in temperature, change in pH, irradiation, shockwave treatment, pressure level, or any combination of the foregoing.

In some embodiments, the biochemical agent can be one or more of a growth-inductive component, medium component, cell death inhibitor, antioxidant, vitamin, enzyme, expression of antimicrobial, anti-inflammatory, anti-scarring, or angiogenic proteins, and differentiation-inducing factor such as dexamethasone and indomethacine. The change in oxygen level can be hypoxia or hyperoxia due to atmospheric oxygen levels and/or exposure to a medium ingredient that simulates hypoxia or hyperoxia such as deferoxamine. The mechanical stress can be one or more of fluid flow, shear, stretch, compression, torque, static force, cyclic force and pulsatile force.

In various embodiments, the benefit provided by the primed tissue graft comprises one or more of (1) altered cell adhesion, altered cell proliferation, altered cell survival, maintenance of cell viability, maintenance of cell phenotype and/or altered cell migration; (2) induced cell differentiation, de-differentiation and/or transdifferentiation; (3) production of extracellular matrix and/or biochemical factors; (4) faster or improved healing or remodeling; (5) reduced risk of infection; (6) reduced risk of graft rejection; and (7) reduced level of inflammation.

In some embodiments, the method can further include cryopreserving the primed tissue graft and grafting the cryopreserved tissue. Alternatively, primed tissue graft can be grafted to a recipient without cryopreservation.

In some embodiments, the method can further include storage of the primed tissue graft at frozen temperatures, at refrigerated temperatures, or at above refrigerated temperatures.

In some embodiments, the method can further include maintaining the integrity of the primed tissue graft.

In some embodiments, the method can further include preparing the primed tissue graft and optionally the viable cells resident in the primed tissue graft for the environment into which the primed tissue graft will be implanted into.

In some embodiments, the method can further include grafting the primed tissue graft to the patient, wherein at the time of grafting, the primed tissue graft contains the viable cells.

In certain embodiments, immunoreactive cells can be removed prior to grafting. The primed tissue graft can also be devitalized or decellularized prior to grafting. Devitalizing can include physical treatment (e.g., freeze-and-thaw cycles, sonication, pressure, vacuum, and mechanical agitation), enzymatic treatment (e.g., Trypsin) and/or chemical treatment (e.g., sodium deoxycholate, Triton X solutions).

Another aspect relates to an artificially primed tissue graft, comprising: a tissue obtained from a donor; and viable cells that are endogenous to the tissue and remain resident in the tissue, wherein the viable cells have been primed with one or more stimuli to produce a primed tissue graft, wherein when used to treat a patient the primed tissue provides a benefit compared to non-primed tissue.

A further aspect relates to an artificially primed tissue graft, comprising: a tissue obtained from a donor; and extracellular components produced by viable cells that are endogenous to and resident in the tissue, wherein the viable cells have been primed with one or more stimuli to produce the extracellular components and subsequently at least partially devitalized or decellularized, wherein the extracellular components comprise extracellular matrix and/or secreted factors and are associated with the primed tissue graft;

wherein when used to treat a patient the primed tissue graft provides a benefit compared to non-primed tissue.

Yet another aspect relates to an artificially conditioned medium, comprising: a base medium for priming viable cells that are endogenous to and resident in a tissue obtained from a donor; and one or more factors secreted by the viable cells during priming, wherein when grafted or administered to a recipient the conditioned medium provides a benefit.

In some embodiments, the artificially conditioned medium can further include a component for extending cell viability.

In some embodiments, the artificially conditioned medium can further include a component for pre-conditioning tissue grafts and cells endogenous to the tissue grafts.

In a further aspect, a method for providing a primed tissue graft is provided. The method can include obtaining a tissue containing viable cells from a donor, wherein the viable cells are endogenous to the tissue and remain resident in the tissue; and priming the tissue graft with one or more stimuli to produce a primed tissue graft, wherein when used to treat a patient, the primed tissue graft provides a benefit compared to non-primed tissue.

In various embodiments, the tissue is an allograft, autograft or xenograft tissue. The tissue can be obtained from any source, such as one or more of placenta, amnion, chorion, umbilical cord, Wharton's Jelly, bone, periosteum, cartilage, meniscus, spinal disc, muscle, tendon, ligament, adipose, skin, cardiovascular tissue, peritoneum, fascia, interstitial tissue such as intestinal submucosa, nerve, cornea, visceral organ, reproductive tissue, hair follicles, foreskin, and dental tissue.

In certain embodiments, the one or more stimuli can be a transient or prolonged exposure to one or more biochemical agents, deprivation of nutrient(s), change in oxygen level, application of mechanical stress and/or electromagnetic field, change in temperature, change in pH, irradiation, shockwave treatment, pressure level, or any combination of the foregoing.

In various embodiments, the benefit provided by the primed tissue graft comprises one or more of (1) altered cell adhesion, altered cell proliferation, altered cell survival, maintenance of cell viability, maintenance of cell phenotype and/or altered cell migration; (2) induced cell differentiation, de-differentiation and/or transdifferentiation; (3) production of extracellular matrix and/or biochemical factors; (4) faster or improved healing or remodeling; (5) reduced risk of infection; (6) reduced risk of graft rejection; and (7) reduced level of inflammation.

In some embodiments, the method can further include grafting the primed tissue graft to the patient, wherein at the time of grafting, the primed tissue graft contains the viable cells.

Also provided herein is a composition comprising the artificially primed tissue graft disclosed herein and the artificially conditioned medium disclosed herein.

Another aspect relates to a method for providing a primed tissue graft, comprising: obtaining a tissue containing viable cells from a donor, wherein the viable cells are endogenous to the tissue and remain resident in the tissue; and priming the viable cells with one or more stimuli to increase cell viability. In some embodiments, the one or more stimuli include a cell death or apoptosis inhibitor.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 2A-2C illustrate osteogenic differentiation of cryopreserved amnion tissue;

FIGS. 3A-3F illustrate osteogenic differentiation of fresh minced amnion and chorion tissue;

FIGS. 4A-4F illustrate osteogenic differentiation experiments of cryopreserved minced amnion and chorion tissue;

DETAILED DESCRIPTION

Figure 1A:
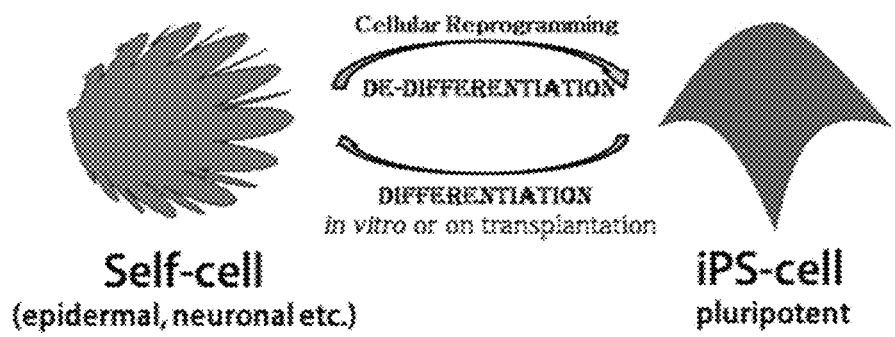
FIGS. 1A-1B illustrate a simplified schematic of cellular reprograming.

The compositions and method disclosed herein relate to priming of tissues and cells before grafting, and primed tissue, primed cells and conditioned media prepared therefrom. In some embodiments, a method for providing a primed tissue can include: obtaining a tissue containing viable cells from a donor, wherein the viable cells are endogenous to the tissue and remain resident in the tissue; and priming the viable cells with one or more stimuli to produce a primed tissue, wherein when grafted to a recipient the primed tissue provides a benefit compared to non-primed tissue. The benefit can include one or more of (1) altered cell adhesion, altered cell proliferation, altered cell survival, maintenance of cell viability, maintenance of cell phenotype and/or altered cell migration; (2) induced cell differentiation, de-differentiation and/or transdifferentiation; (3) production of extracellular matrix and/or biochemical factors; (4) faster or improved healing or remodeling; (5) reduced risk of infection; (6) reduced risk of graft rejection; and (7) reduced level of inflammation. In various embodiments, the viable cells are not isolated from the tissue and comprise non-terminally differentiated cells and/or differentiated cells.

The tissue can be an allograft, autograft or xenograft tissue. In some embodiments, the tissue is obtained from one or more of placenta, amnion, chorion, umbilical cord, Wharton's Jelly, bone, periosteum, cartilage, meniscus, spinal disc, muscle, tendon, ligament, adipose, skin, cardiovascular tissue, peritoneum, fascia, nerve, cornea, visceral organ, reproductive tissue, hair follicles, foreskin, and dental tissue. In some embodiments, the tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascial tissue, a gastrointestinal tissue, a growth plate tissue, an intervertebral disc tissue, an intestinal mucosal tissue, an intestinal serosal tissue, a ligament tissue, a liver tissue, a lung tissue, a mammary tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, and any combination thereof.

In certain embodiments, the one or more stimuli can be a biochemical agent, deprivation of nutrient(s), change in oxygen level, mechanical stress, electromagnetic field, change in temperature, change in pH, irradiation, shockwave treatment, pressure level, or any combination of the foregoing.

1. Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

The articles "a" and "an" are used herein to refer to one or to more than one (i.e., at least one) of the grammatical object of the article. By way of example, "an element" means one element or more than one element.

As used herein, the term "about" means within 20%, more preferably within 10% and most preferably within 5%. The term "substantially" means more than 50%, preferably more than 80%, and most preferably more than 90% or 95%.

The term "adipokine" as used herein refers to a factor secreted by adipose tissue.

The term "adipocyte" as used herein refers to the functional cell type of fat, or adipose tissue that is found throughout the body, particularly under the skin. Adipocytes store and synthesize fat for energy, thermal regulation and cushioning against mechanical shock. Although the lineage of adipocytes is still unclear, it appears that MSCs can differentiate into two types of lipoblasts, one that give rise to white adipocytes and the other to brown adipocytes. Both types of adipocytes store fat.

The term "adipogenic" as used herein refers to a potential of precursor cells to differentiate into fat forming or adipocompetent cells, wherein the adipogenic cells include one or more of an adipogenic stem cell, a tissuegenic cell, a precursor cell, a progenitor cell, an immature cell, a non-terminally differentiated cell, a cell with differentiation potential, or a combination thereof.

The term "adipose stem cell" (ASC) as used herein refers to pluripotent stem cells, MSCs and more committed adipose progenitors and stroma obtained from adipose tissue.

As used herein, the term "allograft" refers to a graft of tissue obtained from a donor of the same species as, but with a different genetic make-up from, the recipient, as a tissue transplant between two humans. The term allograft is generally referred to as an implant.

The term "allogeneic" as used herein refers to being genetically different although belonging to or obtained from the same species.

The term "amniotic stem cells" as used herein refers to pluripotent stem cells, multipotent stem cells and progenitor cells derived from amniotic membrane, which can give rise to a limited number of cell types in vitro and/or in vivo under an appropriate condition, and expressly includes both amniotic epithelial cells and amniotic stromal cells. Cells found in the amniotic fluid are derived from the amniotic membrane and can also be referred to as "amniotic stem cells".

The terms "artificial" and "artificially" as used herein refers to a composition such as a medium that is non-naturally existing and/or is prepared in vitro using a non-naturally occurring process.

The term "autologous" as used herein means derived from the same organism.

The term "autologous graft" or "autograft" as used herein refers to a tissue that is grafted into a new position in or on the body of the same individual.

The term "basic fibroblast growth factor" (bFGF) as used herein refers to a multifunctional effector for many cells of mesenchymal and neuroectodermal origin that is a potent inducer of neovascularization and angiogenesis.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention.

The term "bone" as used herein refers to a hard connective tissue consisting of cells embedded in a matrix of mineralized ground substance and collagen fibers. The fibers are impregnated with a form of calcium phosphate similar to hydroxyapatite as well as with substantial quantities of carbonate, citrate and magnesium. Bone consists of a dense outer layer of compact substance or cortical substance covered by the periosteum and an inner loose, spongy substance; the central portion of a long bone is filled with marrow.

The term "bone morphogenetic protein (BMP)" as used herein refers to a group of cytokines that are part of the transforming growth factor-$\beta$ (TGF-$\beta$) superfamily. BMP ligands bind to a complex of the BMP receptor type II and a BMP receptor type I (Ia or Ib). This leads to the phosphorylation of the type I receptor that subsequently phosphorylates the BMP-specific Smads (Smad1, Smad5, and Smad8), allowing these receptor-associated Smads to form a complex with Smad4 and move into the nucleus where the Smad complex binds a DNA binding protein and acts as a transcriptional enhancer. BMPs have a significant role in bone and cartilage formation in vivo. It has been reported that most BMPs are able to stimulate osteogenesis in mature osteoblasts, while BMP-2, 6, and 9 may play an important role in inducing osteoblast differentiation of mesenchymal stem cells. Cheng, H. et al., J. Bone & Joint Surgery 85: 1544-52 (2003).

The terms "cancellous bone" or "trabecular bone" as used herein refer to the spongy bone found in the inner parts of compact bone in which the matrix forms a lattice of large plates and rods known as the trabeculae, which anastomose to form a latticework. This latticework partially encloses many intercommunicating spaces filled with bone marrow. The marrow spaces are relatively large and irregularly arranged, and the bone substance is in the form of slender anastomosing trabeculae and pointed spicules.

The term "chemokine" as used herein refers to a class of chemotactic cytokines that signal leukocytes to move in a specific direction.

The terms "chemotaxis" or "chemotactic" refer to the directed motion of a motile cell or part along a chemical concentration gradient towards environmental conditions it deems attractive and/or away from surroundings it finds repellent.

The term "chondrocytes" as used herein refers to cells found in cartilage that produce and maintain the cartilaginous matrix for, for example, joints, ear canals, trachea, epiglottis, larynx, the discs between vertebrae and the ends of ribs. From least to terminally differentiated, the chondrocytic lineage is (i) Colony-forming unit-fibroblast (CFU-F); (ii) mesenchymal stem cell/marrow stromal cell (MSC); (iii) chondrocyte.

The term "chondrogenesis" as used herein refers to the formation of new cartilage from cartilage forming or chondrocompetent cells.

The term "chondrogenic" as used herein refers to a potential of precursor cells to differentiate into cartilage forming or chondrocompetent cells, wherein the chondrogenic cells include one or more of a chondrogenic stem cell, a tissuegenic cell, a precursor cell, a progenitor cell, an immature cell, a non-terminally differentiated cell, a cell with differentiation potential, or a combination thereof.

The terms "cortical bone" or "compact bone" as used herein refer to the dense outer layer of bone that consists largely of concentric lamellar osteons and interstitial lamellae. The spaces or channels are narrow and the bone substance is densely packed.

The term "interleukin" as used herein refers to a cytokine secreted by white blood cells as a means of communication with other white blood cells.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferon's and interleukin-10; tumor necrosis factor ("TNF")-related molecules, including TNF$\alpha$ and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Nonlimiting examples of cytokines include e.g., IL-1$\alpha$, IL-$\beta$, IL-2, IL-3, IL-4, IL-5, IL-6, IL-7, IL-8, IL-9, IL-10, IL-11, IL-12/IL-23 P40, IL13, IL-17, IL-18, TGF-$\beta$, IFN-$\gamma$, GM-CSF, Gro$\alpha$, MCP-1 and TNF-$\alpha$.

The term "decellularize" refers to the removal of at least a portion of the endogenous cells from a tissue. The term "devitalize" refers to the killing of cells which could occur with or without cell removal.

The term "Demineralized bone matrix" (DBM) refers to a bone-derived material that has osteoconductive and osteoinductive activity. DBM may be prepared by either acid extraction or non-acid extraction of allograft bone, resulting in loss of most of the mineralized component but retention of collagen and noncollagenous proteins, including growth factors. Methods for preparing demineralized bone matrix from bone are known in the art, as disclosed, for example, in U.S. Pat. Nos. 5,073,373; 5,484,601; and 5,284,655, which are incorporated herein by reference. DBM may be prepared from autologous bone, allogeneic (or "allograft") bone, or xenogeneic bone. DBM may be prepared from cancellous bone, cortical bone, or combinations of cancellous and cortical bone. For the purpose of the present disclosure, demineralized bone includes bone matrix having a residual mineral content of 8% or less (w/w), 5% or less (w/w), 2% or less (w/w), 1% or less (w/w), 0.5% or less (w/w), or consisting essentially of collagen, non-collagen proteins such as growth factors, and other nonmineral substances found in the original bone, although not necessarily in their original quantities. Partially demineralized bone includes bone matrix having any mineral content removed relative to naturally occurring bone, such mineral content could be 20% or less (w/w), 15% or less (w/w), 10% or less (w/w), or lower. The term "demineralized cortical bone" (DCB) as used herein refers to a demineralized allograft cortical bone The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as alkylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamate, and can include amino acids that are not linked by peptide bonds. Such peptide derivatives can be incorporated during synthesis of a peptide, or a peptide can be modified by well-known chemical modification methods (see, e.g., Glazer et al., Chemical Modification of Proteins, Selected Methods and Analytical Procedures, Elsevier Biomedical Press, New York (1975)).

The term "differentiation" as used herein refers to the process of development with an increase in the level of organization or complexity of a cell or tissue, accompanied with a more specialized function.

The term "nonexpanded" as used herein refers to a cell population that has not been grown in culture (in vitro) to increase the number of cells in the cell population.

The term "endogenous" as used herein refers to that which is naturally occurring, incorporated within, housed within, adherent to, attached to or resident in.

The term "extracellular matrix" as used herein refers to a scaffold in a cell's external environment with which the cell interacts via specific cell surface receptors. The extracellular matrix serves many functions, including, but not limited to, providing support and anchorage for cells, segregating one tissue from another tissue, and regulating intracellular communication. The extracellular matrix is composed of an interlocking mesh of fibrous proteins and glycosaminoglycans (GAGs). Examples of fibrous proteins found in the extracellular matrix include collagen, elastin, fibronectin, and laminin. Examples of GAGs found in the extracellular matrix include proteoglycans (e.g., heparin sulfate), chondroitin sulfate, keratin sulfate, and non-proteoglycan polysaccharide (e.g., hyaluronic acid). The term "proteoglycan" refers to a group of glycoproteins that contain a core protein to which is attached one or more glycosaminoglycans.

The term "factors" as used herein refers to nonliving components that have a chemical or physical effect. For example, a "paracrine factor" is a diffusible signaling molecule that is secreted from one cell type that acts on another cell type in a tissue. The term "secreted factors" refer to factors that are secreted or otherwise produced by cells, such as extracellular macromolecules, growth factors, cytokines and adipokines, into e.g., the surrounding extracellular matrix or medium.

The term "graft" as used herein refers to a tissue, biologic fluid or organ transplanted from a donor to a recipient. It includes, but is not limited to, a self-tissue transferred from one body site to another in the same individual ("autologous graft"), a tissue transferred between genetically identical individuals or sufficiently immunologically compatible to allow tissue transplant ("syngeneic graft"), a tissue transferred between genetically different members of the same species ("allogeneic graft" or "allograft"), and a tissue transferred between different species ("xenograft"). The terms "graft" and "tissue graft" can be used interchangebly.

The term "growth factor" as used herein refers to extracellular polypeptide molecules that bind to a cell-surface receptor triggering an intracellular signaling pathway, leading to proliferation, differentiation, or other cellular response.

The term "growth induction" as used herein refers to a process by which cells are stimulated to grow, develop, differentiate, de-differentiate and/or trans-differentiate into a population of at least partially identical cells or an ensemble of cells that are not necessarily identical. This ensemble of cells may be a tissue or an organ.

The term "growth-inductive components" refers to biological and/or chemical factors or substances that stimulate cells to grow, develop, differentiate, de-differentiate and/or trans-differentiate into a population of at least partially identical cells or an ensemble of cells that are not necessarily identical. Growth-inductive components include, but are not limited to, mitogens, growth factors and cytokines. Exemplary growth-inductive components include, but are not limited to, ions (e.g., calcium); hormones; steroids (e.g., estrogens); terpenoids (e.g., retinoic acid); peptides (e.g., Parathyroid hormone (PTH), parathyroid hormone-related peptide (PTHrP), insulin growth factors (e.g., TGF-β, BMPs, IGF-1, VEGF, PDGF, FGF); transcription factors (e.g., Wnt, SOX-9); eicosanoids (e.g., prostaglandins); catabolic interleukins (e.g., IL-1); and anabolic interleukins (e.g., IL-6, IL-4 and IL-10). Other growth-inductive components are listed in Gaissmaier et al. (2008), Int. J. Care Injured, 39S1: S88-S96, the entire contents of which are incorporated by reference herein.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "matrix" refers to a surrounding substance within which something is contained or embedded.

The term "mesenchymal stem cells (MSCs)" as used herein refers to non-blood adult stem cells found in a variety of tissues. They are characterized by their spindle-shape morphologically; by the expression of specific markers on their cell surface; and by their ability under appropriate conditions, to differentiates along a minimum of three lineages (osteogenic, chondrogenic and adipogenic). When referring to bone or cartilage, MSCs commonly are known as osteochondrogenic, osteogenic, or chondrogenic, since a single MSC has shown the ability to differentiate into chondrocytes or osteoblasts, depending on the medium.

MSCs secrete many biologically important molecules, including interleukins 6, 7, 8, 11, 12, 14, and 15, M-CSF, Flt-3 ligand, SCF, LIF, bFGF, VEGF, P1GF and MCP1 (Majumdar et al., J. Cell Physiol. 176: 57-66 (1998), Kinnaird et al, Circulation 109: 1543-49 (2004)). In 2004, it was reported that no single marker that definitively identifies MSCs in vivo had yet been identified, due to the lack of consensus from diverse documentations of the MSC phenotype. Baksh et al., J. Cell. Mol. Med. 2004, 8(3) 301-16, 305. There is general agreement that MSCs lack typical hematopoietic antigens, namely CD14, CD34, and CD45. (Id.; citing Pittenger, et al., Science. 1999. 284: 143-47).

The term "multipotent" as used herein refers to a cell capable of giving rise to a limited number of cell types of a particular cell line.

The term "myogenic" refers to a potential of precursor cells to differentiate into a muscle forming or myocompetent cells, wherein the myogenic cells include one or more of a myogenic stem cell, a tissuegenic cell, a precursor cell, a progenitor cell, an immature cell, a non-terminally differentiated cell, a cell with differentiation potential, or a combination thereof.

The term "osteoblasts" as used herein refers to cells that arise when osteoprogenitor cells or mesenchymal cells, which are located near all bony surfaces and within the bone marrow, differentiate under the influence of growth factors. Osteoblasts, which are responsible for bone matrix synthesis, secrete a collagen rich ground substance essential for later mineralization of hydroxyapatite and other crystals. The collagen strands form osteoids (spiral fibers of bone matrix). Osteoblasts cause calcium salts and phosphorus to precipitate from the blood, which bond with the newly formed osteoid to mineralize the bone tissue. Once osteoblasts become trapped in the matrix they secrete, they become osteocytes. From least to terminally differentiated, the osteocyte lineage is (i) Colony-forming unit-fibroblast (CFU-F); (ii) mesenchymal stem cell/marrow stromal cell (MSC); (iii) osteoblast; and (iv) osteocyte.

The term "osteocalcin" as used herein refers to a protein constituent of bone; circulating levels are used as a marker of increased bone turnover.

The term "osteoclast" as used herein refers to large multinucleate cells associated with areas of bone resorption (breakdown).

The term "osteoconduction" as used herein refers to a process by which bone is directed so as to conform to a material's surface. An osteoconductive surface is one that permits bone growth on its surface or down into pores, channels or pipes. Osteoconductive material facilitates the spontaneous formation of bone by furnishing a microenvironment that supports the ingrowth of blood vessels, perivascular tissue and osteoprogenitor cells into the site where it is deposited. Examples of osteoconductive materials, include, but not limited to, processed human bone (allograft bone), purified collagen, calcium phosphate ceramics, synthetic polymers, BMP-2 and 4, VEGF, bFGF, TGF-β, and PDGF.

The term "osteoconductive matrix" as used herein refers to a matrix that is inert in and of itself but on which cells can climb and grow bone.

The term "osteogenic" refers to a potential of precursor cells to differentiate into bone forming or osteocompetent cells, wherein the osteogenic cells include one or more of an osteogenic stem cell, a tissuegenic cell, a precursor cell, a progenitor cell, an immature cell, a non-terminally differentiated cell, a cell with differentiation potential, or a combination thereof.

The term "osteogenesis" as used herein refers to the development or formation of new bone by bone forming or osteocompetent cells.

The term "osteoinduction" as used herein refers to a process by which primitive, undifferentiated or non-terminally differentiated pluripotent cells are stimulated to develop into a bone forming cell lineage thereby inducing osteogenesis. For example, the majority of bone healing in a fracture is dependent on osteoinduction. Osteoinductive materials can be generated by combining a porous scaffold with osteogenic cells and/or osteoinductive components, including, but not limited to, growth factors such as BMP-2 and 4, VEGF, bFGF, TGF-β, and PDGF.

The term "osteoinductive matrix" as used herein refers to a matrix containing a substance or substances that recruit local cells to induce (meaning to cause, bring about, bring about, or trigger) local cells to produce bone.

The terms "osteoinductive components" or "osteogenic factors" are used interchangeably to refer to the plethora of mediators associated with bone development and repair, including, but not limited to, bone morphogenic proteins (BMPs), vascular endothelial growth factor (VEGF), basic fibroblast growth factor (bFGF), transforming growth factor beta (TGFβ), and platelet-derived growth factor (PDGF).

The term "osteointegration" refers to an anchorage mechanism whereby nonvital components can be incorporated reliably into living bone and that persist under all normal conditions of loading.

The term "periosteum" as used herein refers to the normal investment of bone, consisting of a dense, fibrous outer layer, to which muscles attach, and a more delicate, inner layer capable of forming bone.

The term "Platelet Derived Growth Factor" (PDGF) as used herein refers to a major mitogen for connective tissue cells and certain other cell types. It is a dimeric molecule consisting of disulfide-bonded, structurally similar A and B-polypeptide chains, which combine to homo- and heterodimers. The PDGF isoforms exert their cellular effects by binding to and activating two structurally related protein tyrosine kinase receptors, the α-receptor and the β-receptor. Activation of PDGF receptors leads to stimulation of cell growth, but also to changes in cell shape and motility; PDGF induces reorganization of the actin filament system and stimulates chemotaxis, i.e., a directed cell movement toward a gradient of PDGF. In vivo, PDGF plays a role in embryonic development and during wound healing.

The term "pluripotent" as used herein refers to the ability to develop into multiple cells types, including all three embryonic lineages, forming the body organs, nervous system, skin, muscle and skeleton.

The terms "priming" "pre-conditioning" and "conditioning" are used interchangeably herein and refer to the use of one or more stimuli to prepare a tissue for use in grafting. The term "non-primed" tissue refers to a tissue that is otherwise treated in the same manner except the priming condition.

The term "progenitor cell" as used herein refers to an early descendant of a stem cell that can only differentiate, but can no longer renew itself. Progenitor cells mature into precursor cells that mature into mature phenotypes. Hematopoietic progenitor cells are referred to as colony-forming units (CFU) or colony-forming cells (CFC). The specific lineage of a progenitor cell is indicated by a suffix, such as, but not limited to, CFU-E (erythrocytic), CFU-F (fibroblastic), CFU-GM (granulocytic/macrophage), and CFU-GEMM (pluripotent hematopoietic progenitor). Osteoclasts arise from hematopoietic cells of the monocyte/neutrophil lineage (CFU-GM). Osteoprogenitor cells arise from mesenchymal stem cells and are committed to an osteocyte lineage.

The term "regeneration" or "regenerate" as used herein refers to a process of recreation, reconstitution, renewal, revival, restoration, differentiation and growth to form a tissue with characteristics that conform with a natural counterpart of the tissue.

The term "resident," and its various grammatical forms, as used herein refers to being present habitually, existing in or intrinsic to or incorporated therein.

The term "scaffold" as used herein refers to a structure capable of supporting a three-dimensional tissue formation. A three-dimensional scaffold is believed to be critical to replicate the in vivo milieu and to allow the cells to influence their own microenvironment. Scaffolds may serve to promote cell attachment and migration, to deliver and retain cells and biochemical factors, to enable diffusion of vital cell nutrients and expressed products, and to exert certain mechanical and biological influences to modify the behavior of the cell phase. A scaffold utilized for tissue reconstruction has several requisites. Such a scaffold should have a high porosity and an adequate pore size to facilitate cell seeding and diffusion of both cells and nutrients throughout the whole structure. Biodegradability of the scaffold is also an essential requisite. The scaffold should be absorbed by the surrounding tissues without the necessity of a surgical removal, such that the rate at which degradation occurs coincides as closely as possible with the rate of tissue formation. As cells are fabricating their own natural matrix structure around themselves, the scaffold provides structural integrity within the body and eventually degrades leaving the neotissue (newly formed tissue) to assume the mechanical load.

The term "stem cells" refers to undifferentiated cells having high proliferative potential with the ability to self-renew (make more stem cells by cell division) that can generate daughter cells that can undergo terminal differentiation into more than one distinct cell phenotype.

The term "stimuli" or "stimulating agent" as used herein refers to an environmental (e.g., microenvironmental) or external force, condition, factor or substance that exerts some change or effect, in particular in the context of priming a tissue for grafting.

The phrase "recipient" or "subject in need thereof" as used herein refers to a patient that (i) will receive or be administered at least one graft (e.g., allograft), (ii) is receiving or administered at least one graft (e.g., allograft); or (iii) has received or administered at least one graft (e.g., allograft), unless the context and usage of the phrase indicates otherwise. The term "donor" refers to a patient who provides at least one graft. Donor and recipient can be the same or different.

The term "tissuegenic" as used herein refers to a potential of an precursor cell to differentiate into a mature cell type and to regenerate a tissue, wherein the tissuegenic cells include one or more of a tissuegenic stem cell, a tissuegenic cell, a precursor cell, a progenitor cell, an immature cell, a non-terminally differentiated cell, a cell with differentiation potential, or a combination thereof. Exemplary tissuegenic cells include but are not limited to a stem cell, a progenitor cell or a combination thereof. The term "osteogenic" refers more specifically to cell differentiation and tissue regeneration with regard to bone.

The term "vascularization" as used herein refers to a process of ingrowth of blood vessels and perivascular tissue within a growth-conductive matrix to support the deposition and adhesion of tissuegenic cells to effect tissue regeneration.

The terms "VEGF", "VEGF-1" or "vascular endothelial growth factor-1" are used interchangeably herein to refer to a cytokine that mediates numerous functions of endothelial cells including proliferation, migration, invasion, survival, and permeability. The term "VEGF-2" refers to a regulator for growth of vascular endothelial and smooth muscle cells. VEGF-2 stimulates the growth of human vascular endothelial cells but inhibits growth of human aortic smooth muscle cells induced by platelet-derived growth factor.

The term "viable" as used herein refers to having the ability to grow, expand, or develop; capable of living.

The term "xenogeneic" as used herein refers to cells or tissues derived from individuals of different species, including, but not limited to, porcine, bovine, caprine, equine, canine, lapine, feline, and/or non-human mammals, such as, but not limited to, whale, and porpoise.

2. Tissue Compartments and Cells Therein

The methods and compositions of the present invention can be applied to any tissue or organ suitable for grafting. Some exemplary tissues and associated cells are described herein. One or ordinary skill in the art would understand that the present invention is applicable to other tissue and organ types as well.

In multicellular organisms, cells that are specialized to perform common functions are usually organized into cooperative assemblies embedded in a complex network of secreted extracellular macromolecules, the extracellular matrix (ECM), to form specialized tissue compartments. Individual cells in such tissue compartments are in contact with ECM macromolecules. The ECM helps hold the cells and compartments together and provides an organized lattice or scaffold within which cells can migrate and interact with one another. In many cases, cells in a compartment can be held in place by direct cell-cell adhesions. In vertebrates, such compartments may be of four major types, a connective tissue (CT) compartment, an epithelial tissue (ET) compartment, a muscle tissue (MT) compartment and a nervous tissue (NT) compartment, which are derived from three embryonic germ layers: ectoderm, mesoderm and endoderm. The NT and portions of the ET compartments are differentiated from the ectoderm; the CT, MT and certain portions of the ET compartments are derived from the mesoderm; and further portions of the ET compartment are derived from the endoderm.

The connective tissue compartment contains cells that primarily function to elaborate and maintain ECM structure. The character of the extracellular matrix is region-specific and is determined by the amount of the extracellular materials.

Common cell types of connective tissue compartments include: fibroblasts, macrophages, mast cells, and plasma cells. Specialized connective tissue compartments, such as cartilage, bone, and the vasculature, and those with special properties, such as adipose, tendons, ligaments, etc., have specialized cells to perform specialized functions.

2.1. Adipose 2.1.1. Adipose Tissue Compartment

Adipose tissue compartments are dynamic, multifunctional, ubiquitous and loose connective tissue compartments. Adipose comprises fibroblasts, smooth muscle cells, endothelial cells, leukocytes, macrophages, and closely packed mature lipid-filled fat cells, termed adipocytes, with characteristic nuclei pushed to one side, embedded within an areolar matrix that are located in subcutaneous layers of skin and muscle (panniculus adiposus), in the kidney region, cornea, breasts, mesenteries, mediastinium, and in the cervical, axillary and inguinal regions. Adipocytes play a primary role in energy storage and in providing insulation and protection. As sites of energy storage, adipocytes regulate the accumulation or mobilization of triacylglycerol in response to the body's energy requirements and store energy in the form of a single fat droplet of triglycerides.

Each adipocyte is surrounded by a thick ECM called the basal lamina. The strong adipocyte ECM scaffold lowers mechanical stress by spreading forces over a large surface area of the adipose tissue compartments. The ECM composition of adipocytes is similar to that of other cell types, but it is the relative quantity of individual components that impart cell specificity. Adipocyte ECM is particularly enriched in collagen VI, a coiled coil comprising $\alpha1(VI)$, $\alpha2(VI)$ and $\alpha3(VI)$ subunits. Collagen VI binds to collagen IV and also to other matrix proteins such as proteoglycans and fibronectin. The core proteins associated with the adipocyte ECM, which have been identified through with current proteomic techniques, have been reviewed by Mariman et al. (Cell. Mol. Life Sci., 2010, 67:1277-1292).

Adipocyte ECM undergoes biphasic development during adipogenesis, the process of formation of mature adipose tissue compartments. There is an initial decrease in collagen I and III, whereas their levels come back to pre-differentiation state at later stages. Mature adipocyte ECM is maintained in a dynamic state with constant turnover of ECM components by a balance of activities of ECM constructive enzymes and ECM degradation enzymes. In early stages of differentiation, the balance is shifted towards the constructive factors. (Mariman et al., 2010, Cell. Mol. Life Sci., 67:1277-1292). Maturation of newly synthesized ECM components is initiated in the ER lumen where ECM proteins undergo biochemical modifications and proteolytic processing prior to assembly. For collagen, such modifications include proline- and lysine-hydroxylation and glycosylation and clipping of N- and C-terminal peptides by respective procollagen-N- and -C-collagenase. Processed proteins are then assembled and secreted into the extracellular environment where they undergo further processing by secreted extracellular modification and processing enzymes. As the preadipocytes differentiate and begin to store fat, ECM assumes a basal laminar structure.

2.1.2. Adipose-Derived Stem Cells

Adipose also comprises a population of pluripotent stem cells that have the potential to give rise to cells of all three embryonic lineages: ectodermal, mesodermal and endodermal. Adipogenesis, which comprises the steps of differentiation of such pluripotent cells to mature adipocytes, is initiated by differentiation of these pluripotent cells to give rise to a population of mesenchymal precursor cells or mesenchymal stem cells (MSCs), which have the potential to differentiate into a variety of mesodermal cell lineages such as for example, myoblasts, chondroblasts, osteoblasts and adipocytes. In the presence of appropriate environmental and gene expression signals, the MSCs go through growth arrest and differentiate into precursors with a determined fate that undergo clonal expansion, become committed and terminally differentiate to give rise to mature cells. The population of MSCs and more committed adipose progenitors that are found along with the stroma of adipose tissue collectively are termed adipose-derived stem cells (ASCs). These cells have a characteristic CD45-CD31-CD34+CD105+ surface phenotype. In the case of adipocyte differentiation, ASCs differentiate to proadipocytes that undergo final differentiation to give rise to mature adipocytes. Mesenchymal progenitor cells with chondrogenic potential have also been identified in the infrapatellar fat pad in joints. (Lee et al., Tissue Eng. 2010, 16(1): 317-325). Cell lineages and respective inductive factors that can be derived from ASC lines have been reviewed by Brown et. al., Plast. Reconstr. Surg., 2010, 126(6): 1936-1946; Gregoire et al., Physiol. Rev., 1998, 78(3): 783-809).

2.1.3. Adipose Secreted Factors

Adipose is considered a secretory organ. The adipose secretome not only includes structural and soluble factors contributing to the formation of the adipose matrix, but also a horde of soluble factors with endocrine function, such as growth factors, hormones, chemokines and lipids, collectively termed adipokines. Exemplary adipokines include, without limitation, leptin, adiponectin, resistin, interleukin 6 (IL-6), monocyte chemoattractant protein 1 (MCP-1), tumor necrosis factor alpha (TNF-α); fibroblast growth factor (FGF), and vascular endothelial growth factor (VEGF). Exemplary immunogical adipokines, particularly involved in inflammatory pathways include, without limitation, serum amyloid A3 (SAA3), IL-6, adiponectin, TNF-α and haptoglobin. Exemplary adipokines involved in the production of new blood vessels include, without limitation, angiopoietin-1, angiopoietin-2, VEGF, transforming growth factor beta (TGF-β), hepatic growth factor (HGF), stromal derived growth factor 1 (SDF-1), TNF-α, resistin, leptin, tissue factor, placental growth factor (PGF), insulin like growth factor (IGF), and monobutyrin.

Adiponectin, a key metabolic factor secreted from adipocytes, is a 30-KDa protein that may exist as a trimer, low molecular weight hexamers or high molecular weight 18mers. Adiponectin circulates throughout the plasma and has a variety of metabolic effects including, but not limited to, glucose lowering and cardioprotection stimulation of smooth muscle proliferation. Adiponectin has been implicated in a number of pathological conditions including, but not limited to diabetes, obesity, metabolic syndrome, cardiovascular disease and wound healing.

Resistin, a member of the resistin-like (RELM) hormone family, is secreted by stromal vascular cells of adipose. Resistin is secreted in two multimeric isoforms and functions to counterbalance the insulin sensitizing effects of adiponectin. (Truillo, M. E. and Scherer P. E., Endocrine Rev. 2006, 27(7): 762-778).

Secretions from resident adipocytes, macrophages and ASCs collectively contribute to the adipose secretome. Angiogenic, hematopoietic, and proinflammatory adipokine profiles of ASCs are reported by Kilroy et. al., Cell. Physiol., 2007, J. 212: 702-709.)

2.2. Bone 2.2.1. Osseous Tissue Compartment

Osseous tissue is a rigid form of connective tissue normally organized into definite structures, the bones. These form the skeleton, serve for the attachment and protection of the soft parts, and, by their attachment to the muscles, act as levers that bring about body motion. Bone is also a storage place for calcium that can be withdrawn when needed to maintain a normal level of calcium in the blood.

Bones can be classified according to their shape. Examples of bone types include: long bones whose length is greater than their widths (e.g., femur (thigh bone), humerus (long bone of the upper limb), tibia (shin bone), fibula (calf bone), radius (the outer of the two bones of the forearm), and ulna (inner of two bones of the forearm)), short bones whose length and width is approximately equal (e.g., carpals bones (wrist bones in the hand)), flat bones (e.g., cranium (skull bones surrounding the brain), scapula (shoulder blade), and ilia (the uppermost and largest bone of the pelvis)), irregular bones (e.g., vertebra), and Sesamoid bones, small bones present in the joints to protect tendons (fibrous connective tissues that connect muscles to the bones, e.g., patella bones (knee cap). Grossly, two types of bone may be distinguished: cancellous, trabecular or spongy bone, and cortical, compact, or dense bone.

Cortical bone, also referred to as compact bone or dense bone, is the tissue of the hard outer layer of bones, so-called due to its minimal gaps and spaces. This tissue gives bones their smooth, white, and solid appearance. Cortical bone consists of haversian sites (the canals through which blood vessels and connective tissue pass in bone) and osteons (the basic units of structure of cortical bone comprising a haversian canal and its concentrically arranged lamellae), so that in cortical bone, bone surrounds the blood supply. Cortical bone has a porosity of about 5% to about 30%, and accounts for about 80% of the total bone mass of an adult skeleton.

2.2.2. Cancellous Bone (Trabecular or Spongy Bone)

Cancellous bone tissue, an open, cell-porous network also called trabecular or spongy bone, fills the interior of bone and is composed of a network of rod- and plate-like elements that make the overall structure lighter and allows room for blood vessels and marrow so that the blood supply surrounds bone. Cancellous bone accounts for the remaining 20% of total bone mass but has nearly ten times the surface area of cortical bone. It does not contain haversian sites and osteons and has a porosity of about 30% to about 90%.

The head of a bone, termed the epiphysis, has a spongy appearance and consists of slender irregular bone trabeculae, or bars, which anastomose to form a lattice work, the interstices of which contain the marrow, while the thin outer shell appears dense. The irregular marrow spaces of the epiphysis become continuous with the central medullary cavity of the bone shaft, termed the diaphysis, whose wall is formed by a thin plate of cortical bone.

Both cancellous and cortical bone have the same types of cells and intercellular substance, but they differ from each other in the arrangement of their components and in the ratio of marrow space to bone substance. In cancellous bone, the marrow spaces are relatively large and irregularly arranged, and the bone substance is in the form of slender anastomosing trabeculae and pointed spicules. In cortical bone, the spaces or channels are narrow and the bone substance is densely packed.

With very few exceptions, the cortical and cancellous forms are both present in every bone, but the amount and distribution of each type vary considerably. The diaphyses of the long bones consist mainly of cortical tissue; only the innermost layer immediately surrounding the medullary cavity is cancellous bone. The tabular bones of the head are composed of two plates of cortical bone enclosing marrow space bridged by irregular bars of cancellous bone. The epiphyses of the long bones and most of the short bones consist of cancellous bone covered by a thin outer shell of cortical bone.

Each bone, except at its articular end, is surrounded by a vascular fibroelastic coat, the periosteum. The so-called endosteum, or inner periosteum of the marrow cavity and marrow spaces, is not a well-demarcated layer; it consists of a variable concentration of medullary reticular connective tissue that contains osteogenic cells that are in immediate contact with the bone tissue.

2.2.3. Components of Bone

Bone is composed of cells and an intercellular matrix of organic and inorganic substances. The organic fraction consists of collagen, glycosaminoglycans, proteoglycans, and glycoproteins. The protein matrix of bone largely is composed of collagen, a family of fibrous proteins that have the ability to form insoluble and rigid fibers. The main collagen in bone is type I collagen. The inorganic component of bone, which is responsible for its rigidity and may constitute up to two-thirds of its fat-free dry weight, is composed chiefly of calcium phosphate and calcium carbonate, in the form of calcium hydroxyapatite, with small amounts of magnesium hydroxide, fluoride, and sulfate. The composition varies with age and with a number of dietary factors. The bone minerals form long fine crystals that add strength and rigidity to the collagen fibers; the process by which it is laid down is termed mineralization.

2.2.4. Bone Cells and Secreted Factors

Four cell types in bone are involved in its formation and maintenance. These are 1) osteoprogenitor cells, 2) osteoblasts, 3) osteocytes, and 4) osteoclasts.

Osteoprogenitor cells arise from mesenchymal cells, and occur in the inner portion of the periosteum and in the endosteum of mature bone. They are found in regions of the embryonic mesenchymal compartment where bone formation is beginning and in areas near the surfaces of growing bones. Structurally, osteoprogenitor cells differ from the mesenchymal cells from which they have arisen. They are irregularly shaped and elongated cells having pale-staining cytoplasm and pale-staining nuclei. Osteoprogenitor cells, which multiply by mitosis, are identified chiefly by their location and by their association with osteoblasts. Some osteoprogenitor cells differentiate into osteocytes. While osteoblasts and osteocytes are no longer mitotic, it has been shown that a population of osteoprogenitor cells persists throughout life.

Osteoblasts, which are located on the surface of osteoid seams (the narrow region on the surface of a bone of newly formed organic matrix not yet mineralized), are derived from osteoprogenitor cells. They are immature, mononucleate, bone-forming cells that synthesize collagen and control mineralization. Osteoblasts can be distinguished from osteoprogenitor cells morphologically; generally they are larger than osteoprogenitor cells, and have a more rounded nucleus, a more prominent nucleolus, and cytoplasm that is much more basophilic. Osteoblasts make a protein mixture known as osteoid, primarily composed of type I collagen, which mineralizes to become bone. Osteoblasts also manufacture hormones, such as prostaglandins, alkaline phosphatase, an enzyme that has a role in the mineralization of bone, and matrix proteins.

Osteocytes, star-shaped mature bone cells derived from osteoblasts and the most abundant cell found in compact bone, maintain the structure of bone. Osteocytes, like osteoblasts, are not capable of mitotic division. They are actively involved in the routine turnover of bony matrix and reside in small spaces, cavities, gaps or depressions in the bone matrix called lacuna. Osteocytes maintain the bone matrix, regulate calcium homeostasis, and are thought to be part of the cellular feedback mechanism that directs bone to form in places where it is most needed. Bone adapts to applied forces by growing stronger in order to withstand them; osteocytes may detect mechanical deformation and mediate bone-formation by osteoblasts.

Osteoclasts, which are derived from a monocyte stem cell lineage and possess phagocytic-like mechanisms similar to macrophages, often are found in depressions in the bone referred to as Howship's lacunae. They are large multinucleated cells specialized in bone resorption. During resorption, osteoclasts seal off an area of bone surface; then, when activated, they pump out hydrogen ions to produce a very acid environment, which dissolves the hydroxyapatite component. The number and activity of osteoclasts increase when calcium resorption is stimulated by injection of parathyroid hormone (PTH), while osteoclastic activity is suppressed by injection of calcitonin, a hormone produced by thyroid parafollicular cells.

The bone matrix accounts for about 90% of the total weight of compact bone and is composed of microcrystalline calcium phosphate resembling hydroxyapatite (60%) and fibrillar type I collagen (27%). The remaining 3% consists of minor collagen types and other proteins including osteocalcin, osteonectin, osteopontin, bone sialoprotein, as well as proteoglycans, glycosaminoglycans, and lipids.

Bone matrix is also a major source of biological information that skeletal cells can receive and act upon. For example, extracellular matrix glycoproteins and proteoglycans in bone bind a variety of growth factors and cytokines, and serve as a repository of stored signals that act on osteoblasts and osteoclasts. Examples of growth factors and cytokines found in bone matrix include, but are not limited to, Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors.

There is an emerging understanding that extracellular matrix molecules themselves can serve regulatory roles, providing both direct biological effects on cells as well as key spatial and contextual information.

Examples of factors secreted by bone cells include, but are not limited to, Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors.

2.2.5. Periosteum and Endosteum

The periosteum is a fibrous connective tissue investment of bone, except at the bone's articular surface. Its adherence to the bone varies by location and age. In young bone, the periosteum is stripped off easily. In adult bone, it is more firmly adherent, especially so at the insertion of tendons and ligaments, where more periosteal fibers penetrate into the bone as the perforating fibers of Sharpey (bundles of collagenous fibers that pass into the outer circumferential lamellae of bone). The periosteum consists of two layers, the outer of which is composed of course, fibrous connective tissue containing few cells but numerous blood vessels and nerves. The inner layer, which is less vascular but more cellular, contains many elastic fibers. During growth, an osteogenic layer of primitive connective tissue forms the inner layer of the periosteum. In the adult, this is represented only by a row of scattered, flattened cells closely applied to the bone. The periosteum serves as a supporting bed for the blood vessels and nerves going to the bone and for the anchorage of tendons and ligaments. The osteogenic layer, which is considered a part of the periosteum, is known to furnish osteoblasts for growth and repair, and acts as an important limiting layer controlling and restricting the extend of bone formation. Because both the periosteum and its contained bone are regions of the connective tissue compartment, they are not separated from each other or from other connective tissues by basal laminar material or basement membranes. Perosteal stem cells have been shown to be important in bone regeneration and repair. (Zhang et al., J. Musculoskelet. Neuronal. Interact. 2005. 5(4): 360-362).

The endosteum lines the surface of cavities within a bone (marrow cavity and central canals) and also the surface of trabeculae in the marrow cavity. In growing bone, it consists of a delicate striatum of myelogenous reticular connective tissue, beneath which is a layer of osteoblasts. In the adult, the osteogenic cells become flattened and are indistinguishable as a separate layer. They are capable of transforming into osteogenic cells when there is a stimulus to bone formation, as after a fracture.

2.2.6. Bone Marrow

The marrow is a soft connective tissue that occupies the medullary cavity of the long bones, the larger central canals, and all of the spaces between the trabeculae of spongy bone. It consists of a delicate reticular connective tissue, in the meshes of which lie various kinds of cells. Two varieties of marrow are recognized: red and yellow. Red marrow is the only type found in fetal and young bones, but in the adult it is restricted to the vertebrae, sternum, ribs, cranial bones, and epiphyses of long bones. It is the chief site for the genesis of blood cells in the adult body. Yellow marrow consists primarily of fat cells that gradually have replaced the other marrow elements. Under certain conditions, the yellow marrow of old or emaciated persons loses most of its fat and assumes a reddish color and gelatinous consistency, known as gelatinous marrow. With adequate stimulus, yellow marrow may resume the character of red marrow and play an active part in the process of blood development.

2.2.7. Osteogenesis or Ossification

Osteogenesis or ossification is a process by which the bones are formed. There are three distinct lineages that generate the skeleton. The somites generate the axial skeleton, the lateral plate mesoderm generates the limb skeleton, and the cranial neural crest gives rise to the branchial arch, craniofacial bones, and cartilage. There are two major modes of bone formation, or osteogenesis, and both involve the transformation of a preexisting mesenchymal tissue into bone tissue. The direct conversion of mesenchymal tissue into bone is called intramembranous ossification. This process occurs primarily in the bones of the skull. In other cases, mesenchymal cells differentiate into cartilage, which is later replaced by bone. The process by which a cartilage intermediate is formed and replaced by bone cells is called endochondral ossification.

2.2.7.1. Intramembranous Ossification

Intramembraneous ossification is the characteristic way in which the flat bones of the scapula, the skull and the turtle shell are formed. In intramembraneous ossification, bones develop sheets of fibrous connective tissue. During intramembranous ossification in the skull, neural crest-derived mesenchymal cells proliferate and condense into compact nodules. Some of these cells develop into capillaries; others change their shape to become osteoblasts, committed bone precursor cells. The osteoblasts secrete a collagen-proteoglycan matrix that is able to bind calcium salts. Through this binding, the prebone (osteoid) matrix becomes calcified. In most cases, osteoblasts are separated from the region of calcification by a layer of the osteoid matrix they secrete. Occasionally, osteoblasts become trapped in the calcified matrix and become osteocytes. As calcification proceeds, bony spicules radiate out from the region where ossification began, the entire region of calcified spicules becomes surrounded by compact mesenchymal cells that form the periosteum, and the cells on the inner surface of the periosteum also become osteoblasts and deposit osteoid matrix parallel to that of the existing spicules. In this manner, many layers of bone are formed.

Intramembraneous ossification is characterized by invasion of capillaries into the mesenchymal zone, and the emergence and differentiation of mesenchymal cells into mature osteoblasts, which constitutively deposit bone matrix leading to the formation of bone spicules, which grow and develop, eventually fusing with other spicules to form trabeculae. As the trabeculae increase in size and number they become interconnected forming woven bone (a disorganized weak structure with a high proportion of osteocytes), which eventually is replaced by more organized, stronger, lamellar bone.

The molecular mechanism of intramembranoaus ossification involves bone morphogenetic proteins (BM's) and the activation of a transcription factor called CBFA1. Bone morphogenetic proteins, for example, BMP2, BMP4, and BMP7, from the head epidermis are thought to instruct the neural crest-derived mesenchymal cells to become bone cells directly. BMPs activate the Cbfa1 gene in mesenchymal cells. The CBFA1 transcription factor is known to transform mesenchymal cells into osteoblasts. Studies have shown that the mRNA for mouse CBFA1 is largely restricted to the mesenchymal condensations that form bone, and is limited to the osteoblast lineage. CBFA1 is known to activate the genes for osteocalcin, osteopontin, and other bone-specific extracellular matrix proteins.

2.2.7.2. Endochondral Ossification (Intracartilaginous Ossification)

Endochondral ossification, which involves the in vivo formation of cartilage tissue from aggregated mesenchymal cells, and the subsequent replacement of cartilage tissue by bone, can be divided into five stages. The skeletal components of the vertebral column, the pelvis, and the limbs are first formed of cartilage and later become bone.

First, the mesenchymal cells are committed to become cartilage cells. This commitment is caused by paracrine factors that induce the nearby mesodermal cells to express two transcription factors, Pax1 and Scleraxis. These transcription factors are known to activate cartilage-specific genes. For example, Scleraxis is expressed in the mesenchyme from the sclerotome, in the facial mesenchyme that forms cartilaginous precursors to bone, and in the limb mesenchyme.

During the second phase of endochondral ossification, the committed mesenchyme cells condense into compact nodules and differentiate into chondrocytes (cartilage cells that produce and maintain the cartilaginous matrix, which consists mainly of collagen and proteoglycans). Studies have shown that N-cadherin is important in the initiation of these condensations, and N-CAM is important for maintaining them. In humans, the SOX9 gene, which encodes a DNA-binding protein, is expressed in the precartilaginous condensations.

During the third phase of endochondral ossification, the chondrocytes proliferate rapidly to form the model for bone. As they divide, the chondrocytes secrete a cartilage-specific extracellular matrix.

In the fourth phase, the chondrocytes stop dividing and increase their volume dramatically, becoming hypertrophic chondrocytes. These large chondrocytes alter the matrix they produce (by adding collagen X and more fibronectin) to enable it to become mineralized by calcium carbonate.

The fifth phase involves the invasion of the cartilage model by blood vessels. The hypertrophic chondrocytes die by apoptosis, and this space becomes bone marrow. As the cartilage cells die, a group of cells that have surrounded the cartilage model differentiate into osteoblasts, which begin forming bone matrix on the partially degraded cartilage. Eventually, all the cartilage is replaced by bone. Thus, the cartilage tissue serves as a model for the bone that follows.

The replacement of chondrocytes by bone cells is dependent on the mineralization of the extracellular matrix. A number of events lead to the hypertrophy and mineralization of the chondrocytes, including an initial switch from aerobic to anaerobic respiration, which alters their cell metabolism and mitochondrial energy potential. Hypertrophic chondrocytes secrete numerous small membrane-bound vesicles into the extracellular matrix. These vesicles contain enzymes that are active in the generation of calcium and phosphate ions and initiate the mineralization process within the cartilaginous matrix. The hypertrophic chondrocytes, their metabolism and mitochondrial membranes altered, then die by apoptosis.

In the long bones of many mammals (including humans), endochondral ossification spreads outward in both directions from the center of the bone. As the ossification front nears the ends of the cartilage model, the chondrocytes near the ossification front proliferate prior to undergoing hypertrophy, pushing out the cartilaginous ends of the bone. The cartilaginous areas at the ends of the long bones are called epiphyseal growth plates. These plates contain three regions: a region of chondrocyte proliferation, a region of mature chondrocytes, and a region of hypertrophic chondrocytes. As the inner cartilage hypertrophies and the ossification front extends farther outward, the remaining cartilage in the epiphyseal growth plate proliferates. As long as the epiphyseal growth plates are able to produce chondrocytes, the bone continues to grow.

2.2.8. Bone Remodeling

Bone constantly is broken down by osteoclasts and re-formed by osteoblasts in the adult. It has been reported that as much as 18% of bone is recycled each year through the process of renewal, known as bone remodeling, which maintains bone's rigidity. The balance in this dynamic process shifts as people grow older: in youth, it favors the formation of bone, but in old age, it favors resorption.

As new bone material is added peripherally from the internal surface of the periosteum, there is a hollowing out of the internal region to form the bone marrow cavity. This destruction of bone tissue is due to osteoclasts that enter the bone through the blood vessels. Osteoclasts dissolve both the inorganic and the protein portions of the bone matrix. Each osteoclast extends numerous cellular processes into the matrix and pumps out hydrogen ions onto the surrounding material, thereby acidifying and solubilizing it. The blood vessels also import the blood-forming cells that will reside in the marrow for the duration of the organism's life.

The number and activity of osteoclasts must be tightly regulated. If there are too many active osteoclasts, too much bone will be dissolved, and osteoporosis will result. Conversely, if not enough osteoclasts are produced, the bones are not hollowed out for the marrow, and osteopetrosis (known as stone bone disease, a disorder whereby the bones harden and become denser) will result.

2.2.9. Bone Regeneration and Fracture Repair

A fracture, like any traumatic injury, causes hemorrhage and tissue destruction. The first reparative changes thus are characteristic of those occurring in any injury of soft tissue. Proliferating fibroblasts and capillary sprouts grow into the blood clot and injured area, thus forming granulation tissue. The area also is invaded by poly morphonuclear leukocytes and later by macrophages that phagocytize the tissue debris. The granulation tissue gradually becomes denser, and in parts of it, cartilage is formed. This newly formed connective tissue and cartilage is designated as a callus. It serves temporarily in stabilizing and binding together the fracture bone. As this process is taking place, the dormant osteogenic cells of the periosteum enlarge and become active osteoblasts. On the outside of the fractured bone, at first at some distance from the fracture, osseous tissue is deposited. This formation of new bone continues toward the fractured ends of the bone and finally forms a sheath-like layer of bone over the fibrocartilaginous callus. As the amount of bone increases, osteogenic buds invade the fibrous and cartilaginous callus and replace it with a bony one. The cartilage undergoes calcification and absorption in the replacement of the fibrocartilaginous callus and intramembraneous bone formation also takes place. The newly formed bone is at first a spongy and not a compact type, and the callus becomes reduced in diameter. At the time when this subperiosteal bone formation is taking place, bone also forms in the marrow cavity. The medullary bone growing centripetally from each side of the fracture unites, thus aiding the bony union.

The process of repair is, in general, an orderly process, but it varies greatly with the displacement of the fractured ends of the bone and the degree of trauma inflicted. Uneven or protruding surfaces gradually are removed, and the healed bone, especially, in young individuals, assumes its original contour.

2.2.10. Osteogenesis and Angiogenesis

Skeletal development and fracture repair includes the coordination of multiple events such as migration, differentiation, and activation of multiple cell types and tissues. The development of a microvasculature and microcirculation is important for the homeostasis and regeneration of living bone, without which the tissue would degenerate and die. Recent developments using in vitro and in vivo models of osteogenesis and fracture repair have provided a better understanding of the recruitment nature of the vasculature in skeletal development and repair.

The vasculature transports oxygen, nutrients, soluble factors and numerous cell types to all tissues in the body. The growth and development of a mature vascular structure is one of the earliest events in organogenesis. In mammalian embryonic development, the nascent vascular networks develop by aggregation of de novo forming angioblasts into a primitive vascular plexus (vasculogenesis). This undergoes a complex remodeling process in which sprouting, bridging and growth from existing vessels (angiogenesis) leads to the onset of a functional circulatory system.

The factors and events that lead to the normal development of the embryonic vasculature are recapitulated during situations of neoangiogenesis in the adult. There are a number of factors involved in neoangiogenesis; these include, but are not limited to, Vascular Endothelial Growth Factor (VEGF), basic Fibroblast Growth Factor (bFGF), various members of the Transforming Growth factor beta (TGFβ) family and Hypoxia-Inducible Transcription Factor (HIF). Other factors that have angiogenic properties include the Angiopoietins, (Ang-1); Hepatocyte Growth Factor (HGF); Platelet-Derived Growth Factor (PDGF); Insulin-like Growth Factor family (IGF-1, IGF-2) and the Neurotrophins (NGF).

The VEGFs and their corresponding receptors are key regulators in a cascade of molecular and cellular events that ultimately lead to the development of the vascular system, either by vasculogenesis, angiogenesis or in the formation of the lymphatic vascular system. Although VEGF is a critical regulator in physiological angiogenesis, it also plays a significant role in skeletal growth and repair.

In the mature established vasculature, the endothelium plays an important role in the maintenance of homeostasis of the surrounding tissue by providing the communicative network to neighboring tissues to respond to requirements as needed. Furthermore, the vasculature provides growth factors, hormones, cytokines, chemokines and metabolites, and the like, needed by the surrounding tissue and acts as a barrier to limit the movement of molecules and cells. Signals and attractant factors expressed on the bone endothelium help recruit circulating cells, particularly hematopoietic cells, to the bone marrow and coordinate with metastatic cells to target them to skeletal regions. Thus, any alteration in the vascular supply to bone tissue can lead to skeletal pathologies, such as osteonecrosis (bone death caused by reduced blood flow to bones), osteomyelitis (infection of the bone or bone marrow by microorganism), and osteoporosis (loss of bone density). A number of factors have been found to have a prominent effect on the pathology of the vasculature and skeleton, including Osteoprotegerin (OPG), which inhibits Receptor Activator of NF-κB Ligand (RANKL)-induced osteoclastogenic bone resorption.

Intramembraneous and endochondral bone ossification occur in close proximity to vascular ingrowth. In endochondral ossification, the coupling of chondrogenesis and osteogenesis to determine the rate of bone ossification is dependent on the level of vascularization of the growth plate. For example, vascular endothelial growth (VEGF) factor isoforms are essential in coordinating metaphyseal and epiphyseal vascularization, cartilage formation, and ossification during endochondral bone development. HIF-1 stimulates transcription of the VEGF gene (and of other genes whose products are needed when oxygen is in short supply). The VEGF protein is secreted, diffuses through the tissue, and acts on nearby endothelial cells.

The response of the endothelial cells includes at least four components. First, the cells produce proteases to digest their way through the basal lamina of the parent capillary or venule. Second, the endothelial cells migrate toward the source of the signal. Third, the cells proliferate. Fourth, the cells form tubes and differentiate. VEGF acts on endothelial cells selectively to stimulate this entire set of effects. Other growth factors, including some members of the fibroblast growth factor family, also can stimulate angiogenesis, but they influence other cell types besides endothelial cells. As the new vessels form, bringing blood to the tissue, the oxygen concentration rises, HIF-1 activity declines, VEGF production is shut off, and angiogenesis ceases.

The vascularization of cartilage regions in long bones occurs at different stages of development. In early embryonic development, blood vessels that originate from the perichondrium invaginate into the cartilage structures. During elevated postnatal growth, capillaries invade the growth plate of long bones. In adulthood, angiogenesis periodically can be switched on during bone remodeling in response to bone trauma or pathophysiological conditions such as rheumatoid arthritis (RA) and osteoarthritis (OA).

Bone has the unique capacity to regenerate without the development of a fibrous scar, which is symptomatic of soft tissue healing of wounds. This is achieved through the complex interdependent stages of the healing process, which mimic the tightly regulated development of the skeleton. Following trauma with damage to the musculoskeletal system, disruption of the vasculature leads to acute necrosis and hypoxia of the surrounding tissue. This disruption of the circulation leads to the activation of thrombotic factors in a coagulation cascade leading to the formation of a hematoma. The inflammatory response and tissue breakdown activate factors such as cytokines and growth factors that recruit osteoprogenitor and mesenchymal cells to the fracture site. The stimulation of the endosteal circulation in the fractured bone allows mesenchymal cells associated with growing capillaries to invade the wound region from the endosteum and bone marrow. At the edge of a bone fracture, the transiently formed granulation tissue is replaced by fibrocartilage. Concomitantly, the periosteum directly undergoes intramembranous bone formation leading to the formation of an external callus; while internally, the tissue is being mineralized to form woven bone. After stabilization of the bone tissue and vasculature in the bone fracture, the cell mediated remodeling cascade is activated where osteoclastic removal of necrotic bone is followed by the replacement of the large fracture callus by lamellar bone, the callus size is reduced and the normal vascular supply is restored.

A plurality of mediators associated with fetal and postnatal bone development plays a prominent role in the cascade response in bone fracture repair. These include but are not limited to BMP-2 and 4, VEGF, bFGF, TGF-β, and PDGF. VEGF expression is detected on chondroblasts, chondrocytes, osteoprogenitor cells and osteoblasts in the fracture callus where it is highly expressed in angioblasts, osteoprogenitor and osteoblast cells during the first seven days of healing but decreases after eleven days. Additionally, osteoclasts release heparinase that induces the release of the active form of VEGF from heparin, activating not only angiogenesis but also osteoclast recruitment, differentiation and activity leading to the remodeling of the fracture callus during endochondral ossification. Fractures in some cases fail to repair or unite resulting in fibrous filled pseudarthrosis. A number of contributing factors can lead to non-union or delayed union of bone fractures, such as, but not limited to, anti-inflammatory drugs, steroids, Vitamin C, Vitamin D and calcium deficiencies, tobacco smoking, diabetes, and other physiological disorders.

The absence of a functional vascular network is also an important factor in the lack of bone healing in non-union fractures. Studies have reported that angiogenic factors released from biomimetic scaffolds can enhance bone regeneration and that combination strategies that release both angiogenic and osteogenic factors can enhance the regenerative capacity of bone.

The critical sequential timing of osteoclast differentiation and activation, angiogenesis, recruitment of osteoprogenitor cells and the release of growth factors such as BMP-2 in osteogenesis and fracture repair may be enhanced by the synchronized endogenous production of angiogenic and osteogenic mediators. Studies in rat femoral drill-hole injury have shown differential expression of VEGF splicing isoforms along with its receptors, indicating an important role in the bone healing process. Other studies have demonstrated that angiogenesis occurs predominantly before the onset of osteogenesis in bone lengthening in an osteodistraction model.

Another angiogenic inducing growth factor, FGF-2, can accelerate fracture repair when added exogenously to the early healing stage of a bone. Although the mechanism has not been fully elucidated, it has the ability to stimulate angiogenesis and the proliferation and differentiation of osteoblasts to possibly aid the repair of bone fractures.

2.3. Cartilaginous Tissue Compartments

Cartilaginous tissue compartments are specialized connective tissue compartments comprising cartilage cells, known as chondrocytes, cartilage fibers and ground substance constituting the cartilage matrix, that collectively contribute to characteristic elastic firmness rendering cartilage capable of withstanding high levels of pressure or sheer. Cartilage is histologically classified into three types depending on its molecular composition: hyaline cartilage; fibrocartilage and elastic cartilage.

Hyaline cartilage is the predominant form of cartilage comprising an amorphous matrix surrounding chondrocytes embedded within spaces, known as lacunae. Hyaline cartilage, which is commonly associated with the skeletal system and found in the nose, trachea, bronchi and larynx, predominantly functions to provide support. Hyaline cartilage associated with the articular portions of bone, forming the major component of synovial joints, is termed articular cartilage. Hyaline cartilage is usually avascular except where vessels may pass through to supply other tissues and in ossification centers involved in intracartilaginous bone development.

Fibrocartilage, which is commonly found in intervertebral discs and pubic symphysis and functions to provide tensile strength and in shock absorption, is less firm than hyaline cartilage. It comprises a combination of dense collagenous fibers with cartilage cells and a scant cartilage matrix. Fibrocartilage is not usually circumscribed by a perichondrium. Proportions of cells, fibers and ECM components in fribrocartilage are variable.

Elastic cartilage, which is found in the external ear, the Eustachian tube, epiglottis and some of the lanryngeal cartilages, is characterized by a large number of elastic fibers that branch and course in all directions to form a dense network of anastomising and interlacing fibers.

2.3.1. Articular Cartilage Matrix

The chondrocytes in articular cartilage are surrounded by a narrow region of connective tissue ECM, termed the pericellular matrix (PCM), which together with the chondrocyte, is termed chondron. The PCM, which is very rich in fibronectin, proteoglycans (e.g., aggrecan, hyaluron and decorin) and collagen (types II, VI and IX), is particularly characterized by a high concentration of type VI collagen as compared to the surrounding ECM. In normal articular cartilage, type VI collagen is restricted to the chondrons, but in osteoarthritic cartilage, it is upregulated and found throughout the ECM. A proteomic analysis of articular cartilage revealed the presence of collagen α1 (II) C-propeptide, collagen α1 (XI) C-propeptide, collagen α2 (XI) C-propeptide, collagen α1 (VI), collagen α2 (VI), link protein, biglycan, .decorin, osteonectin, matrillin-1, annexin-V, lactadherin, and binding immunoglobulin protein (BiP), in addition to metabolic proteins. (Wilson et. al., 2008, Methods, 48: 22-31).

2.3.2. Chondrocyte Differentiation

The specific structure of articular cartilage, with endogenous chondrocytes forming adult joints, is the result of endochondral ossification, as described above under the Heading, Osseous Tissue Compartments Formation.

Chondrocyte differentiation and maintenance in articular cartilage is governed by interaction of multiple factors. Key players include, but are not limited to, ions (e.g., calcium); steroids (e.g., estrogens); terpenoids (e.g., retinoic acid); peptides (e.g., Parathyroid hormone (PTH), parathyroid hormone-related peptide (PTHrP)), insulin growth factors (e.g., TGFβ hormones, including, without limitation, BMPs, IGF-1, VEGF, PDGF, FGF); transcription factors (e.g., Wnt, SOX-9); eicosanoids (e.g., prostaglandins); catabolic interleukins (e.g., IL-1); and anabolic interleukins (e.g., IL-6, IL-4 and IL-10). (Gaissmaier et al., 2008, Int. J. Care Injured, 39S1: S88-S96).

2.3.3. Growth Plate

The epiphyseal plates or growth plates are a hyaline cartilage plate located in the metaphysis at the end of long bones. Whereas endochondral ossification is responsible for the formation of cartilage in utero and in infants, the growth plates are responsible for the longitudinal growth of long bones via a cartilage template. The ongoing developmental processes of proliferation and differentiation within the growth plates are mediated by a number of hormonal and paracrine factors secreted by the growth plate chondrocytes. The growth plate is a highly organized structure comprising a large number of chondrocytes in various stages of differentiation and proliferation embedded in a scaffold of ECM components.

The growth plate can be subdivided into four zones depending on the stage of differentiation and spatial distribution of collagen types. The resting zone is the smallest zone close to the epiphyseal cartilage comprising small monomorphic chondrocytes with a narrow rim of cytoplasm. The chondrocytes of the resting zone secrete growth plate orienting factor (GPOF) that aligns proliferating cells parallel to the long axis of the developing bone. Stem cell-like cells of the resting zone have a limited proliferative capacity, which eventually leads to fusion of the growth plate (epiphyseal fusion). The proliferative zone of the growth plate comprises chondrocytes that are arranged in characteristic columns parallel to the longitudinal axis of the bone and are separated by ECM with high type II collagen. The chondrocytes of the proliferative zone are mitotically active, have high oxygen and glycogen content, and exhibit increased mitochondrial ATP production. The hypertrophic zone refers to the zone farthest from the resting zone where prehypertrophic chondrocytes stop dividing and terminally differentiate into elongated hypertrophic chondrocytes embedded in ECM high in type X collagen. Hypertrophic chondrocytes have a high intracellular calcium concentration required for the production of release vesicles containing Ca2+-binding annexins, that secrete calcium phosphate, hydroxyapatite, phosphatases (such as alkaline phosphatase), metalloproteinases, all instrumental in proteolytic remodeling and mineralization of the surrounding matrix. The hypertrophic chondrocytes produce factors, such as VEGF, that initiate vascularization of the mineralized matrix that is then degraded by invading phagocytic chondroclasts and osteoclasts constituting the invading zone.

The developmental processes involving chondrogenesis are regulated by an interplay of a large number of systemic hormones and paracrine factors, including growth factors, cytokines and transcription factors. Key factors involved in chondrocyte proliferation and differentiation in the growth plate including ATF-2, BCL-2, Inn, PTHrP, BMP, PGE2, MMP, Sox, Runx2 (Cbfa1), NOTCH, HOX, FGF are reported by Brochhausen et al. (J. Tissue Eng. Regen. Med. 2009, 3: 416-429).

2.3.4. Stem Cells of Cartilaginous Tissue Compartments

Multipotent mesenchymal progenitor cells with adipogenic, osteogenic and chondrogenic potential, and that are CD105+/CD166+ (corresponding to TGF-β type III receptor (endoglin) and ALCAM, respectively), have been identified in articular cartilage. (Asalameh et al., Arthritis & Rheumatism, 2004, 50(5): 1522-1532). The presence of CD34−/CD45−/CD44+/CD73+/CD90+ mesenchymal stem cells with adipogenic, chondrogenic and osteogenic potential also has been shown. (Peng et al., Stem Cells and Development (2008), 17: 761-774). Similar to bone-derived MSCs, articular-derived MSCs are positive for surface expression of Notch-1. (Hiraoka et al., Biorheology, 2006, 43: 447-454). A potential MSC niche positive for Stro-1, Jagged-1 and BMPr1a has also been identified in the perichondrial zone of Ranvier on the growth plate. (Karlsson et al., 2009, J. Anat. 215(3): 355-63).

Differential expression of Notch-1, Stro-1 and VCAM-1/CD106 markers has been observed in normal articular cartilage versus osteoarthritic (OA) cartilage. In normal cartilage, expression of these markers is higher in the superficial zone (SZ) as compared to the middle zone (MZ) and deep zone (DZ). On the other hand, OA cartilage SZ has reduced Notch-1 and Sox-9 while MZ has increased Notch-1, Stro-1 and VCAM-1 positive cells. (Grogan et al., Arthritis Res. Ther. 2009, 11(3): R85-R97).

2.3.5. Intervertebral Disc Fibrocartilage Tissue Compartments

The intervertebral discs (IVD) predominantly are comprised of fibrocartilage. The IVD fibrocartilage is continuous both with and below the articular cartilage of adjacent vertebrae as well as peripherally with spinal ligaments. The IVD is a unique structure containing annulus fibrosus (AF) and nucleus pulposus (NP), a gelatinous ellipsoidal remnant of the embryonic notochord, and is sandwiched between two adjacent cartilaginous endplates (EP). IVD rupture and herniation of the nucleus pulposus into the spinal cord may cause severe pain and other neurological symptoms. The NP and AF synergistically function to achieve the primary role of IVD in transferring load, dissipating energy and facilitating in joint mobility.

The adult IVD is essentially avascular; hence, endogenous cells survive in a low-nutrient and low-oxygen microenvironment. The major ECM components of IVD include but are not limited to aggrecan, collagen (e.g., types I, II and IX), leucine rich repeat (LRR) proteins and proteoglycans (e.g., fibromodulin, decorin, lumican), cartilage oligomatrix protein, and collagen VI beaded filament network. (Feng et al., 2006, J. Bone Joint Surg. Am. 88: 25-29). The water content, GAG content, aggrecan levels and levels of type II collagen are significantly lower in older discs demonstrating the effects of IVD degeneration with age. (Murakami et al., 2010, Med. Biol. Eng. Comput. 48: 469-474).

The central nucleus pulposus (NP) is rich in aggrecan and hyaluron. The developing NP is characterized by the presence of highly vacuolated chondrocytes and small chondroblasts inherited from the notochord. Primarily functioning as a primitive axial support, the integrity of the notochord is maintained by a proteoglycan (PG-) and laminin-rich sheath. As NP matures, the cellular composition becomes predominantly chondrocytic. Mature NP cells are small and have an aggrecan rich matrix, which is essential in maintaining requisite hydration levels for mechanical function. Their gene expression profile and metabolic activity are distinct from the chondrocytes of articular cartilage. The ECM of immature NP has high aggrecan levels and primarily contains type II collagen, with the type IIA isoform expressed by progenitor cells during chondrogenesis, not by mature chondrocytes. (Hsieh A. H. and Tworney J. D., J. Biomech., 2010, 43(1): 137-156).

The AF surrounds the NP with layers of unidirectional sheets of collagen parallel to the circumference of a disc to form collagen lamellae. Alternating bidirectional collagen fibers intersperse the AF collagen lamellae. AF can be subdivided into three regions: inner AF, middle AF and outer AF. The inner AF arises along with endochondral formation of the vertebrae. The outer AF arises as a separate cell condensation with slower matrix formation. Lamellae of inner AF comprises predominantly of type II collagen and fibrochondrocytes, while those of outer AF are comprised of type I collagen and fibroblasts. A population of pancake shaped interlamellar cells as well as elastin fibers are also found within the lamellae, in vertebral attachments, and at the NP-AF interface. Large proteoglycans (PGs; for example aggrecan and versican) and type I and VI collagen permeate interlamellar and translamellar ECM. (Hsieh A. H. and Tworney J. D., J. Biomech., 2010, 43(1): 137-156).

A large number of coordinated signals originating from the cells of the notochord and floor plate of the embryonal neural tube are instrumental in disc embryogenesis. Key signals include, but are not limited to, sonic hedgehog (Shh), Wnt, noggin, Pax family of transcription factors (e.g., Pax 1 and Pax 9), Sox family of transcription factors (Sox5, Sox6 and Sox) and TGF-β. (Smith et al., 2011, Dis Model Mech. 4(1): 31-41). Herniation and IVD degeneration are associated with changes in inflammatory and immune cytokine profiles, including, but not limited to, the activation of Th1-related cytokines (e.g. IFNγ) as well as Th17-related cytokines (e.g., IL-4, IL-6, IL-12 and IL-17). (Shamji et al., 2010, Arthritis & Rheumatism, 62(7): 1974-1982).

A potential stem cell niche comprised of progenitor cells that are positive for Notch1, Delta4, Jagged1, CD117, Stro-1 and Ki67 has been identified in intervertebral discs of a number of animals, including humans. It has been reported that the IVD tissue compartments comprise a slow growing zone in the AF as well as the NP regions. (Henriksson et al., 2009, SPINE, 34(21): 2278-2287).

2.4. Cardiovascular Tissue

Cardiovascular tissues can include the tissue that comprises any organ involved in the cardiovascular function of an organism. The cardio vascular system permits blood to circulate and transport nutrients (such as amino acids and electrolytes), oxygen, carbon dioxide, hormones, and blood cells to and from the cells in the body to provide nourishment and help in fighting diseases, stabilize temperature and pH, and maintain homeostasis. Tissues of the cardiovascular system can include arteries, capillaries, veins, coronary vessels, portal veins, and the heart, including all of its associated structures. Other types of cardiac tissue can include connective tissue, and cardiac muscle. Cardiac muscle is comprised of the epicardium, myocardium, and endocardium. The epicardium is the outer layer of cardiac muscle. The myocardium is the thick middle layer of cardiac muscle. The endocardium is the inner most portion of cardiac muscle.

2.5. Cornea Tissue

Cornea tissue refers to the transparent front facing structure of the eye, which cover the iris, pupil, and anterior chamber. The cornea refracts light with the anterior chamber and the lens and is responsible for the optical power of the eye. The human cornea has five layers including the corneal epithelium, anterior limiting membrane (Bowman's layer), substantia propria (Corneal stroma), posterior limiting membrane (Descemet's membrane), and the Corneal endothelium.

2.6. Dental Tissue Compartments

A tooth has three anatomical divisions (crown, root and neck), and four structural components (enamel, dentin, cementum and pulp).

Enamel is the hardest, most mineralized biological tissue in the human body. It is composed of elongated hydroxyapatite crystallites bundled into rods or prisms, interspersed with crystalline interrods filling the interstitial space.

Enamel cells, known as ameloblasts, are responsible for enamel development. Ameloblastin, TRAP and enamelin are key proteins found in enamel tissue whereas the enamel matrix is devoid of collagen, composed primarily of amelogenin. An intricate orchestration of signaling factors, such as BMPs (e.g., BMP-2, BMP-4, BMP-7), FGFs (e.g., FGF-3, -4, -9, -20), Wnt-3, 10a, 10b and transcription factors, such as, p21, Msx2 and Lef1 is responsible for morphogenesis of enamel. Self-assembly of amelogens to form amelogenin nanospheres play a role in nucleation of hydroxyapatite crystallization and enamel mineralization. Matrix processing enzymes, such as MMP-20, kallikrein-4 (KLK4), also known as enamel matrix serine protease-1 (EMSP-1), are involved in the complete elimination of the protein matrix and replacement with a mineralized matrix. (Fong et al., 2005, J. Dent. Educ., 69(5): 555-570). Ameloblasts arise from epithelial stem cells of ectodermal origin. They are lost after tooth eruption leaving no adult human ectodermal stem cells in the mature enamel. In contrast, rodent enamel retain a niche of epithelial stem cells, known as apical bud cells, for continuous enamel production. (Ulmer et al., 2010, Schweiz Monatsschr Zahnmed, 120:860-872).

Dentin is a hard, yellowish and elastic living connective tissue compartment with biomechanical properties similar to bone. The formation of dentin is driven by mesenchymally derived mature odontoblasts that are fully differentiated and nondividing and that form a single layer underneath the dentin in a mature tooth. A series of epithelial-mesenchymal interactions regulates odontoblast differentiation from neural crest cells in the first branchial arch and frontonasal processes. Mature dentin is comprised of a mantle, composed of intertubular and peritubular dentin made of a collagen fibril matrix, with odontoblast cell processes extending into dentin tubules. During dentinogenesis, odontoblasts secrete predentin, a mineralized tissue composed of type I collagen. Unlike osteogenesis, in dentinogenesis, as the predentin layer is formed, the odontoblasts recede instead of becoming embedded within the dentin matrix, leaving behind cells processes within dentinal tubules. Subsequently, the unmineralized predentin is converted to dentin by gradual mineralization of collagen. Dentinogenesis is directed by a series of highly controlled biochemical events that control the rates of collagen secretion, its maturation into thick fibrils, loss of proteoglycans, mineral formation including hydroxy apatite crystallization, and growth. The dentin matrix is primarily composed of collagens (e.g., types I, III and V) as well as other matrix proteins, including, but not limited to, phosphorylated and nonphosphorylated matrix proteins, proteoglycans, growth factors, metalloproteinases, alkaline phosphatase serum derived proteins, and phospholipids. (Fong et al., 2005, J. Dent. Educ., 69(5): 555-570). No stem cells have been identified in mature dentin.

The dental pulp is the tooth's living tissue that respond to pain and damage and initiates tissue repair. An odontoblast cell layer forms the outer boundary of the pulp and is associated with an underlying network of dendritic cells. A cell-free zone underlying the odontoblast layer is rich in nerve fibers and blood vessels. Similar to dentin, dental pulp also differentiates from neural crest-derived ectomesenchyme during tooth development.

Several sources of stem cells have been identified associated with pulp tissue. In immature teeth, apical papilla, the embryonal organ responsible for pulp differentiation, is the source for stem cells of apical papilla (SCAP). Mature dental pulp is the source of dental pulp stem cells (DPSC) whereas stem cells are also extracted from exfoliated deciduous teeth (SHED) Additional cells of the dental pulp core that function in pulpal defense, include, but are not limited to, macrophages, lymphocytes and mast cells. Pulp matrix is composed of collagens (e.g., types I, III V and VI), but lacks mineralization. Other noncollagenous proteins of the pulp matrix are similar in composition to dentin. The dental pulp is capable of responding to dentin tissue damage by secreting new dentin from old odontoblast populations or generation and secretion of dentin from new secondary odontoblast populations. (Fong et al., 2005, J. Dent. Educ., 69(5): 555-570).

The periodontium consists of tissues supporting the tooth crown, including a nonmineralized periodontal ligament (PDL) sandwiched between layers of mineralized tissues, including the cementum, alveolar bone and dentin. Cementum is a thin mineralized layer covering the dentin. Cementoblasts are cells responsible for cementum matrix secretion and subsequent mineralization. When cementoblasts become entrapped within cementum matrix, they are termed cementocytes. Cementoblasts are ectomesenchymal, being derived from neural crest cells, similar to PDL and alveolar bone. Like bone and dentin, cementum is a collagenous mineralized tissue that hardens upon formation of carbonated hydroxyapatite. (Fong et al., 2005, J. Dent. Educ., 69(5): 555-570).

PDL is a space between cementum and alveolar bone. It represents a replacement of the dental follicle region in immature developing teeth. Mature PDL contains mostly periodontal fibroblasts as well as stem cells, known as the periodontal ligament stem cells (PDLSCs). The immature dental follicle is also a source of mesenchymal stem cells, known as dental follicle stem cells (DFSCs). (Fong et al., 2005, J. Dent. Educ., 69(5): 555-570). The differentiation potential of dental mesenchymal cells has been reviewed by Ulmer et al., Zahnmed, 2010, Schweiz Monatsschr 120:860-872 and is incorporated herein by reference in its entirety.

Several dental stem cell markers have been identified. Stro-1 and Stro-4 are commonly used dental stem cell markers for all dental mesenchymal stem cells. Dental stem cells originating from the neural crest have the neural marker, nestin. An osteoblast marker, osteocalcin, is also used as a stem cell marker for DPSCs. Similarly, SCAPs express Oct-4, Nanog, SSEA-3, SSEA-4, TRA-1-60 and TRA-1-81. (Ulmer et al., 2010, Schweiz Monatsschr Zahnmed, 120:860-872).

2.7. Fascial Tissue Compartment

Fascial tissue compartments form a layer of fibrous tissue found throughout the body surrounding softer and more delicate organs, including but not limited to muscles, groups of muscles, blood vessels, nerves, etc. Fascial tissue originates from the embryonic mesenchyme. Fasciae form during the development of bones, muscles and vessels from the mesodermal layer of the embryo. Fascial tissue can be categorized into three types depending on location: (1) superficial fascial tissue, which is found beneath the integument throughout the body, usually blending with the reticular layer of the dermis; (2) deep fascial tissue comprising dense fibroareolar connective tissue surrounding muscles, bones, nerves and blood vessels; and (3) visceral or subserous fascia, which suspends organs within their cavities and wraps them in layers of connective tissue membranes. (Chapter IV. Myology, Section 3. Tendons, Aponeuroses, and Fasciae, Gray's Anatomy of the Human Body, 20th Edition, Re-edited by Lewis, W. H., Lea & Febiger, Philadelphia, 1918, Bartleby.com, New York, 2000).

The fibroareolar connective tissue of fascia comprises four kinds of cells: (1) flattened lamellar cells, which may be branched or unbranched (branched lamellar cells contain clear cytoplasm and oval nuclei and project multidirectional processes that may unite to form an open network, such as in the cornea; unbranched lamellar cells are joined end to end. (2) Clasmatocytes, which are large irregular vacuolated or granulated cells with oval nuclei. (3) Granule cells, which are ovoid or spherical in shape. (4) Plasma cells of Waldeyer, usually spheroidal, characterized by vacuolated protoplasm.

2.8. Hair Follicles

Hair follicles are the mammalian skin organ responsible for the production of hair. Hair follicles are comprised of several structures including the papilla, matrix, root sheath, bulge, and other supporting structures including the fundibulum, the arrector pili muscles, the sebaceous glands, and the apocrine sweat glands. Hair follicle receptors sense the position of the hair. The papilla is a large structure situated at the base of the hair follicle, made up of mainly of connective tissue, and a capillary loop. The area surround the papilla is defined by hair matrix. The root sheath is composed of two portions: an external and internal root sheath. The external root sheath appears empty with cuboid cells. The internal root sheath is composed of three layers, Henle's layer, Huxley's layer, and an internal cuticle, which is continuous with the outermost layer of the hair fiber.

2.9. Ligament Tissue Compartment

The term "ligaments" as used herein refers to dense regular connective tissue comprising attenuated collagenous fibers that connect bones at joints. Ligament ECM is composed of type I and type III collagens together with other proteoglycans and glycoproteins. Mesenchymal stem cells have been found in the human anterior cruciate ligament that exhibit multilineage differentiation potential, like bone-derived mesenchymal stem cells. (Cheng et al., 2010, Tissue Eng. A, 16(7):2237-2253).

2.10. Meniscus

The meniscus is comprised of two pads or menisci comprised of fibrocartilaginous tissue which serve to disperse friction in the knee joint between the tibia (lower leg) and femur (the thigh). The menisci are concave on the top portion and flat on the bottom portion, articulating with the tibia. The menisci are attached to the fossae (small depressions) between the condyles of the tibia (intercondyloid fossa), and towards the center they are unattached and their shape narrows to a thin shelf. The menisci act to disperse the weight of a body and reduce friction during movement.

2.11. Reproductive Tissue and Foreskin

The reproductive tissues can include the tissues that comprise any organ involved in the reproductive process of an organism. Vertebrate animals all share the key elements of their reproductive systems, including gamete producing organs or gonads, which can be broken down to male and female counterparts.

The major reproductive organs of the male can be grouped into three categories. 1. Sperm production and storage. Production takes place in the testes which are housed in the temperature regulating scrotum, immature sperm then travel to the epididymis for development and storage. 2. Ejaculatory fluid producing glands which include the seminal vesicles, prostate, and the vas deferens. 3. Organs used for copulation, and deposition of the spermatozoa (sperm) within the male, these include the penis, urethra, vas deferens, and Cowper's gland. The foreskin is a double-layered fold of smooth muscle tissue, blood vessels, neurons, skin, and mucous membrane that covers and protects the glans penis and the urinary meatus. The foreskin can also be described as the prepuce, a technically broader term that also includes the clitoral hood in women, to which the foreskin is embryonically homologous.

The male reproductive system can include the following structures. The testes can include: Tunica vaginalis, Tunica albuginea, Tunica vasculosa, Appendix Mediastinum, Lobules Sept, Leydig cells, and Sertoli cells. Internal structures critical to the function of the male reproductive system can include: Seminiferous tubules (e.g., Tubuli seminiferi recti, Rete testis, Efferent ducts), Epididymis- (e.g., Appendix and Stereocilia), Paradidymis Spermatic cord, Vas deferens Ampulla, and Ejaculatory duct. Accessory glands of the male reproductive system can include: Seminal vesicles (e.g., excretory duct), Prostate (e.g., Urethral crest), Seminal colliculus, Prostatic utricle, Ejaculatory duct, Prostatic sinus, Prostatic ducts, and Bulbourethral glands. The penis can include the following structures: root (e.g., Crus Bulb, Fundiform ligament, Suspensory ligament), body (e.g., Corpus cavernosum, Corpus spongiosum), glans (e.g., Foreskin, Frenulum Corona), fascia (e.g., superficial deep), Tunica albuginea, and Septum. The urinary tract can include: Internal urethral orifice, Urethra (e.g., Prostatic, Intermediate, Spongy), Navicular fossa, External urethral orifice, Lacunae of Morgagni, and Urethral gland. The scrotum can include the skin layers (e.g., Dartos, External spermatic fascia, Cremaster, Cremasteric fascia, Internal spermatic fascia), Perineal raphe and Scrotal septum.

The human female reproductive system is a series of organs primarily located inside of the body and around the pelvic region of a female that contribute towards the reproductive process. The human female reproductive system contains three main parts: the vagina, which leads from the vulva, the vaginal opening, to the uterus; the uterus, which holds the developing fetus; and the ovaries, which produce the female's ova. The breasts are involved during the parenting stage of reproduction, but in most classifications they are not considered to be part of the female reproductive system. The vagina meets the outside at the vulva, which also includes the labia, clitoris and urethra; during intercourse this area is lubricated by mucus secreted by the Bartholin's glands. The vagina is attached to the uterus through the cervix, while the uterus is attached to the ovaries via the fallopian tubes. Each ovary contains hundreds of egg cells.

The female reproductive system can include the following structures. The ovaries can include the: corpus (e.g., hemorrhagicum, luteum, albicans), Theca of follicle (e.g., externa and interna), Follicular antrum, Follicular fluid, Corona radiata, Zona pellucida, Membrana granulosa, Perivitelline space, Germinal epithelium, Tunica albuginea, cortex (e.g., Cumulus oophorus and Stroma), and Medulla. The fallopian tubes can include the: Isthmus, Ampulla, Infundibulum, Fimbria, and Ostium. Ovary ligaments can include the: Proper of ovary and Suspensory of ovary. Wolffian vestiges can include the: Gartner's duct, Epoophoron, (e.g., Vesicular appendages of epoophoron) and Paroophoron.

The uterus can include the following regions: corpus/body (e.g., Uterine cavity, Fundus), Cervix (e.g., External orifice, Canal, Internal orifice, Supravaginal portion, Vaginal portion), and Uterine horns. The uterus layers can include the: Endometrium, Myometrium, Perimetrium and Parametrium. The uterus can include glands, for example, the utuerine gland. The uterus can include ligaments including the: Round ligament, Broad ligament, Cardinal ligament, Uterosacral ligament and Pubocervical ligament. The vagina can include the: Fossa of vestibule of vagina, vaginal fornix and Hymen. The labia can include the: Mons pubis, Labia majora (e.g., Anterior commissure and Posterior commissure), Pudendal cleft, Labia minora (e.g., Frenulum of labia minora and Frenulum of clitoris), Vulval vestibule, Interlabial sulci, Bulb of vestibule, Vaginal orifice, vestibular glands/ducts (e.g., Bartholin's glands/Bartholin's ducts, Skene's glands/Skene's ducts). The clitoris can include the: Crus of clitoris, Corpus cavernosum, clitoral glans, Hood. The urethra can include the urethral crest. Other female reproductive structures can include the: Grafenberg spot, Urethral sponge and Perineal sponge.

2.12. Spinal Disc

Spinal disc can otherwise be known as intervertebral disc or the intervertebral fibrocartilage. The term spinal disc refers to tissue which lies between adjacent vertebrae in the vertebral column. Each spinal disc forms a fibrocartilaginous joint, thereby allowing movement of the vertebrae. Spinal discs also act as a ligament to hold the vertebrae together. Spinal disc role as shock absorbers in the spine is crucial.

Spinal disc consist of an outer fibrous ring, (e.g., the anulus fibrosus), which surrounds an inner gel-like center (e.g., the nucleus pulposus). The anulus fibrosus consists of several layers or laminae of fibrocartilage, made up of both type I and type II collagen. Type I collagen is concentrated towards the edge of the ring where it provides greater strength. The stiff laminae can withstand compressive forces. The fibrous intervertebral disc contains the nucleus pulposus, which assist in the distribute pressure evenly across the disc, preventing the development of stress concentrations which could cause damage to the underlying vertebrae or to their endplates. The nucleus pulposus contains loose fibers that are suspended in a mucoprotein gel. The nucleus pulposus acts as a shock absorber, absorbing the impact of the body's activities and keeping the two vertebrae separated.

2.13. Synovial Tissue Compartment

The synovial membrane is composed of fibrous connective tissue and lines the joint cavity of synovial joints. It is made up of a layer of macrophage (type A) and fibroblast-like (type B) synoviocytes and a loose sublining tissue. Synovial fluid is secreted by synovial cells lining the synovial membrane in the joint capsule. It is a viscid, mucoalbuminous fluid, rich in hyaluronic acid. It acts as a lubricating fluid, facilitating the smooth gliding of the articular surface. Functional mesenchymal stem cell niches have been identified as resident to synovial lining and subsynovial tissue. These cells are positive for the artificial nucleoside, iododeoxyuridine (IdU) as well as MSC markers such as PDGFRα, p75 and CD44 and have chondrogenic potential. (Kurth et al., Arthritis Rheum., 2011, 63(5): 1289-1300). Synovial fluid-derived MSCs have also been identified, and these have higher chondrogenic potential as compared to bone marrow-derived and adipogenic MSCs. (Koga et al., 2008, Cell Tissue Res., 333: 207-215). Synovial MSCs and MPCs have been shown to prevent degeneration due to intervertebral disc disease (IVD) and to be useful for cartilage tissue engineering. (Miyamoto et al., 2010, Arthritis Res. Ther., 12: R206-218; Lee et al., 2010, Tissue Eng. A, 16(1): 317-325).

2.14. Tendon Tissue Compartment

Tendons are specialized connective tissue compartments that connect bone to muscle. Tendon cells are embedded amongst a parallel group of collagenous fibers that secrete a unique ECM containing collagens, large proteoglycans, and small leucine rich proteoglycans that function as lubricators and organizers of collagen fibril assembly. A unique tendon stem/progenitor cell (TSPC) niche has been identified amongst the parallel collagen fibrils surrounded by ECM. The TSPCs exhibit osteogenic and adipogenic potential. Biglycan and fibromodulin are key tendon ECM components that direct TSPC fate through BMP signaling. These TSPCs are positive for bone marrow derived stem cell markers such as Stro-1, CD146, CD90 and CD44 but not for CD18. TSPCs do not express hematopoietic markers, such as CD34, CD45 and CD117, or the endothelial marker CD106. (Bi et al., 2007, Nat. Med., 13(10): 1219-1227).

2.15. Vasculature Tissue Compartment

The vascular wall is made of three concentric zones with distinct cellular composition, all mesodermal in origin: the tunica intima, containing predominantly mature differentiated endothelial cells (EC), the tunica media, containing mature and differentiated smooth muscle cells, and the tunica adventitia, containing mature fibroblasts. (Tilki et al., 2009, Trends Mol. Med. 15(11): 501-509). Endothelial progenitor cells (EPCs), meaning cells that exhibit clonal expression, stemness characteristics, adherence to matrix molecules and an ability to differentiate into endothelial cells (ECs) have been implicated in the formation of new blood vessels through angiogenesis and postnatal vasculogenesis. EPCs have many characteristic cell surface markers, including, but not limited to, CD34, AC133, KDR (VEGFR-2), Tie-2 and ligand for UEA-1 lectin. (Tilki et al., 2009, Trends Mol. Med. 15(11): 501-509; Melero-Martin and Dudley, 2011, Stem Cells, 29: 163-168; Pascilli et al., 2008, Exp. Cell Res., 315: 901-914).

EPC niches have been identified in the bone-marrow, peripheral cord blood and vascular wall matrix. Bone-marrow derived and cord blood EPCs essentially may be proangiogenic hematopoietic progenitor cells (HPCs), circulating in the blood and committed to myeloid lineage. (Tilki et al., 2009, Trends Mol. Med. 15(11): 501-509). The vascular wall stem and progenitor cells (VW-EPCs) reside in distinct zones of the vessel wall within subendothelial space, known as avasculogenic zone, within the vascular adventitia, forming vascular wall-specific niches. Fetal and adult arterial and venous blood vessel walls have also been found to harbor resident niches for a variety of stem and progenitor cells, such as EPCs, smooth muscle progenitors, HSCs, MSCs, mesangial cells coexpressing myogenic and endothelial markers, neural stem cells (NSCs), etc. (Tilki et al., 2009, Trends Mol. Med. 15(11): 501-509). The VW-EPCs are CD34(+)VEGFR-2(+)Tie-2(+)CD31(−)CD144(−). Proliferating and differentiating VW-EPCs become CD144(+).

During embryogenesis, there is evidence of the existence of a hemangioblast (giving rise to endothelial and hematopoietic cells) and hemogenic endothelium, originating from precursors resident in the vascular wall. However, whether adult VW also contains ancestral progenitor hemangioblasts giving rise to both VW-EPCs as well as VW-HSCs is not known. Vascular wall also contains resident pericyte-like cells in the subendothelial spaces. These pericyte-like cells serve as a cellular reservoir for VW-MSCs, which can differentiate into colonies with adipogenic, osteogenic and chondrogenic markers. (Tilki et al., 2009, Trends Mol. Med. 15(11): 501-509).

Exemplary factors secreted by vascular tissue cells are disclosed in Tilki et al., 2009, Trends Mol. Med. 15(11): 501-509, the entire contents of which are incorporated herein by reference.

2.16. Placenta

The placenta is considered one of the most important sources of stem cells, and has been studied extensively. It fulfills two main desiderata of cell therapy: a source of a high as possible number of cells and the use of non-invasive methods for their harvesting. Their high immunological tolerance supports their use as an adequate source in cell therapy (Mihu, C. et al., 2008, Romanian Journal of Morphology and Embryology, 2008, 49(4):441-446).

The fetal adnexa is composed of the placenta, fetal membranes, and umbilical cord. The term placenta is discoid in shape with a diameter of 15-20 cm and a thickness of 2-3 cm. The fetal membranes, amnion and chorion, which enclose the fetus in the amniotic cavity, and the endometrial decidua extend from the margins of the chorionic disc. The chorionic plate is a multilayered structure that faces the amniotic cavity. It consists of the following structures: the amniotic membrane (composed of epithelium, compact layer, and amniotic mesoderm), the chorion (composed of mesenchyme and a region of extravillous proliferating trophoblast cells interposed in varying amounts of Langhans fibrinoid, either covered or not by syncytiotrophoblast), and the intermediate spongy layer between the amniotic membrane and the chorion.

Villi originate from the chorionic plate and anchor the placenta through the trophoblast of the basal plate and maternal endometrium. From the maternal side, protrusions of the basal plate within the chorionic villi produce the placental septa, which divide the parenchyma into irregular cotyledons (Parolini, O. et al., 2008, Stem Cell, 2008, 26:300-311).

Some villi anchor the placenta to the basal plate, whereas others terminate freely in the intervillous space. Chorionic villi present with different functions and structure. In the term placenta, the stem villi show an inner core of fetal vessels with a distinct muscular wall and connective tissue consisting of fibroblasts, myofibroblasts, and dispersed tissue macrophages (Hofbauer cells). Mature intermediate villi and term villi are composed of capillary vessels and thin mesenchyme. A basement membrane separates the stromal core from an uninterrupted multinucleated layer, called the syncytiotrophoblast. Between the syncytiotrophoblast and its basement membrane are single or aggregated Langhans cytotrophoblastic cells, commonly called cytotrophoblast cells (Parolini, O. et al., 2008, Stem Cell, 2008, 26:300-311).

Four regions of fetal placenta can be distinguished: an amniotic epithelial region, an amniotic mesenchymal region, a chorionic mesenchymal region, and a chorionic trophoblastic region.

2.17. Amnion and Chorion 2.17.1. Amniotic Membrane

Fetal membranes continue from the edge of the placenta and enclose the amniotic fluid and the fetus. The amnion is a thin, avascular membrane composed of an inner epithelial layer and an outer layer of connective tissue that, and is contiguous, over the umbilical cord, with the fetal skin. The amniotic epithelium (AE) is an uninterrupted, single layer of flat, cuboidal and columnar epithelial cells in contact with amniotic fluid. It is attached to a distinct basal lamina that is, in turn, connected to the amniotic mesoderm (AM). In the amniotic mesoderm closest to the epithelium, an acellular compact layer is distinguishable, composed of collagens I and III and fibronectin. Deeper in the AM, a network of dispersed fibroblast-like mesenchymal cells and rare macrophages are observed. It has been reported that the mesenchymal layer of amnion indeed contains two subfractions, one having a mesenchymal phenotype, also known as amniotic mesenchymal stromal cells, and the second containing monocyte-like cells.

2.17.2. Chorionic Membrane

A spongy layer of loosely arranged collagen fibers separates the amniotic and chorionic mesoderm. The chorionic membrane (chorion leave) consists of mesodermal and trophoblastic regions. Chorionic and amniotic mesoderm are similar in composition. A large and incomplete basal lamina separates the chorionic mesoderm from the extravillous trophoblast cells. The latter, similar to trophoblast cells present in the basal plate, are dispersed within the fibrinoid layer and express immunohistochemical markers of proliferation. The Langhans fibrinoid layer usually increases during pregnancy and is composed of two different types of fibrinoid: a matrix type on the inner side (more compact) and a fibrin type on the outer side (more reticulate). At the edge of the placenta and in the basal plate, the trophoblast interdigitates extensively with the decidua (Cunningham, F. et al., The placenta and fetal membranes, Williams Obstetrics, 20th ed. Appleton and Lange, 1997, 95-125; Benirschke, K. and Kaufmann, P. Pathology of the human placenta. New York, Springer-Verlag, 2000, 42-46, 116, 281-297).

2.17.3. Amnion-Derived Stem Cells

The amniotic membrane itself contains multipotent cells that are able to differentiate in the various layers. Studies have reported their potential in neural and glial cells, cardiac repair and also hepatocyte cells. Studies have shown that human amniotic epithelial cells express stem cell markers and have the ability to differentiate toward all three germ layers. These properties, the ease of isolation of the cells, and the availability of placenta, make amniotic membrane a useful and noncontroversial source of cells for transplantation and regenerative medicine.

Amniotic epithelial cells can be isolated from the amniotic membrane by several methods that are known in the art. According to one such method, the amniotic membrane is stripped from the underlying chorion and digested with trypsin or other digestive enzymes. The isolated cells readily attach to plastic or basement membrane-coated culture dishes. Culture is established commonly in a simple medium such as Dulbecco's Modified Eagle's Medium (DMEM) supplemented with 5%-10% serum and epidermal growth factor (EGF), in which the cells proliferate robustly and display typical cuboidal epithelial morphology. Normally, 2-6 passages are possible before proliferation ceases. Amniotic epithelial cells do not proliferate well at low densities.

Amniotic membrane contains epithelial cells with different surface markers, suggesting some heterogeneity of phenotype. Immediately after isolation, human amniotic epithelial cells express very low levels of human leukocyte antigen (HLA)-A, B, C; however, by passage 2, significant levels are observed. Additional cell surface antigens on human amniotic epithelial cells include, but are not limited to, ATP-binding cassette transporter G2 (ABCG2/BCRP), CD9, CD24, E-cadherin, integrins $\alpha 6$ and $\beta 1$, c-met (hepatocyte growth factor receptor), stage-specific embryonic antigens (SSEAs) 3 and 4, and tumor rejection antigens 1-60 and 1-81. Surface markers thought to be absent on human amniotic epithelial cells include SSEA-1, CD34, and CD133, whereas other markers, such as CD117 (c-kit) and CCR4 (CC chemokine receptor), are either negative or may be expressed on some cells at very low levels. Although initial cell isolates express very low levels of CD90 (Thy-1), the expression of this antigen increases rapidly in culture (Miki, T. et al., Stem Cells, 2005, 23: 1549-1559; Miki, T. et al., Stem Cells, 2006, 2: 133-142).

In addition to surface markers, human amniotic epithelial cells express molecular markers of pluripotent stem cells, including octamer-binding protein 4 (OCT-4) SRY-related HMG-box gene 2 (SOX-2), and Nanog (Miki, T. et al., Stem Cells, 2005, 23: 1549-1559). Previous studies also have shown that human amnion cells in xenogeneic, chimeric aggregates, which contain mouse embryonic stem cells, can differentiate into all three germ layers and that cultured human amniotic epithelial cells express neural and glial markers, and can synthesize and release acetylcholine, cateholamines, and dopamine. Hepatic differentiation of human amniotic epithelial cells also has been reported. Studies have reported that cultured human amniotic epithelial cells produce albumin and α-fetroprotein and that albumin and α-fetroprotein-positive hepatocyte-like cells could be identified integrated into hepatic parenchyma following transplantation of human amniotic epithelial cells into the livers of severe combined inmmunodeficiency (SCID) mice. The hepatic potential of human amniotic epithelial cells was confirmed and extended, whereby in addition to albumin and α-fetroprotein production, other hepatic functions, such as glycogen storage and expression of liver-enriched transcription factors, such as hepatocyte nuclear factor (HNF) 3γ and HNF4α, CCAAT/enhancer-binding protein (CEBP α and β), and several of the drug metabolizing genes (cytochrome P450) were demonstrated. The wide range of hepatic genes and functions identified in human amniotic epithelial cells has suggested that these cells may be useful for liver-directed cell therapy (Parolini, O. et al., 2008, Stem Cell, 2008, 26:300-311).

Differentiation of human amniotic epithelial cells to another endodermal tissue, pancreas, also has been reported. For example, it was shown that human amniotic epithelial cells cultured for 2-4 weeks in the presence of nicotinamide to induce pancreatic differentiation, expressed insulin. Subsequent transplantation of the insulin-expressing human amniotic epithelial cells corrected the hyperglycemia of streptozotocin-induced diabetic mice. In the same setting, human amniotic mesenchymal stromal cells were ineffective, suggesting that human amniotic epithelial cells, but not human amniotic mesenchymal stromal cells, were capable of acquiring β-cell fate (Parolini, O. et al., 2008, Stem Cell, 2008, 26:300-311).

2.17.4. Mesenchymal Stromal Cells from Amnion and Chorion: hAMSC and hCMSC

Human amniotic mesenchymal cells (hAMSC) and human chorionic mesenchymal cells (hCMSC) are thought to be derived from extraembryonic mesoderm. hAMSC and hCMSC can be isolated from first-, second-, and third-trimester mesoderm of amnion and chorion, respectively. For hAMSC, isolations are usually performed with term amnion dissected from the deflected part of the fetal membranes to minimize the presence of maternal cells. For example, homogenous hAMSC populations can be obtained by a two-step procedure, whereby: minced amnion tissue is treated with trypsin to remove hAEC and the remaining mesenchymal cells are then released by digestion (e.g., with collagenase or collagenase and DNase). The yield from term amnion is about 1 million hAMSC and 10-fold more hAEC per gram of tissue (Casey, M. and MacDonald P., Biol Reprod, 1996, 55: 1253-1260).

hCMSCs are isolated from both first- and third-trimester chorion after mechanical and enzymatic removal of the trophoblastic layer with dispase. Chorionic mesodermal tissue is then digested (e.g., with collagenase or collagenase plus DNase). Mesenchymal cells also have been isolated from chorionic fetal villi through explant culture, although maternal contamination is more likely (Zhang, X., et al., Biochem Biophys Res Commun, 2006, 340: 944-952; Soncini, M. et al., J Tissue Eng Regen Med, 2007, 1:296-305; Zhang et al., Biochem Biophys Res Commun, 2006, 351: 853-859).

The surface marker profile of cultured hAMSC and hCMSC, and mesenchymal stromal cells (MSC) from adult bone marrow are similar. All express typical mesenchymal markers (CD90, CD73, CD105) but are negative for hematopoietic (CD34 and CD45) and monocytic markers (CD14). Surface expression of SSEA-3 and SSEA-4 and RNA for OCT-4 has been reported (Wei J. et al., Cell Transplant, 2003, 12: 545-552; Wolbank, S. et al., Tissue Eng, 2007, 13: 1173-1183; Alviano, F. et al., BMC Dev Biol, 2007, 7: 11; Zhao, P. et al, Transplantation, 2005, 79: 528-535). Both first- and third trimester hAMSC and hCMSC express low levels of HLA-A, B, C but not HLA-DR, indicating an immunoprivileged status (Portmann-Lanz, C. et al, Am J Obstet Gynecol, 2006, 194: 664-673; Wolbank, S. et al., Tissue Eng, 2007, 13: 1173-1183). The specific surface antigen expression at passages 2-4 for amniotic mesenchymal stromal cells and human chorionic mesenchymal stromal cells is as follows: Positive (≥95%): CD90, CD73, CD105; Negative (≤2%): CD45, CD34, HLA-DR.

Both hAMSCs and hCMSCs differentiate toward "classic" mesodermal lineages (osteogenic, chondrogenic, and adipogenic) and differentiation of hAMSC to all three germ layers-ectoderm (neural), mesoderm (skeletal muscle, cardiomyocytic and endothelial), and endoderm (pancreatic) was reported (Int'Anker, P. et al., Stem Cells, 2004, 22: 1338-1345; Portmann-Lanz, C. et al, Am J Obstet Gynecol, 2006, 194: 664-673; Wolbank, S. et al., Tissue Eng, 2007, 13: 1173-1183; Soncini, M. et al., J Tissue Eng Regen Med, 2007, 1:296-305; Alviano, F., BMC Dev Biol, 2007, 7: 11).

Human amniotic and chorionic cells successfully and persistently engraft in multiple organs and tissues in vivo. Human chimerism detection in brain, lung, bone marrow, thymus, spleen, kidney, and liver after either intraperitoneal or intravenous transplantation of human amnion and chorion cells into neonatal swine and rats was indeed indicative of an active migration consistent with the expression of adhesion and migration molecules (L-selectin, VLA-5, CD29, and P-selectin ligand 1), as well as cellular matrix proteinase (MMP-2 and MMP-9) (Bailo, M. et al., Transplantation, 2004, 78:1439-1448).

2.18. Umbilical Cord

Two types of umbilical stem cells can be found, namely hematopoietic stem cells (UC-HS) and mesenchymal stem cells, which in turn can be found in umbilical cord blood (UC-MS) or in Wharton's jelly (UC-MM). The blood of the umbilical cord has long been in the focus of attention of researchers as an important source of stem cells for transplantation, for several reasons: (1) it contains a higher number of primitive hematopoietic stem cells (HSC) per volume unit, which proliferate more rapidly, than bone marrow; (2) there is a lower risk of rejection after transplantation; (3) transplantation does not require a perfect HLA antigen match (unlike in the case of bone marrow); (4) UC blood has already been successfully used in the treatment of inborn metabolic errors; and (5) there is no need for a new technology for collection and storage of the mononuclear cells from UC blood, since such methods are long established.

Umbilical cord (UC) vessels and the surrounding mesenchyma (including the connective tissue known as Wharton's jelly) derive from the embryonic and/or extraembryonic mesodermis. Thus, these tissues, as well as the primitive germ cells, are differentiated from the proximal epiblast, at the time of formation of the primitive line of the embryo, containing MSC and even some cells with pluripotent potential. The UC matrix material is speculated to be derived from a primitive mesenchyma, which is in a transition state towards the adult bone marrow mesenchyma (Mihu, C. et al., 2008, Romanian Journal of Morphology and Embryology, 2008, 49(4):441-446).

The blood from the placenta and the umbilical cord is relatively easy to collect in usual blood donation bags, which contain anticoagulant substances. Mononuclear cells are separated by centrifugation on Ficoll gradient, from which the two stem cell populations will be separated: (1) hematopoietic stem cells (HSC), which express certain characteristic markers (CD34, CD133); and (2) mesenchymal stem cells (MSC) that adhere to the culture surface under certain conditions (e.g., modified McCoy medium and lining of vessels with Fetal Bovine Serum (FBS) or Fetal Calf Serum (FCS)). (Munn, D. et al., Science, 1998, 281: 1191-1193; Munn, D. et al., J Exp Med, 1999, 189: 1363-1372). Umbilical cord blood MSCs (UC-MS) can produce cytokines, which facilitate grafting in the donor and in vitro HSC survival compared to bone marrow MSC. (Zhang, X et al., Biochem Biophys Res Commun, 2006, 351: 853-859).

MSCs from the umbilical cord matrix (UC-MM) are obtained by different culture methods depending on the source of cells, e.g., MSCs from the connective matrix, from subendothelial cells from the umbilical vein or even from whole umbilical cord explant. They are generally well cultured in DMEM medium, supplemented with various nutritional and growth factors; in certain cases prior treatment of vessels with hyaluronic acid has proved beneficial (Baban, B. et al., J Reprod Immunol, 2004, 61: 67-77).

Exemplary factors secreted by umbilical cord tissue cells are disclosed in Zhang, X et al., Biochem Biophys Res Commun, 2006, 351: 853-859, the entire contents of which are incorporated herein by reference.

2.19. Lung Tissue

The lungs, which are paired organs that fill up the thoracic cavity, constitute an efficient air-blood gaseous exchange mechanism, accomplished by the passage of air from the mouth or nose, sequentially through an oropharynx, nasopharynx, a larynx, a trachea and finally through a progressively subdividing system of bronchi and bronchioles until it finally reaches alveoli where the air-blood gaseous exchange takes place. A resident niche with characteristic multipotent stem cells with c-kit positive surface profiles recently has been identified localized in small bronchioles alveoli. These stem cells express the transcription factors, Nanog, Oct3/4, Sox2 and Klf4, that govern pluripotency in embryonic stem cells. (Kajstura, J. et al., 2011, New Engl. J. Med., 364(19):1795-1806)).

2.20. Mammary Tissue

The mammary gland is a hormone sensitive bilayered epithelial organ comprising an inner luminal epithelial layer and an outer myoepithelial layer surrounded by a basement membrane in a stromal fat pad. Mammary stem cells with myoepithelial potential have been identified in their niches in the terminal ducts of mammary gland. (LaBarge, 2007, Stem Cell Rev., 3(2): 137-146).

2.21. Dermal Tissue

Dermal tissue, such as the skin functions as the primary barrier imparting protection from environmental insults. Skin is composed of an outer epidermis and inner dermis separated by a basement membrane (BM), rich in ECM and growth factors. The BM of the epidermal-dermal junction is composed of collagens (e.g., type IV and XVII), laminins, nidogen, fibronectin and proteoglycans that provide storage sites for growth factors and nutrients supporting the proliferation and adhesion of epidermal keratinocytes.

The epidermis is a solid epithelial tissue comprising keratinocytes that are linked to each other via cellular junctions, such as desmosomes. Keratinocytes are organized into distinct layers, comprising the stratum corneum, stratum granulosum, stratum spinosum and stratum basale. The epidermal matrix is made up of hyaluronan and other proteoglycans, including but not limited to, desmosealin, glycipans, versican, perlecan, and syndecans. (Sandjeu and Haftek, 2009, J. Physiol. Pharmacol. 60 (S4): 23-30). Epidermal desmosomes are multimeric complexes of transmembrane glycoprotein and cytosolic proteins with the keratin cytoskeleton. Desmosal proteins of the epidermis predominantly belong to the cadherin, Armadillo and plakin superfamilies.

The underlying dermis is connective tissue comprised primarily of fibroblasts with occasional inflammatory cells. Embedded within the dermis are also epidermal appendages, such as hair follicles and sebaceous glands, as well as nerves and cutaneous vasculature. The dermal ECM is essentially made of type I, III and V collagens and elastin together with noncollagenous components such as glycoproteins, proteoglycans, GAGs, cytokines and growth factors. Dermal collagens help mediate fibroblast-matrix interactions through a number of cell surface receptors and proteoglycans, such as β1-integrins. (Hodde and Johnson, 2007, Am. J. Clin. Dermatol. 8(2): 61-66).

During embryonic development, the epidermis originates from the ectoderm, while the dermis differentiates from the mesoderm. Following gastrulation, as mesenchymal stem cells of mesodermal origin populate the skin, they send signals to the single epidermal layer for initiation of epidermal stratification and direct the positioning of outgrowths of epidermal appendages, such as the hair follicles and sebaceous glands. Along with the mesenchyme, the basal layer of the epidermis organizes into a basement membrane that is rich in ECM proteins and growth factors. A number of different signaling pathways have been implicated in skin morphogenesis, including but not limited to Notch, Wnt, mitogen activated protein kinase (MAPK), nuclear factor-κB (NF-κB), transcriptional regulator, p63, the AP2 family of transcription factors, CCAAT/enhancer binding protein (C/EBP) transcriptional regulators, interferon regulatory 6 (URF6), grainyhead-like 3 (GRHL3) and Kruppel-like factor (KLF4). (Blanpain and Fuchs, 2009, Nat. Rev. Mol. Cell. Biol., 10(3): 207-217).

Adult skin undergoes constant cellular turnover whereby dead skin cells are shed and new cells are regenerated and replaced, by a process known as skin homeostasis. Several stem cell niches with distinct surface marker profiles and differentiation potentials have been identified. These include, but are not limited to, epidermal stem cells of interfollicular epidermis; bulge stem cells and epithelial stem cells of the hair follicle, dermal stem cells (e.g., multipotent dermal cells, skin-derived progenitor cells, dermis-derived multipotent stem cells and fibrocytes), dermal papilla stem cells, and sebaceous gland stem cells. Collectively, these skin stem cell niches partake in maintaining skin homeostasis with the help of growth factors and cytokines. (Zouboulis et al., 2008, Exp. Gerontol. 43: 986-997; Blanpain, 2010, Nature, 464: 686-687).

Exemplary factors secreted by skin tissue cells are disclosed in Blanpain and Fuchs, 2009, Nat. Rev. Mol. Cell. Biol., 10(3): 207-217, the entire contents of which are incorporated herein by reference.

2.22. Muscular Tissue

The muscular tissue compartments are comprised of contractile muscle tissue. These can be of three kinds: skeletal muscle associated with the skeletal system; cardiac muscle associated with the heart; and smooth muscle associated with the vasculature and gastrointestinal tract. Skeletal muscle tissue fibers are striated and are voluntary in function. Cardiac muscle fibers have characteristic intercalated discs and are involuntary in function. Smooth muscle tissue is comprised of spindle shaped cells and is involuntary in function.

Skeletal muscles are composed of a population of quiescent myogenic precursor cells known as satellite cells with muscle regenerating and self-renewal properties, as well as a population of multipotent muscle-derived stem cells (MDSC) with multilineage differentiation potential, such as mesodermal lineages including, but not limited to, myogenic lineages, adipogenic lineages, osteogenic lineages, chondrogenic lineages, endothelial and hematopoetic lineages, and ectodermal lineages, including not limited to neuron-like cells. (Xu et al., 2010, Cell Tissue Res., 340: 549-567).

Skeletal muscle satellite cells are quiescent mononucleated cells that are resident in the muscle fiber membrane, beneath the basal lamina forming distinct stem cell niches. Similar to other stem cell niches, the skeletal muscle satellite cell niche is a dynamic structure, capable of altering between inactive (quiescent) and activated states in response to external signals. Once activated, satellite cells have the potential to proliferate, expand and differentiate along the myogenic lineage. The basal lamina, which serves to separate individual skeletal muscle fibers, known as myofibers, and their associated satellite cell and stem cell niches, from the cells of the interstitium, is rich in collagen type IV, perlecan, laminin, entactin, fibronectin and several other glycoproteins and proteoglycans, that may function as receptors to growth factors effectuating their activation by extracellular processing and modifications. In addition to these interactions provided by the ECM, neighboring cells, such as endothelial cells and multipotent stem cells derived from blood vessels, such as pericytes and mesoangioblasts, or neural components, all have the potential of affecting the niche microenvironment. (Gopinath et al., 2008, Aging Cell, 7: 590-598).

Endogenous cardiac stem cells have also been identified in cardiac stem cell niches. (Mazhari and Hare, 2007, Nat. Clin. Pract. Cardiovasc. Med., 4(S1): S21-S26).

Vascular smooth muscle cells are derived from embryonic cardiac neural crest stem cells, as well as proepicardial cells and endothelial progenitor cells. Smooth muscle differentiation is dependent on a combination of factors, including but not limited to Pax3, Tbx1, FoxC1 and serum response factor, interacting with microenvironment components of the ECM, such as BMPs, Wnts, endothelin (ET)-1, and FGF8. In the adult, vascular smooth muscle cells undergo constant degeneration, repair and regeneration by the action of both multipotent bone-derived mesenchymal cells as well as smooth muscle stem cells resident within vascular smooth muscle tissue. (Hirschi and Majesky, 2004, The Anatomical Record, Part A, 276A: 22-33).

2.23. Neural Tissue

The neural tissue compartments are comprised of neurons and the neuroglia, embedded with the neural matrix. Neural tissue is ectodermal in origin, derived from the embryonic neural plate. Neural tissue is primarily located within the brain, spinal cord and nerves.

Resident neural stem cell niches have been identified in the adult mammalian brain, restricted to the subventricular zone as well as to the lateral ventricle and dentate gyrus subgranular zone of the hippocampus. Astrocytes, which are star-shaped nerve cells, serve as both neural stem cells as well as supporting niche cells secreting essential growth factors that provide support for neurogenesis and vasculogenesis. The basal lamina and associated vasculogenesis are essential components of the niche. Embryonic molecular factors and signals persist within the neural stem cell niches and play critical role in neurogenesis. Neural stem cells have VEGFR2, doublecortin and Lex (CD15) markers. Major signaling pathways implicated in neurogenesis include but are not limited to Notch, Eph/ephrins, Shh, and BMPs. (Alvarez-Buylla and Lim, 2004, Neuron, 41: 683-686).

Exemplary factors secreted by nerve tissue cells are listed in Alvarez-Buylla and Lim (2004), Neuron, 41: 683-686, the entire contents of which are incorporated herein by reference.

2.24. Peritoneum

The peritoneum is the serous membrane that forms the lining of the abdominal cavity or coelom in amniotes and some invertebrates, such as annelids. It covers most of the intra-abdominal (or coelomic) organs, and is composed of a layer of mesothelium supported by a thin layer of connective tissue. The peritoneum supports the abdominal organs and serves as a conduit for their blood vessels, lymph vessels, and nerves. The peritoneum develops ultimately from the mesoderm of the trilaminar embryo. As the mesoderm differentiates, one region known as the lateral plate mesoderm splits to form two layers separated by an intraembryonic coelom. These two layers develop later into the visceral and parietal layers found in all serous cavities, including the peritoneum.

3. Stem Cells

In some embodiments, the viable cells for priming can include stem cells. The term "stem cells" as used herein refers to undifferentiated cells having high proliferative potential with the ability to self-renew that can generate daughter cells that can undergo terminal differentiation into more than one distinct cell phenotype. Stem cells are distinguished from other cell types by two characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

Embryonic stem cells (EmSC) are stem cells derived from an embryo that are pluripotent, i.e., they are able to differentiate in vitro into endodermal, mesodermal and ectodermal cell types.

Adult (somatic) stem cells are undifferentiated cells found among differentiated cells in a tissue or organ. Their primary role in vivo is to maintain and repair the tissue in which they are found. Adult stem cells have been identified in many organs and tissues, including brain, bone marrow, peripheral blood, blood vessels, skeletal muscles, skin, teeth, gastrointestinal tract, liver, ovarian epithelium, and testis. Adult stem cells are thought to reside in a specific area of each tissue, known as a stem cell niche, where they may remain quiescent (non-dividing) for long periods of time until they are activated by a normal need for more cells to maintain tissue, or by disease or tissue injury. Examples of adult stem cells include, but are not limited to, hematopoietic stem cells, mesenchymal stem cells, neural stem cells, epithelial stem cells, and skin stem cells.

3.1. Hematopoietic Stem Cells (HSCs)

Hematopoietic stem cells (also known as the colony-forming unit of the myeloid and lymphoid cells (CFU-M,L), or CD34+ cells) are rare pluripotential cells within the blood-forming organs that are responsible for the continued production of blood cells during life. While there is no single cell surface marker exclusively expressed by hematopoietic stem cells, it generally has been accepted that human HSCs have the following antigenic profile: CD 34+, CD59+, Thy1+(CD90), CD38low/-, C-kit-/low and, lin-. CD45 is also a common marker of HSCs, except platelets and red blood cells. HSCs can generate a variety of cell types, including erythrocytes, neutrophils, basophils, eosinophils, platelets, mast cells, monocytes, tissue macrophages, osteoclasts, and the T and B lymphocytes. The regulation of hematopoietic stem cells is a complex process involving self-renewal, survival and proliferation, lineage commitment and differentiation and is coordinated by diverse mechanisms including intrinsic cellular programming and external stimuli, such as adhesive interactions with the microenvironmental stroma and the actions of cytokines.

Different paracrine factors are important in causing hematopoietic stem cells to differentiate along particular pathways. Paracrine factors involved in blood cell and lymphocyte formation are called cytokines. Cytokines can be made by several cell types, but they are collected and concentrated by the extracellular matrix of the stromal (mesenchymal) cells at the sites of hematopoiesis. For example, granulocyte-macrophage colony-stimulating factor (GM-CSF) and the multilineage growth factor IL-3 both bind to the heparan sulfate glycosaminoglycan of the bone marrow stroma. The extracellular matrix then presents these factors to the stem cells in concentrations high enough to bind to their receptors.

3.2. Mesenchymal Stem Cells (MSCs)

Mesenchymal stem cells (MSCs) (also known as bone marrow stromal stem cells or skeletal stem cells) are non-blood adult stem cells found in a variety of tissues. They are characterized by their spindle-shape morphologically; by the expression of specific markers on their cell surface; and by their ability, under appropriate conditions, to differentiates along a minimum of three lineages (osteogenic, chondrogenic, and adipogenic).

No single marker that definitely delineates MSCs in vivo has been identified due to the lack of consensus regarding the MSC phenotype, but it generally is considered that MSCs are positive for cell surface markers CD105, CD166, CD90, and CD44 and that MSCs are negative for typical hematopoietic antigens, such as CD45, CD34, and CD14. Other MSC markers can include CD271, CD73, CD 29, CD117, CD200, CD348, and Stro-1. As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic-supporting stroma. Studies using transgenic and knockout mice and human musculoskeletal disorders have reported that MSC differentiate into multiple lineages during embryonic development and adult homeostasis.

Analyses of the in vitro differentiation of MSCs under appropriate conditions that recapitulate the in vivo process have led to the identification of various factors essential for stem cell commitment. Among them, secreted molecules and their receptors (e.g., transforming growth factor-β), extracellular matrix molecules (e.g., collagens and proteoglycans), the actin cytoskeleton, and intracellular transcription factors (e.g., Cbfa1/Runx2, PPARγ, Sox9, and MEF2) have been shown to play important roles in driving the commitment of multipotent MSCs into specific lineages, and maintaining their differentiated phenotypes.

For example, it has been shown that osteogenesis of MSCs, both in vitro and in vivo, involves multiple steps and the expression of various regulatory factors. During osteogenesis, multipotent MSCs undergo asymmetric division and generate osteoprecursors, which then progress to form osteoprogenitors, preosteoblasts, functional osteoblasts, and eventually osteocytes. This progression from one differentiation stage to the next is accompanied by the activation and subsequent inactivation of transcription factors, i.e., Cbfa1/Runx2, Msx2, Dlx5, Osx, and expression of bone-related marker genes, i.e., osteopontin, collagen type I, alkaline phosphatase, bone sialoprotein, and osteocalcin.

Members of the Wnt family also have been shown to impact MSC osteogenesis. Wnts are a family of secreted cysteine-rich glycoproteins that have been implicated in the regulation of stem cell maintenance, proliferation, and differentiation during embryonic development. Canonical Wnt signaling increases the stability of cytoplasmic β-catenin by receptor-mediated inactivation of GSK-3 kinase activity and promotes β-catenin translocation into the nucleus. The active β-catenin/TCF/LEF complex then regulates the transcription of genes involved in cell proliferation. In humans, mutations in the Wnt co-receptor, LRP5, lead to defective bone formation. "Gain of function" mutation results in high bone mass, whereas "loss of function" causes an overall loss of bone mass and strength, indicating that Wnt signaling is positively involved in embryonic osteogenesis. Canonical Wnt signaling pathway also functions as a stem cell mitogen via stabilization of intracellular β-catenin and activation of the β-catenin/TCF/LEF transcription complex, resulting in activated expression of cell cycle regulatory genes, such as Myc, cyclin D1, and Msx1. When MSCs are exposed to Wnt3a, a prototypic canonical Wnt signal, under standard growth medium conditions, they show markedly increased cell proliferation and a decrease in apoptosis, consistent with the mitogenic role of Wnts in hematopoietic stem cells. However, exposure of MSCs to Wnt3a conditioned medium or overexpression of ectopic Wnt3a during osteogenic differentiation inhibits osteogenesis in vitro through β-catenin mediated down-regulation of TCF activity. The expression of several osteoblast specific genes, e.g., alkaline phosphatase, bone sialoprotein, and osteocalcin, is dramatically reduced, while the expression of Cbfa1/Runx2, an early osteoinductive transcription factor is not altered, implying that Wnt3α-mediated canonical signaling pathway is necessary, but not sufficient, to completely block MSC osteogenesis. On the other hand, Wnt5a, a typical non-canonical Wnt member, has been shown to promote osteogenesis in vitro. Since Wnt3a promotes MSC proliferation during early osteogenesis, it is thought likely that canonical Wnt signaling functions in the initiation of early osteogenic commitment by increasing the number of osteoprecursors in the stem cell compartment, while non-canonical Wnt drives the progression of osteoprecursors to mature functional osteoblasts.

3.3. Epithelial Stem Cells

An epithelial membrane is a continuous multicellular sheet composed of an epithelium adhered to underlying connective tissue. Epithelial membranes can be cutaneous (e.g. skin), mucous (e.g., gastrointestinal lining) and serous (e.g. pleural lining, pericardial lining and peritoneal lining).

Epithelial stem cells line the gastrointestinal tract in deep crypts and give rise to absorptive cells, goblet cells, paneth cells, and enteroendocrine cells.

3.4. Neural Stem Cells

The adult mammalian brain contains multipotent neural stem cells (NSCs) that have the capacity to self-renew and are responsible for neurogenesis and maintenance of specific regions of the adult brain. Neural stem cells can generate astrocytes, oligodendrocytes, and neurons. Self-renewal and differentiation of neural stem cells are directed by interactions within a complex network of intrinsic regulators and extrinsic factors. Recent proteomic analyses have identified a horde of transcription factors belonging to the Wnt/β-catenin, Notch and Sonic Hedgehog (shh) pathways, in addition to epigenetic modifications, microRNA networks and extrinsic growth factor networks, including but not limited to the FGFs and BMPs. (Yun et al., 2010, J. Cell. Physiol. 225: 337-347).

With the advent of high throughput microarray and proteomic technologies, a number of different molecular signatures of neural stem cells have been identified, including but not limited to CD133/promini, nestin, NCAM, the HMG-box transcription factor, Sox2 and the bHLH protein, Olig2. (Holmberg et al., 2011, PLoS One., 6(3): e18454; Hombach-Klonisch et al., 2008, J. Mol. Med. 86(12): 1301-1314).

3.5. Skin Stem Cells

Several different adult stem cell populations with distinct molecular signatures are responsible for maintaining skin homeostasis. These include, but are not limited to, epidermal stem cells of the interfollicular region, epidermal stem cells of the hair follicle (also known as the bulge stem cells), dermal stem cells, dermal papilla stem cells, and sebaceous gland stems. The epidermal stem cells are ectodermal in origin while the dermal stem cells originate from the mesoderm and are mesenchymal in nature. (Zouboulis et al., 2008, Exp. Gerontol., 43: 986-997).

The interfollicular epidermal stem cells reside in the basal layer of the epidermis and give rise to keratinocytes, which migrate to the surface of the skin and form a protective layer. A diverse range of molecular signatures has been described for such epidermal stem cells including but not limited to high α6-integrin, low CD71, high Delta 1 (Notch signaling ligand) and high CD200 expression levels. The follicular stem cells located at the base of hair follicles give rise to both hair follicle and to the epidermis. These are characterized by Cytokeratin 15 (K15) immunostaining and high levels of β1-integrin. Dermal stem cell marker proteins include but are not limited to nestin, fibronectin and vimentin, the surface markers for dermal papilla stem cells include mesenchymal stem cell markers such as for example CD44, CD73 and CD90 and sebaceous stem cells express keratin 14. (Zouboulis et al., 2008, Exp. Gerontol., 43: 986-997).

In addition, adult somatic cells can be reprogrammed to enter an embryonic stem cell-like state by being forced to express a set of transcription factors, for example, Oct-3/4 (or Pou5f1, the Octamer transcription factor-3/4), the Sox family of transcription factors (e.g., Sox-1, Sox-2, Sox-3, and Sox-15), the Klf family transcription factors (Klf-1, Klf-2, Klf-4, and Klf-5), and the Myc family of transcription factors (e.g., c-Myc, N-Myc, and L-Myc). For example, human inducible Pluripotent Stem cells (iPSCs) are cells reprogrammed to express transcription factors that express stem cell markers and are capable of generating cells characteristic of all three germ layers (i.e., ectoderm, mesoderm, and endoderm).

3.6. Stem Cell Niches

Adult tissue compartments contain endogenous niches of adult stem cells that are capable of differentiating into diverse cell lineages of determined endodermal, mesodermal or ectodermal fate depending on their location in the body. For example, in the presence of an appropriate set of internal and external signals, bone marrow-derived adult hematopoietic stem cells (HSCs) have the potential to differentiate into blood, endothelial, hepatic and muscle cells; brain-derived neural stem cells (NSCs) have the potential to differentiate into neurons, astrocytes, oligodendrocytes and blood cells; gut- and epidermis-derived adult epithelial stem cells (EpSCs) have the potential to give rise to cells of the epithelial crypts and epidermal layers; adipose-derived stem cells (ASCs) have the potential to give rise to fat, muscle, cartilage, endothelial cells, neuron-like cells and osteoblasts; and bone-marrow-derived adult mesenchymal stem cells (MSCs) have the potential to give rise to bone, cartilage, tendon, adipose, muscle, marrow stroma and neural cells.

Endogenous adult stem cells are embedded within the ECM component of a given tissue compartment, which, along with support cells, form the cellular niche. Such cellular niches within the ECM scaffold together with the surrounding microenvironment contribute important biochemical and physical signals, including growth factors and transcription factors required to initiate stem cell differentiation into committed precursors cells and subsequent precursor cell maturation to form adult tissue cells with specialized phenotypic and functional characteristics.

4. Extracellular Matrix

The viable cells of the present invention can be endogenous to and resident within the host tissue compartment, e.g., within the ECM. During priming and after priming (e.g., when grafted), the cells can secrete extracellular macromolecules or other factors into the ECM, as well as migrate in the ECM. Where cell-free grafts are needed, the cells can be removed after priming, leaving behind ECM. Alternatively, where non-viable grafts are required, the cells are devitalized but not removed from the graft. Thus, ECM plays an important role in some embodiments of the present invention.

The ECM is an intricate network of secreted extracellular macromolecules that largely fills the extracellular space in the tissue compartments and comprises large polymeric complexes of glycosaminoglycans (GAGs) and proteoglycans. GAGs are negatively charged unbranched polysaccharide chains comprising repeating disaccharide units. Each repeating disaccharide unit of a GAG chain contains an amino sugar (N-acetylglucosamine or N-acetyl glucosamine), which in most cases is sulfated, and an -uronic acid (glucuronic or iduronic acid). Four main types of GAG molecules are distinguished based on sugar residues, type of linkage, number and location of sulfate groups: (1) hyaluronan; (2) chondroitan sulfate and dermatan sulfate; (3) heparan sulfate and heparin; and (4) keratin sulfate.

GAG chains are inflexible and tend to adopt extended conformations occupying a huge volume relative to their mass, forming gels even at low concentrations. Their high density of negative charges attracts cations, such as Na+, that are effective in osmotic absorption of large amounts of water into the matrix. This creates high turgor enabling the ECM to withstand compressive forces.

Hyaluronan (also termed hyaluronic acid or hyaluronate) (HA), which comprises a regular repeating sequence of up to 25,000 nonsulfated disaccharide units, serves many functions, many of which depend on the binding of HA-binding proteins and proteoglycans, which are either themselves constituents of the ECM or are integral constituents of cell surfaces. For example, HA resists compressive forces in joints as a major constituent of joint fluid serving as a lubricant; serves as a space filler during embryonic development; creates a cell-free space in epithelial compartment to allow cell migration during the formation of heart, cornea and other organs; and plays a role in wound repair. Excess HA is usually degraded by hyaluronidase.

All GAGs, except for HA, are covalently linked to proteins in the form of proteoglycans. During their synthesis, the polypeptide chain of proteoglycans is synthesized on membrane-bound ribosomes and threaded into the lumen of endoplasmic reticulum, from which they are sorted in the Golgi apparatus, and assembled with polysaccharide chains. While still in the Golgi, proteoglycans undergo a series of sequential and coordinated sulfation and epimerization reactions to produce sulfated proteoglycans. Sulfated and non-sulfated proteoglycans then travel through the Golgi network and are ultimately secreted into the ECM by exocytosis with the help of secretory vesicles.

Proteoglycans are heterogenous molecules, with core proteins ranging in molecular weight from 10 kD to about 600 kD and with attached GAG chains varying in number and type, further modified by a complex variable pattern of sulfate groups. At least one of the proteoglycan sugar side chains is a GAG; the core protein is usually a glycoprotein, but may comprise up to 95% carbohydrate by weight, mostly as long unbranched GAG chains up to at least 80 sugar residues long.

Proteoglycans along with their attached GAG chains regulate the activities of secreted macromolecules. They can serve as selective molecular sieves regulating a size-based trafficking of molecules and cells, and play a role in cell-cell signaling. Proteoglycans modulate the activities of secreted factors, such as growth factors and cytokines, by binding to them For example, binding of fibroblast growth factor (FGF) to heparan sulfate chains of proteoglycans is required for FGF activation of its cell surface receptors. On the other hand, for example, binding of a ubiquitous growth regulatory factor, such as transforming growth factor β (TGF-β) to core proteins of several ECM proteoglycans, such as decorin, results in inhibition of TGF-β activity. Proteoglycans also bind and regulate the activities of other types of secreted proteins, such as proteases and protease inhibitors. Cell-surface proteoglycans also may act as co-receptors: for example, syndecan binds to FGF and presents it to the FGF-receptor. Similarly, betaglycan binds to TGF-β and presents it to TGF-β receptors.

Collagens and elastin are the major fibrous proteins of the ECM. Collagens comprise a family of highly characteristic fibrous proteins and are a major component of skin and bone. Collagen fibers consist of globular units of the collagen subunit tropocollagen. Each tropocollagen subunit molecule comprises three polypeptide chains, called a chains, each exhibiting a left-handed helical conformation, that are wrapped around each other in a right-handed coiled coil structure, also called a triple helix or super helix. A characteristic feature of collagen is a repeating tripeptide unit comprising Glycine-Proline-X or Glycine-X-Hydroxyproline, where X may be any amino acid. The presence of Glycine at every third position in a collagen unit is critical for maintaining the coiled coil structure, since each repeating glycine residue sits on the interior axis of the helix, which sterically hinders bulkier sidechains. Prolines and hydroxyprolines help stabilize the triple helix. Collagen is secreted as procollagen molecules, which undergo proteolytic processing and subsequent assembly to form collagenous fibrils. Collagens are highly glycosylated during protein trafficking through intracellular secretory pathways.

Collagens are classified into various types depending on the nature of their a chains. Collagen molecules composition, class and distribution are reviewed extensively by Shoulders and Raines, Annu. Rev. Biochem. 2009, 78: 929-958 and Kelly et al. 1984, Bailey's Textbook of Microscopic Anatomy, Williams and Wilkins, 18th edition.

A network of elastic fibers in the ECM offers resilience and elasticity so that organs are able to recoil following transient stretch. Elastic fibers primarily comprise the fibrous protein elastin, a highly hydrophobic protein about 750 amino acids in length that is rich in proline and glycine, is not glycosylated and is low in hydroxyproline and hyroxylysine. Elastin molecules are secreted into the ECM and assemble into elastic fibers close to the plasma membrane. Upon secretion, elastin molecules become highly cross-linked to form an extensive network of fibers and sheets.

The ECM also comprises many non-collagen adhesive proteins, usually with multiple domains containing binding sites of other macromolecules and for cell-surface receptors. One such adhesive protein, fibronectin, is a large glycoprotein comprising two subunits joined by a pair of disulfide bonds near the carboxy termini. Each subunit is folded into a series of rod-like domains interspersed by regions of flexible polypeptide chains. Each domain further comprises repeating modules of various types. One major type of fibronectin repeating module, called type III fibronectin repeat, is about 90 amino acids in length and occurs at least 15 times in each subunit. Fibronectin type III repeats have characteristic Arg-Gly-Asp (RGD) tripeptide repeats that function as binding sites for other proteins such as collagen, heparin or cell surface receptors. Fibronectin not only plays an important role in cell adhesion to the ECM, but also in guiding cell migration in vertebrate embryos.

Laminin, another adhesive glycoprotein of the ECM, is a major constituent (along with type IV collagen and another glycoprotein, entactin) of the basal lamina, a tough sheet of ECM formed at the base of epithelial cells. Laminin is a large flexible complex, about 850 kD in molecular weight, with three very long polypeptide chains arranged in the form of an asymmetric cross held together with disulfide bonds. Laminin contains numerous functional domains, e.g., one binds to type IV collagen, one to heparan sulfate, one to entactin and two or more to laminin receptor proteins on the cell surface.

5. Growth Factors

Growth factors can, in some embodiments, be used to prime the viable cells. Growth factors are extracellular polypeptide molecules that bind to a cell-surface receptor triggering an intracellular signaling pathway, leading to proliferation, differentiation, or other cellular response. These pathways stimulate the accumulation of proteins and other macromolecules, and they do so by both increasing their rate of synthesis and decreasing their rate of degradation. One intracellular signaling pathway activated by growth factor receptors involves the enzyme PI 3-kinase, which adds a phosphate from ATP to the 3 position of inositol phospholipids in the plasma membrane. The activation of PI 3-kinase leads to the activation of several protein kinases, including S6 kinase. The S6 kinase phosphorylates ribosomal protein S6, increasing the ability of ribosomes to translate a subset of mRNAs, most of which encode ribosomal components, as a result of which, protein synthesis increases. When the gene encoding S6 kinase is inactivated in *Drosophila*, cell numbers are normal, but cell size is abnormally small, and the mutant flies are small. Growth factors also activate a translation initiation factor called eIF4E, further increasing protein synthesis and cell growth.

Growth factor stimulation also leads to increased production of the gene regulatory protein Myc, which plays a part in signaling by mitogens. Myc increases the transcription of a number of genes that encode proteins involved in cell metabolism and macromolecular synthesis. In this way, it stimulates both cell metabolism and cell growth.

Some extracellular signal proteins, including platelet-derived growth factor (PDGF), can act as both growth factors and mitogens, stimulating both cell growth and cell-cycle progression. This functional overlap is achieved in part by overlaps in the intracellular signaling pathways that control these two processes. The signaling protein Ras, for example, is activated by both growth factors and mitogens. It can stimulate the PI3-kinase pathway to promote cell growth and the MAP-kinase pathway to trigger cell-cycle progression. Similarly, Myc stimulates both cell growth and cell-cycle progression. Extracellular factors that act as both growth factors and mitogens help ensure that cells maintain their appropriate size as they proliferate.

Since many mitogens, growth factors, and survival factors are positive regulators of cell-cycle progression, cell growth, and cell survival, they tend to increase the size of organs and organisms. In some tissues, however, cell and tissue size also is influenced by inhibitory extracellular signal proteins that oppose the positive regulators and thereby inhibit organ growth. The best-understood inhibitory signal proteins are TGF-β and its relatives. TGF-β inhibits the proliferation of several cell types, either by blocking cell-cycle progression in G1 or by stimulating apoptosis. TGF-β binds to cell-surface receptors and initiates an intracellular signaling pathway that leads to changes in the activities of gene regulatory proteins called Smads. This results in complex changes in the transcription of genes encoding regulators of cell division and cell death.

Bone morphogenetic protein (BMP), a TGF-β family member, helps trigger the apoptosis that removes the tissue between the developing digits in the mouse paw. Like TGF-β, BMP stimulates changes in the transcription of genes that regulate cell death.

Non-limiting, exemplary growth factors are discussed in detail below. Other growth factors known in the art are also included in the present invention.

5.1. Fibroblast Growth Factor (FGF)

The fibroblast growth factor (FGF) family currently has over a dozen structurally related members. FGF1 is also known as acidic FGF; FGF2 is sometimes called basic FGF (bFGF); and FGF7 sometimes goes by the name keratinocyte growth factor. Over a dozen distinct FGF genes are known in vertebrates; they can generate hundreds of protein isoforms by varying their RNA splicing or initiation codons in different tissues. FGFs can activate a set of receptor tyrosine kinases called the fibroblast growth factor receptors (FGFRs). Receptor tyrosine kinases are proteins that extend through the cell membrane. The portion of the protein that binds the paracrine factor is on the extracellular side, while a dormant tyrosine kinase (i.e., a protein that can phosphorylate another protein by splitting ATP) is on the intracellular side. When the FGF receptor binds an FGF (and only when it binds an FGF), the dormant kinase is activated, and phosphorylates certain proteins within the responding cell, activating those proteins.

FGFs are associated with several developmental functions, including angiogenesis (blood vessel formation), mesoderm formation, and axon extension. While FGFs often can substitute for one another, their expression patterns give them separate functions. FGF2 is especially important in angiogenesis, whereas FGF8 is involved in the development of the midbrain and limbs.

The expression levels of angiogenic factors, such as VEGF, IGF, PDGF, HGF, FGF, TGFm Angiopoeitin-1, and stem cell factor (SCF) have been found to differ amongst bone-derived-, cartilage-derived-, and adipose-derived MSCs. (Peng et al., 2008, Stems Cells and Development, 17: 761-774).

5.2. Insulin-like Growth Factor (IGF-1)

IGF-1, a hormone similar in molecular structure to insulin, has growth-promoting effects on almost every cell in the body, especially skeletal muscle, cartilage, bone, liver, kidney, nerves, skin, hematopoietic cell, and lungs. It plays an important role in childhood growth and continues to have anabolic effects in adults. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signaling molecules, including SHP2 and STAT5B. Its primary action is mediated by binding to its specific receptor, the Insulin-like growth factor 1 receptor (IGF1R), present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the pituitary gland, released into the blood stream, and then stimulates the liver to produce IGF-1. IGF-1 then stimulates systemic body growth. In addition to its insulin-like effects, IGF-1 also can regulate cell growth and development, especially in nerve cells, as well as cellular DNA synthesis.

5.3. Transforming Growth Factor Beta (TGF-β)

There are over 30 structurally related members of the TGF-β superfamily, and they regulate some of the most important interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell. The TGF-β superfamily includes the TGF-β family, the activin family, the bone morphogenetic proteins (BMPs), the Vg-1 family, and other proteins, including glial-derived neurotrophic factor (GDNF, necessary for kidney and enteric neuron differentiation) and Müllerian inhibitory factor, which is involved in mammalian sex determination. TGF-β family members TGF-β1, 2, 3, and 5 are important in regulating the formation of the extracellular matrix between cells and for regulating cell division (both positively and negatively). TGF-β1 increases the amount of extracellular matrix epithelial cells make both by stimulating collagen and fibronectin synthesis and by inhibiting matrix degradation. TGF-βs may be critical in controlling where and when epithelia can branch to form the ducts of kidneys, lungs, and salivary glands.

The members of the BMP family were originally discovered by their ability to induce bone formation. Bone formation, however, is only one of their many functions, and they have been found to regulate cell division, apoptosis (programmed cell death), cell migration, and differentiation. BMPs can be distinguished from other members of the TGF-β superfamily by their having seven, rather than nine, conserved cysteines in the mature polypeptide. The BMPs include proteins such as Nodal (responsible for left-right axis formation) and BMP4 (important in neural tube polarity, eye development, and cell death).

5.4. Neural Epidermal Growth-Factor-Like 1 (NELL1)

Neural epidermal growth-factor-like 1 (NEL-like 1, NELL1) is a gene that encodes an 810-amino acid polypeptide, which trimerizes to form a mature protein involved in the regulation of cell growth and differentiation. The neural epidermal growth-factor-like (nel) gene first was detected in neural tissue from an embryonic chicken cDNA library, and its human orthologue NELL1 was discovered later in B-cells. Studies have reported the presence of NELL in various fetal and adult organs, including, but not limited to, the brain, kidneys, colon, thymus, lung, and small intestine.

Much of what is known about NELL1 concerns its role in bone development. See, e.g., U.S. Pat. Nos. 7,884,066, 7,833,968, 7,807,787, 7,776,361, 7,691,607, 7,687,462, 7,544,486, and 7,052,856, the entire contents of which are incorporated herein by reference. It generally is believed that during osteogenic differentiation, NELL1 signaling may involve an integrin-related molecule and tyrosine kinases that are triggered by NELL1 binding to a NELL1 specific receptor and a subsequent formation of an extracellular complex. As thus far understood, in human NELL1 (hNELL1), the laminin G domain comprises about 128 amino acid residues that show a high degree of similarity to the laminin G domain of extracellular matrix ("ECM") proteins, such as human laminin α3 chain (hLAMA3), mouse laminin α3 chain (mLAMA3), human collagen 11 α3 chain (hCOLA1), and human thrombospondin-1 (hTSP1). This complex facilitates either activation of Tyr-kinases, inactivation of Tyr phosphatases, or intracellular recruitment of Tyr-phosphorylated proteins. The ligand bound integrin (cell surface receptors that interact with ECM proteins such as, for example, laminin 5, fibronectin, vitronectin, TSP1/2) transduces the signals through activation of the focal adhesion kinase (FAK) followed by indirect activation of the Ras-MAPK cascade, and then leads to osteogenic differentiation through Runx2; the laminin G domain is believed to play a role in the interaction between integrins and a 67 kDa laminin receptor.

The NELL1 protein is a secreted cytoplasmic heterotrimeric protein. The complete role NELL1 plays in vivo remains unknown. Several studies have indicated that NELL1 may play a role in bone formation, inflammatory bowel disease, and esophageal adenocarcinoma, among others. It generally is believed that NELL1 induces osteogenic differentiation and bone formation of osteoblastic cells during development. Studies have shown that the NELL1 protein (1) transiently activates the mitogen-activated protein kinase ("MAPK") signaling cascade (which is involved in various cellular activities such as gene expression, mitosis, differentiation, proliferation and apotosis); and (2) induces phosphorylation of Runx2 (a transcription factor associated with osteoblast differentiation). Consequently, it generally is believed that upon binding to a specific receptor, NELL1 transduces an osteogenic signal through activation of certain Tyr-kinases associated with the Ras-MAPK cascade, which ultimately leads to osteogenic differentiation. Studies have shown that bone development is severely disturbed in transgenic mice where over-expression of NELL1 has been shown to lead to craniosynotosis (premature ossification of the skull and closure of the sutures) and NELL1 deficiency manifests in skeletal defects due to reduced chondrogenesis and osteogenesis.

6. Tissue and Cell Priming

Methods and compositions for priming tissues and resident cells therein are provided. In some embodiments, the primed tissues and/or cells can be used in grafting, surgical, medical or other therapeutic procedures. For example, grafts can contain viable cells that have been primed or pre-conditioned during processing prior to clinical usage. These viable cells are endogenous to the tissue (e.g., resident within the tissue compartment) and are not isolated or dissociated from the tissue. In other embodiments, grafts can contain non-viable cells or cell remnants that have been primed or pre-conditioned during processing prior to clinical usage. In still other embodiments, grafts can have had viable cells that have been primed or pre-conditioned and then removed during processing prior to clinical usage. Grafts can also have a combination of viable cells, non-viable cells, and/or removed cells. Priming can provide an improved and/or more rapid therapeutic effect such as enhanced healing, compared to traditional or non-primed graft.

In some embodiments, the primed tissue or cells can be used in connection with the tissuegenic cells disclosed in U.S. Pat. Nos. 8,834,928, 8,883,210 and 9,352,003, all of which are incorporated herein by reference in their entirety.

Figure 1B:
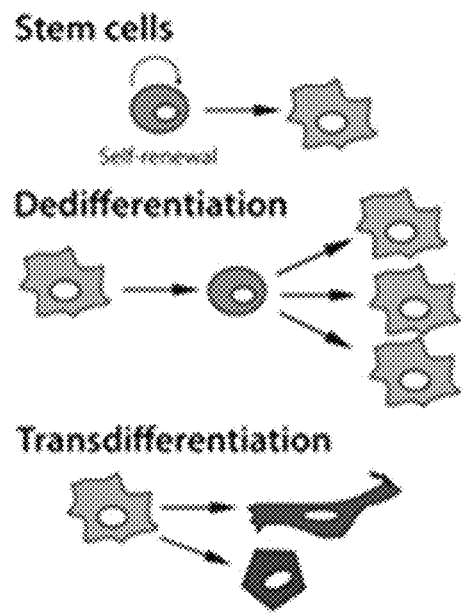

Without wishing to be bound by theory, it is believed that at least some of the viable cells, resident in the host tissue, can be reprogramed during priming. For example, in response to priming stimuli, cells can be induced to differentiate, or de-differentiate, as illustrated in FIG. 1A. Further, as illustrated in FIG. 1B, stem cells can be induced to exit self-renewal cycles and differentiate into a specific cell type, de-differentiate into stem cells before re-differentiation at a later time point, or trans-differentiate into multiple cell types. Selecting proper priming conditions can direct the cells to any of the foregoing paths. In addition, cells can also be reprogramed to exit the apoptosis cascade, and be kept alive in conditions that would normally be fatal (e.g., in a harvested graft tissue). It should be noted that complex tissues may contain many different cell types at various development and differentiation stages, and thus, different reprogramming processes can take place simultaneously within the same tissue during priming. These at least partially reprogramed cells when grafted, can directly participate in healing process and/or actively secret factors that elicit healing.

Various tissues and endogenous cells resident therein (e.g., those disclosed herein) can be subjected to the priming or pre-conditioning methods of the present invention. Non-limiting examples of tissues containing viable cells that can be primed include, placenta, amnion, chorion, umbilical cord, Wharton's jelly, bone, cartilage (e.g., articular, auricular, costal), spinal disc, periosteum, adipose, meniscus, muscle, tendon, ligament, skin, cardiovascular, peritoneum, fascia, nerve, cornea, visceral organs, reproductive tissues, hair follicles, foreskin, and dental tissue. In some embodiments, the tissue can be an allograft, autograft or xenograft. The cells can include stem cells, non-terminally differentiated cells and/or differentiated cells as disclosed herein.

In some embodiments, the viable cells can be primed by exposing to biochemical stimulation with soluble factors (e.g., growth-inductive component, medium component, inhibitor, antioxidant, vitamin, enzyme, adipokine, cytokine, growth factor, hormone, steroid and differentiation-inducing factor) for a predetermined duration of time.

Growth-inductive components can include but are not limited to mitogens and growth factors. Examples of growth-inductive components include PDGF, EGF, TGF-β, and FGF.

Antioxidants can include but are not limited to Vitamin C (ascorbic acid), Vitamin E, glutathione, lipoic acid, melatonin, uric acid, carotenes, ubiquinol, resveratrol, tocopherols, polyphenols, selenium, and flavanoids.

Medium components include but are not limited to glycine, glutamine, sodium pyruvate, and other amino acids.

Enzymes include but are not limited to collagenase, dispase, metalloproteinase, trypsin, telomerase, hyaluronidase, elastase, papain, pronase, and bromelain.

Inhibitors can include but are not limited to agents that are inhibit cell death or apoptosis, cell division, expression of specific genes, differentiation, senescence, or protein synthesis. Apoptosis inhibitors include but are not limited to agents known to inhibit caspases such as the Bcl-2 family, cytokine response modifier A (crmA) family, and inhibitors of apoptosis proteins (IAP) family.

Hormones include but are not limited to dexamethasone, Vitamin D (calcitriol), melatonin, calcitonin, epinephrine, insulin, leptin, progesterone, estrogen, and androgen.

Agents that induce expression of anti-microbial proteins include but are not limited to phenylbutyrate, Vitamin A, Vitamin D, cholic acid, chenodeoxycholic acid, lithocholic acid, sulforaphane, and retinoic acid.

Anti-inflammatory agents include but are not limited to curcumin, capsaicin, betaine, batalaine, aspirin, ibuprofen, naproxen, resolving, protectin, maresin, omega-3 fatty acids, and TGF-β.

Angiogenic agents include but are not limited to VEGF, PDGF, bFGF, TGF-β, placental growth factor (PlGF/PGF), angiopoietin (Ang)-2, angiogenin ephrin, and plasminogen activators.

Differentiation agents or differentiation-inducing factors include but are not limited to dexamethasone, β-glycerolphosphate, IBMX, indomethacin, β-mercaptoethanol, retinoic acid, BDNF, FGF, GDNF, SHH, forskolin, BMP, glucose, and insulin.

The TIMP (Tissue Inhibitor of Metalloproteinase) family can also be used as a stimulus. This family is related to tissue remodeling in wound healing. These include at least TIMP1, TIMP2, TIMP3, and TIMP4.

In some embodiments, suitable adipokines can include, for example, angiopoietin-1, angiopoietin-2, VEGF, transforming growth factor beta (TGF-β), hepatic growth factor (HGF), stromal derived growth factor 1 (SDF-1), TNF-α, resistin, leptin, tissue factor, placental growth factor (PGF), insulin like growth factor (IGF), and monobutyrin.

In some embodiments, suitable cytokines can include, for example, SDF-1a (stromal cell-derived factor 1), Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors.

In some embodiments, suitable growth factors can include, for example, BMP-2, rhBMP-2, BMP-4, rhBMP-4, BMP-6, rhBMP-6, BMP-7 [OP-1], rhBMP-7, GDF-5, Statin, LIM mineralization protein, Nel-1 protein, neural epidermal growth-factor-like 1 (Nel-like 1, NELL1), platelet derived growth factor (PDGF), vascular endothelial growth factor (VEGF), transforming growth factor-β (TGF-β), insulin-related growth factor-I (IGF-I), insulin-related growth factor-II (IGF-II), fibroblast growth factor (FGF), FGF-2, FGF-5, beta-2-microglobulin (BDGF II), and rhGDF-5.

In some embodiments, suitable hormones and steroids can include, for example, aldosterone, androstenedione, calcidiol, calcitriol, estradiol or estrogens, cortisol, dehydroepiandrosterone, dihydrotestosterone, testosterone, progesterone. Suitable hormones can include, for example, amylin, anti-Müllerian hormone, adiponectin, adrenocorticotropic hormone (or corticotropin), angiotensinogen, angiotensin, antidiuretic hormone (e.g., vasopressin, arginine vasopressin), atrial-natriuretic peptide (e.g., atriopeptin), brain natriuretic peptide, calcitonin, cholecystokinin, corticotropin-releasing hormone, cortistatin, encephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, growth hormone, hepcidin, human chorionic gonadotropin, human placental lactogen, inhibin, insulin, insulin-like growth factor (or somatomedin), leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (or thyrotropin), thyrotropin-releasing hormone, or vasoactive intestinal peptide.

In some embodiments, the viable cells can be primed, by exposing the viable cells to various stimuli such as electrical or mechanical stress (e.g., fluid flow, substrate stiffness, topography, shear, matrix stretching, compression, torque), deprivation or supplementation of one or more nutrients (e.g., in medium), modulation of pressure, electromagnetic force, ultrasound, shockwave treatment, irradiation, change in temperature (e.g., temperature shock), pH (e.g., change in acidity or alkalinity) and atmospheric oxygen levels (e.g., hypoxia or hyperoxia) for a predetermined duration of time.

In some embodiments, exposure of viable amniotic membrane to hypoxic conditions (either by controlling atmospheric oxygen levels or adding substances to affect oxygen levels in the culture medium) can lead to accelerated angiogenic differentiation of the resident cells and result in more rapid healing when used treat, e.g., chronic wounds for the patient.

In some embodiments, the stimuli (physical or biochemical) can be applied in a static or dynamic fashion at the priming step. The stimuli can also be applied transiently (e.g., seconds or minutes) or for a prolonged period of time (e.g., 30 minutes to an hour, or hours or days). In some embodiments, the one or more stimuli may also be applied simultaneously, in sequence, or individually. The result of applying the processing conditions to the viable allogeneic cells will be to prime the cells to achieve an improved and/or more rapid therapeutic effect following transplantation.

Priming of viable cells can produce unexpected and advantageous results. For example, in some embodiments, priming of cells can result in cellular expression to produce a desired cell phenotype for use in therapeutic treatments. In some embodiments, priming of cells can result in faster cell differentiation of immature cells. In some embodiments, priming of cells can result in a greater percentage of immature cells that differentiate into target cells. In some embodiments, priming of cells can result in production of desired ECM. In some embodiments, priming of cells can result in the secretion of biochemical factors that enhance healing response. In some embodiments, priming of cells can result in the inhibition of apoptosis and improved cell viability. In some embodiments, priming of cells can result in the de-differentiation of mature or senescent cells. In some embodiments, priming of cells can promote or confer immunomodulatory, anti-infective properties, anti-inflammatory properties, and/or anti-scarring properties. In some embodiments, priming of cells can increase mobility of cells. In some embodiments, priming of cells can induce cellular reorganization. In some embodiments, priming of cells can induce cellular proliferation. In some embodiments, priming of cells can result in the restoration of proliferative and functional capacity to senescent cells either in the tissue or at the host site. In some embodiments, priming of cells can result in the selective elimination of senescent or otherwise undesired cells in the tissue. In some embodiments, priming of cells can reduce or inhibit innate immunoreactivity or inflammatory responses of tissues and/or organs.

The effects of cellular priming can be characterized by qualitative and quantifiable aspects of cellular physiology. For example, cellular priming can be evaluated by characteristics such as time to differentiation, percentage of differentiated cells, cell viability, cell proliferative activity, metabolic activity, cell morphology, epigenetic marker profile, surface marker expression, gene expression profiles, ECM production, secretion of biochemical factors, healing or remodeling in an in vitro or in vivo model, recruitment of host cells to defect site, modification of endogenous cell phenotypes, and/or modification of cell phenotypes at the host site in response to secreted factors/produced ECM.

In one example, a sample can be set aside in order to evaluate cell count and cell viability/biological activity of the tissue using commercially available methods, including but not limited to, for example, metabolic assays, such as involving luciferase, tetrazolium salts (e.g., 3-(4, 5-dimethyl-2-thiazolyl)-2, 5-diphenyl-2H-tetrazolium bromide (MTT), dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), and other water soluble tetrazolium salts (e.g., WST-1, -3, -4, -5, -8, -9, -10, and -11), live-dead assays, ATP assay, CCK-8 assay and dye exclusion assays such as Trypan Blue.

In some embodiments, cell priming or pre-conditioning could also be performed to counteract the negative effects that traditional processing methods and the time between recovery and processing would have on the allograft tissue and cells. For example, priming of viable cells can reduce the level of inflammation of the tissue upon implantation, thereby improving transplant acceptance and reducing patient recovery time. In addition, endogenous pre-conditioned cells could be directed to produce extracellular matrix or other biochemical factors that would be beneficial when introduced into the graft site in the patient. Priming can also reduce risk of infection, reduce risk of graft rejection, and/or reduce level of inflammation.

After priming, grafts containing primed cells could be provided either in a fresh or cryopreserved state to a patient. In some embodiments, immunoreactive cells may be removed from the graft while the cells of interest remain bound to the tissue. Methods of removal may be different for different tissue types. One exemplary method includes rinsing or soaking the tissue in a chemical solution for immunodepletion (e.g., the ProteoPrep® 20 Plasma Immunodepletion Kit from Sigma-Aldrich Co. LLC).

In one example, viable amniotic membrane for enhanced wound healing can be prepared by the following steps:
(1) Recover fresh amnion;
(2) Expose cells to hypoxic conditions for specific duration of time;
(3) Cryopreserve viable allograft or offer as fresh tissue; and
(4) Prepare/prime amnion cells for angiogenesis.

In another example, viable bone or periosteum for enhanced bone healing can be prepared by the following steps:
(1) Recover fresh cancellous or periosteum;
(2) Expose cells to osteogenic medium for specific duration of time;
(3) Cryopreserve viable allograft; and
(4) Prepare/prime amnion cells for osteogenesis.

In some embodiments, the cells can be strategically primed to produce beneficial soluble factors (e.g., adipokines, cytokines, growth factors, etc.) and/or extracellular matrix (ECM). In some embodiments, the primed cells contained within a tissue of interest can be at least partially decellularized or devitalized prior to implantation to a patient. The tissue (e.g., allograft) can then be primed for desired incorporation and remodeling, potentially without the need to maintain the living cells. In some embodiments, this can be used in off-the-shelf graft configurations. Without wishing to be bound by theory, one hypothesis is that the extracellular matrix and/or biochemical factors that the cells produced prior to decellularization or devitalization may still affect host cells following transplantation.

Decellularization is the removal of at least some of the endogenous cells and can optionally include killing of the cells. Any decellularization methods known in the art can be used. For example, a tissue can be treated by a solution containing detergents and/or hypotonic saline, to loosen and rinse off at least a portion of the cells in the tissue.

Devitalization is the killing of cells and could occur with or without cell removal. Any devitalization methods known in the art can be used in the preparation of, e.g., cell-free grafts. It aims to remove all or substantially all cellular material without adversely affecting the composition, mechanical integrity or biologic activity of the remaining ECM that carries specific properties. In some embodiments, physical treatment (e.g., freeze & thaw cycles, sonication, pressure, and mechanical agitation), enzymatic treatment (e.g., Trypsin) or chemical treatment (e.g., sodium deoxycholate, Triton X solutions, alcohol, peroxide, dilute acid) can be used to eliminate the living fraction from the primed tissue. Those methods should achieve preservation of the ECM properties while obtaining an efficient removal of the cellular component.

In certain embodiments, the resident cells can be primed to secrete biochemical factors and then leave behind residual amount of these factors which could, in turn, also elicit an enhanced healing response once the graft is applied to the patient. Secreted factors can include ECM components such as collagen(s), elastin, hydroxyapatite, proteoglycan, hyaluronan, fibronectin, and laminin. The collagen could be any type of collagen. Other factors secreted by primed cells can include angiogenic factors, mitogenic factors, osteogenic factors, adipogenic factors, chondrogenic factors, antimicrobial factors, and anti-inflammatory factors, including without limitation BMP, TGF-β, FGF, VEGF, PDGF, EGF, HGF, IGF, IL, β-defensin, insulin, ephrin, GDNF, GDF, NGF, KGF, TNF-α, TGF-α, interferon, EPO, albumin, transferrin, and SDF-1α.

In some embodiments, the resident cells can be primed to secrete biochemical agents or biochemically active factors into the medium surrounding the tissue. In this manner, a conditioned medium can be created that may utilized either directly or indirectly for therapeutic purposes. In some embodiments, the conditioned medium can be injected or applied to the targeted site within or on the body. In some embodiments, the conditioned medium can be applied to other viable cells (e.g., allogeneic, autogenic, xenogeneic) in order to stimulate a desired response (e.g., growth, migration, differentiation, de-differentiation, transdifferentiation) from these cells.

For example, to produce the conditioned medium, the resident cells can be cultured in a basal medium (e.g., DMEM (Dulbecco's modified Eagle's medium), optionally supplemented with serum, hormones, growth factors, cytokines, antibiotics, trace elements, and other additives. Growth factors that can be added include, but are not limited to, fibroblast growth factors (FGFs), epidermal growth factor (EGF), transforming growth factor-β (TGF-β), hepatocyte growth factor (HGF), neural epidermal growth-factor-like 1 (NELL-1), or oncostatin M. Additives to the medium may include insulin, transferrin, selenium, glucose, interleukin-6, and histone deacetylase inhibitor such as sodium butyrate or tricostatin A.

In some embodiments, the primed and/or conditioned tissue grafts or cells can be washed, rinsed, or otherwise exposed to solutions to prime the cells in the tissue grafts. In some embodiments, the primed and/or conditioned tissue grafts or cells can be washed, rinsed, or otherwise exposed to solutions to pre-condition the cells in the tissue grafts. In some embodiments, the primed and/or conditioned tissue grafts or cells can be washed, rinsed, or otherwise exposed to solutions to extend or decrease the viability of the cells resident in the tissue grafts, alter the cell adhesion characteristics of the cells in the tissue graft or the tissue graft itself, alter the cell proliferation of the cells resident in the tissue grafts, maintain the cell phenotype of the cells resident in the tissue graft, and/or alter the migration capability of cells resident in the tissue graft.

In some embodiments, the primed and/or conditioned tissue grafts or cell populations can be stored cryopreserved (e.g., ≤0° C.), optionally with cryopreservative solutions. In some embodiments, the primed and/or conditioned tissue grafts or cell populations can be stored frozen (e.g., ≤0° C.), optionally with preservative solution. In some embodiments, the primed and/or conditioned tissue grafts or cell populations can be stored at refrigerated temperatures (e.g., between 0° C.-10° C.), optionally with preservative solution. In some embodiments, the primed and/or conditioned tissue grafts or cell populations can be stored at room temperatures (e.g., between 10° C.-30° C.), optionally with preservative solution. In some embodiments, the primed and/or conditioned tissue grafts or cell populations can be stored at elevated temperatures (e.g., ≥30° C.), optionally with preservative solution.

In some embodiments, the primed and/or conditioned tissue grafts or cell populations that are stored under cryopreservation conditions are derived from fresh or previously frozen versions of one or more of the following: placenta, amnion, chorion, umbilical cord, Wharton's Jelly, bone, periosteum, cartilage, meniscus, spinal disc, muscle, tendon, ligament, adipose, skin, cardiovascular tissue, peritoneum, fascia, nerve, cornea, visceral organ, reproductive tissue, hair follicles, foreskin, and dental tissue.

In some embodiments, the primed and/or conditioned tissue grafts or cell populations that are stored under freezing conditions are derived from fresh or previously frozen versions of one or more of the following: placenta, amnion, chorion, umbilical cord, Wharton's Jelly, bone, periosteum, cartilage, meniscus, spinal disc, muscle, tendon, ligament, adipose, skin, cardiovascular tissue, peritoneum, fascia, nerve, cornea, visceral organ, reproductive tissue, hair follicles, foreskin, and dental tissue.

In some embodiments, the primed and/or conditioned tissue grafts or cell populations that are stored in refrigerated conditions are derived from fresh or previously frozen versions of one or more of the following: placenta, amnion, chorion, umbilical cord, Wharton's Jelly, bone, periosteum, cartilage, meniscus, spinal disc, muscle, tendon, ligament, adipose, skin, cardiovascular tissue, peritoneum, fascia, nerve, cornea, visceral organ, reproductive tissue, hair follicles, foreskin, and dental tissue.

In some embodiments, the primed and/or conditioned tissue grafts or cell populations that are stored at room temperature conditions are derived from fresh or previously frozen versions of one or more of the following: placenta, amnion, chorion, umbilical cord, Wharton's Jelly, bone, periosteum, cartilage, meniscus, spinal disc, muscle, tendon, ligament, adipose, skin, cardiovascular tissue, peritoneum, fascia, nerve, cornea, visceral organ, reproductive tissue, hair follicles, foreskin, and dental tissue.

In some embodiments, the primed and/or conditioned tissue grafts or cell populations that are stored at elevated temperatures are derived from fresh or previously frozen versions of one or more of the following: placenta, amnion, chorion, umbilical cord, Wharton's Jelly, bone, periosteum, cartilage, meniscus, spinal disc, muscle, tendon, ligament, adipose, skin, cardiovascular tissue, peritoneum, fascia, nerve, cornea, visceral organ, reproductive tissue, hair follicles, foreskin, and dental tissue.

In some embodiments, the primed and/or conditioned tissue grafts or cells populations are allogenic to the recipient. In some embodiments, the primed and/or conditioned tissue grafts or cells populations are autogenic to the recipient. In some embodiments, the primed and/or conditioned tissue grafts or cells populations are xenogenic to the recipient.

EXAMPLES

Example 1—Osteogenic Differentiation of Amnion Tissue after Cryopreservation In this example, amnion tissue was analyzed to determine if the ability to undergo osteogenic differentiation can be retained following cryopreservation. The experiment was conducted according to the following procedure. Each donor was processed and cryopreserved for 1 month according to procedures previously outlined. Briefly, the amnion was separated, washed, and cut into 2×2 cm sheets. Each sheet was packaged into a separate vial, cryopreserved, and placed into vapor phase liquid nitrogen storage for 1 month. At the 1 month time point, a vial from the corresponding donor were removed from the vapor phase liquid nitrogen storage tank (cryotank) and placed into the 37° C. water bath to thaw. The cryoprotectant solution was decanted by gently inverting the vial. Dextrose solution (5%) was added to the vial and the vial was left without agitation for 5 minutes. After 5 minutes, the vial was inverted to remove the dextrose solution. The amnion sheet was picked up from the mesh material with forceps and carefully cut into 4 equal pieces approximately 1×1 cm each and each was placed into a well of a 24 well plate. Complete DMEM/F12 media was added to each of the wells containing amnion tissue. The media in the wells was changed with fresh complete DMEM/F12 media every 3-4 days. After 2 weeks in complete DMEM/F12 media, the media in 3 of the 4 wells was switched to complete osteogenic media and changed with fresh media every 3-4 days, while the 4th well was kept in DMEM/F12 media as a negative control.

At each time point (2, 4, and 6 weeks of osteogenic media) one amnion piece cultured in osteogenic media was collected and placed into a vial of formalin and fixed overnight. The control well's tissue sample was collected at the 6 week time point. After fixation, the sample was placed into 75% ethanol for storage. The amnion samples were analyzed for Alizarin Red, Von Kossa, and hematoxylin and eosin (H&E) staining. The Alizarin Red and Von Kossa slides were analyzed for indications of mineralization in the tissue and the H&E slides were analyzed for differences in cell presence in the tissue.

The DMEM/F12 Growth Medium used in the study was generated using the following protocol. EGF and bFGF were reconstituted per manufacturer's instructions and stored in the −20° C. freezer. DMEM/F12 basal media was supplemented with 1% PenStrep, 1% Glutamax, and 10% HI-FBS final v/v, then sterile filtered and stored refrigerated in the dark. Complete DMEM/F12 was made by adding 0.1% EGF and 0.1% bFGF v/v to supplement DEMEM/F12 immediately before use.

Complete Osteogenic Media used in the study was generated using the following protocol. Dexamethasone was dissolved in a small volume of absolute ethanol then added to absolute ethanol to a final volume of 25.5 mL ($10^{-4}$M stock concentration). Ascorbic acid was dissolved in 10 mL of MesenCult™ MSC Basal Medium (10 mg/mL stock concentration). Osteogenic Stimulatory Supplements, β-glycerophosphate, dexamethasone, and ascorbic acid were aliquotted per manufacturer's instructions. The following components were added to 42 mL of Mesenult MSC Basal Medium: 7.5 mL osteogenic stimulatory supplements, 54, dexamethasone, 2504, ascorbic acid, 1754, β-glycerophosphate, and 0.5 mL PenStrep. The complete Osteogenic Media was stored refrigerated in the dark.

The amnion tissue samples were cultured in complete DMEM/F12 growth media for 2 weeks in order to help the cells recover from the freezing and thawing process. The osteogenic and control time points were started on the date when the test tissue samples were first switched to complete osteogenic media.

The post-cryo amnion tissue showed positive Alizarin Red and Von Kossa staining as early as 2 weeks in culture with osteogenic media. The stained portions were relatively small and dispersed throughout the tissue. By 4 weeks, the stained mineralized portions of tissue were larger and more prevalent throughout the tissue. Week 6 was also comparable, with continuous sections of tissue stained positive with Alizarin Red and Von Kossa and some large nodules visible indicating highly mineralized areas. In both the case of Alizarin Red and Von Kossa staining, the stains appear to localize more at the surfaces of the amnion sheet than in the interior of the sheet tissue. This is especially apparent in the Von Kossa staining, as the Alizarin Red staining forms larger clumps of red positive staining.

Staining the control tissue at 6 weeks showed no Alizarin Red or Von Kossa staining in the tissue besides some artifacts of the staining process. Though there is only one control time point, the lack of positive staining after 6 weeks of culture implies that earlier time points also do not have positive staining for mineralization. Thus it can be concluded that amnion from this donor was capable of osteogenic differentiation when cultured in osteogenic media after cryopreservation and storage in vapor phase liquid nitrogen for 1 month.

Figure 2A:
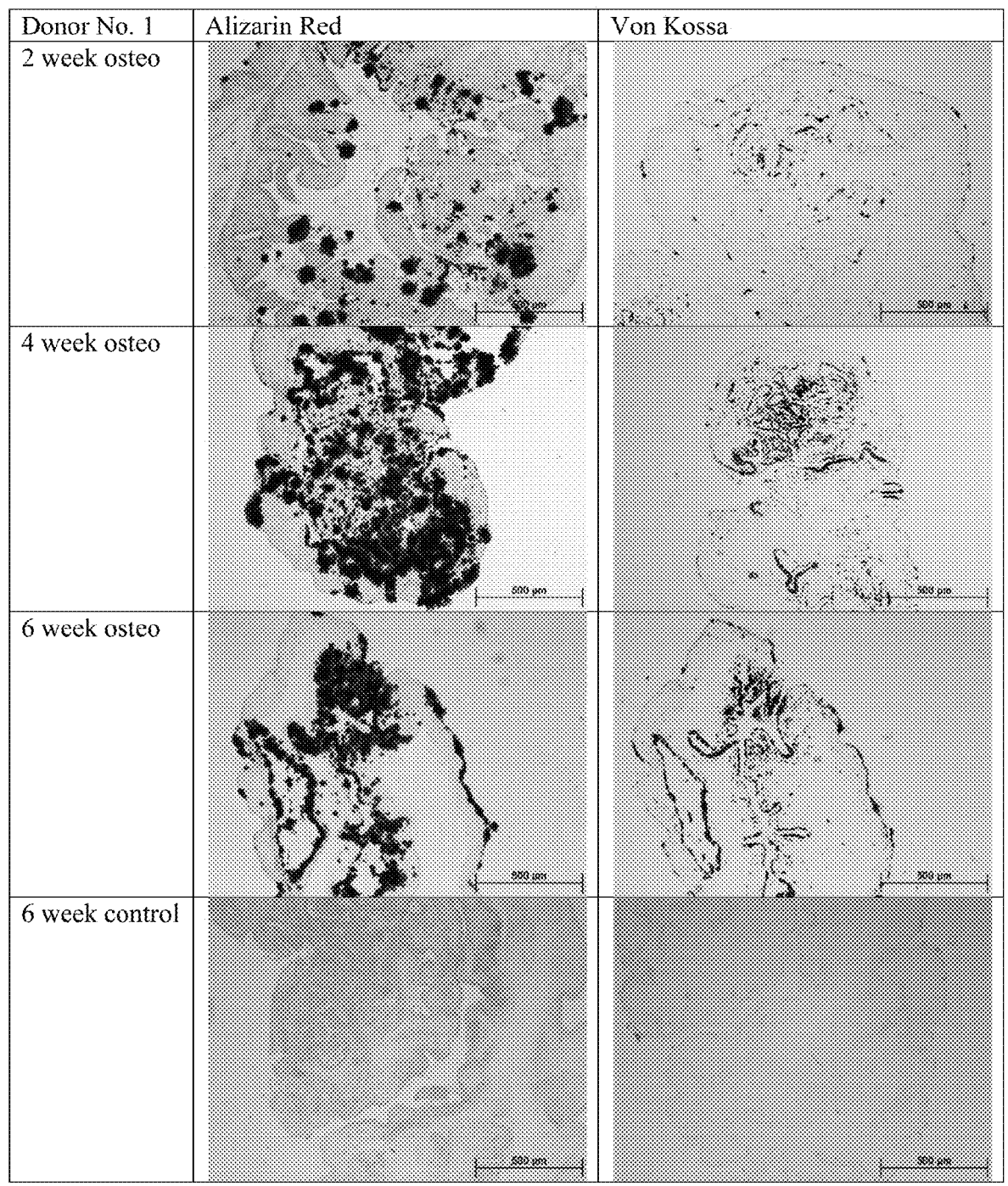

FIG. 2A illustrates Alizarin Red and Von Kossa staining of post-cryo amnion tissue of one donor in osteogenic or control culture conditions at 2, 4, and 6 week time points. Alizarin Red and Von Kossa staining was present in all three time points and not in the control tissue after 6 weeks in control growth media. The images were obtained at 10× magnification.

The post-cryo amnion tissue from another donor cultured in osteogenic media also exhibited positive Alizarin Red and Von Kossa staining at the first time point, 2 weeks. The intensity and size of the mineralized nodules indicated by Alizarin Red increases over time, with the 6 week tissue nearly completely mineralized at the epithelial surfaces of the tissue. Likewise, the Von Kossa staining at 6 weeks is ubiquitous and indicates significant mineralization throughout the tissue. The stains of both the Alizarin Red and Von Kossa are present at nearly all of the outer surfaces of the sheet tissue, though the interior portions of tissue are not all positively stained by Alizarin Red or Von Kossa.

Again, the control tissue at 6 weeks showed no Alizarin Red or Von Kossa staining. The amnion tissue from this donor was demonstrated to be capable of osteogenic differentiation after cryopreservation and storage in vapor phase liquid nitrogen for 1 month.

Figure 2B:
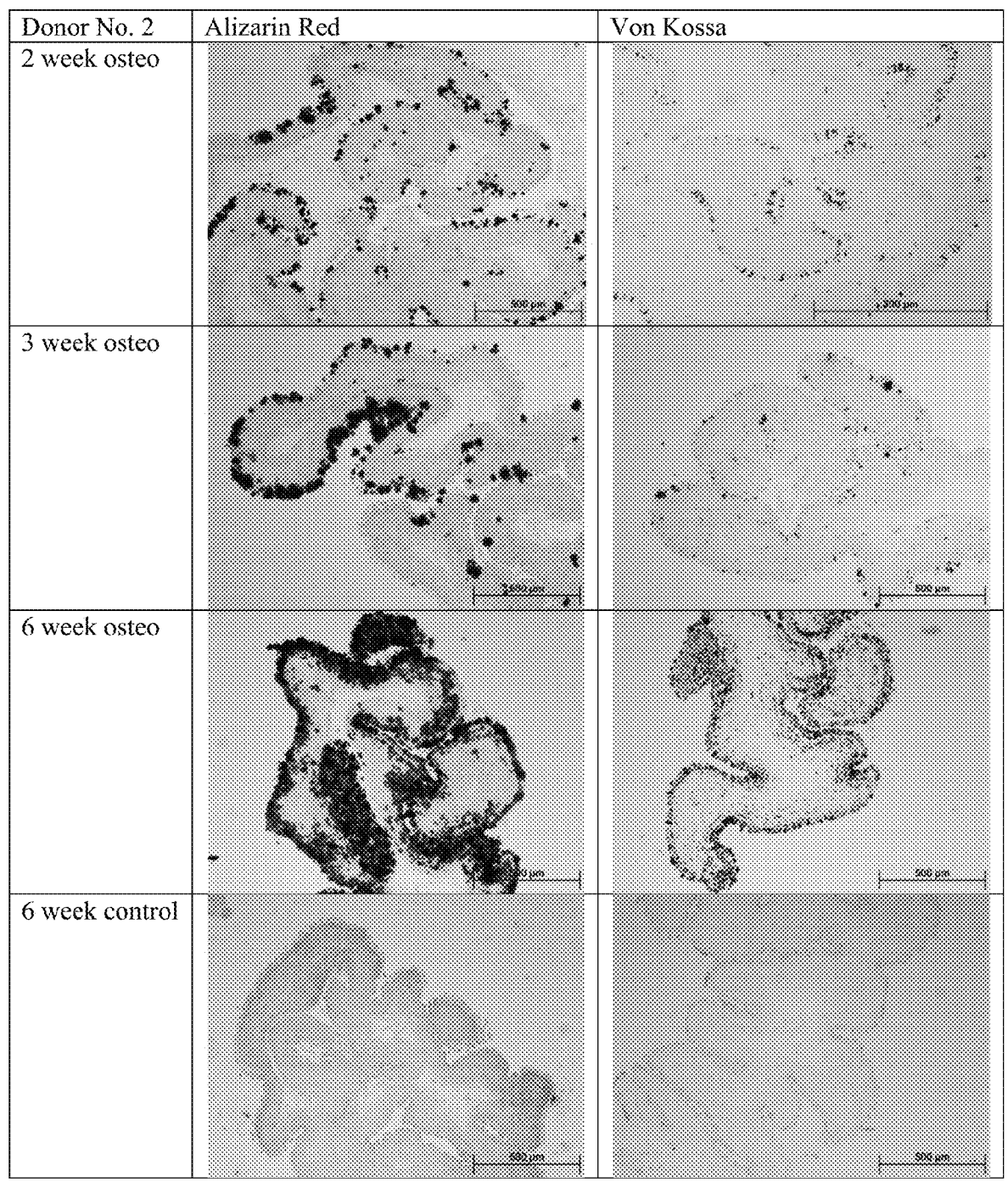

FIG. 2B shows Alizarin Red and Von Kossa staining of post-cryo amnion tissue of another donor in osteogenic or control culture conditions at 2, 3, and 6 week time points. Alizarin Red and Von Kossa staining was present in all three time points and not in the control tissue after 6 weeks in control growth media. The images were obtained at 10× magnification.

FIG. 2C illustrates the H&E staining of post-cryo amnion tissues of two donors in osteogenic or control culture conditions at all time points. The images were obtained at 40× magnification. The H&E staining of the post-cryotank amnion sheets showed cells present in the tissue at all time points except the 2 week time point for one donor. It is unknown why no cells are visible at all at this time point, as the corresponding Alizarin Red and Von Kossa slides show positive staining indicative of mineralization, and later time points show increased staining in the tissue. At 4 and 6 week time points for the osteogenic media cultured sheets, mineralization can be observed in the H&E slides by the dark purple nodules visible near the tissue surfaces for both donors.

In conclusion, cryopreserved samples of amnion sheets from two donors were successfully cultured in osteogenic media for 2, 4, and 6 weeks and shown to exhibit mineralization at all time points by positive staining of Alizarin Red and Von Kossa. Control sheets cultured in complete DMEM/F12 media displayed no positive staining of either Alizarin Red or Von Kossa at 6 weeks. H&E staining showed that cells were still present in the sheets after 6 weeks in osteogenic media. The positive Alizarin Red and Von Kossa staining indicate that the cryopreserved sheets from both donors were capable of undergoing direct tissue osteogenic differentiation after storage in vapor phase liquid nitrogen for 1 month after thawing and culturing in growth media for 2 weeks to allow the cells within the tissue to recover from the freezing and thawing procedures.

Example 2—Osteogenic Differentiation of Fresh Amnion and Chorion Tissue

In this example, fresh amnion and chorion tissue was analyzed to determine if the tissues can undergo direct osteogenic differentiation after culturing in osteogenic media for 4, 6, or 8 weeks. The experiment was conducted according to the following procedure.

The fresh amnion and chorion osteogenic differentiation cultures were initiated in according to established protocols in Example 1. Briefly, there were two test and one control minced amnion wells for each of three time points, and one test minced chorion well for each of three time points with one control well overall. Pieces of tissue from the chorion control well were planned to be collected at each time point, effectively allowing a control sample for comparison at each time point.

The media in the wells was changed with fresh complete osteogenic media (for test tissue wells) or complete DMEM/F12 media ("growth media" for control tissue wells) every 3-4 days. At each time point (4, 6, and 8 weeks of osteogenic media) the corresponding amnion and chorion test and control tissue was collected and fixed in separate vials of formalin overnight. Several minced tissue pieces from the chorion control well's tissue were collected at each time point as representative control tissue. After fixation, the sample was placed into 75% ethanol for storage. The samples were analyzed for Alizarin Red, Von Kossa, and hematoxylin and eosin (H&E) staining. The Alizarin Red and Von Kossa slides were analyzed for indications of mineralization in the tissue and the H&E slides were analyzed for differences in cell presence in the tissue. Complete DMEM/F12 and osteogenic media was generated according to procedures outlined in Example 1.

By 4 weeks, tissue from one of the amnion minced test wells showed positive Alizarin Red and Von Kossa staining, while the other test well had much weaker staining. Again at 6 weeks, one test well tissue sample had stronger positive Alizarin Red and Von Kossa staining than tissue from the second test well. However, by week 8 both amnion test well samples had similarly strong Alizarin Red and Von Kossa staining while the control well tissue remained negative.

Overall, osteogenic differentiation is demonstrated in fresh minced amnion tissue by 8 weeks with some differences in differentiation kinetics. The control wells did not show any significant positive staining at any time.

Figure 3A:
Figure 3A:
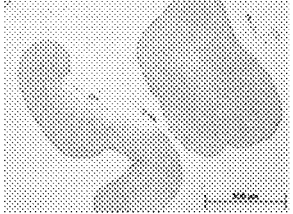
Figure 3A:
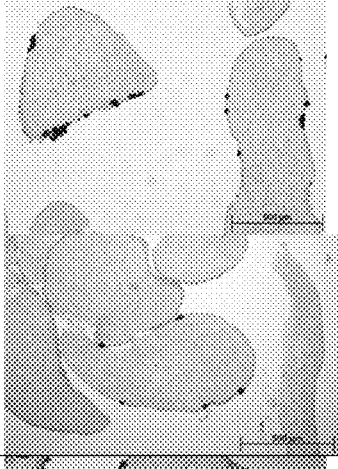
Figure 3A:
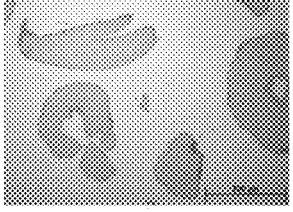
Figure 3A:
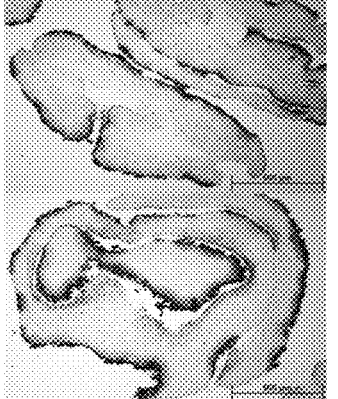
Figure 3A:
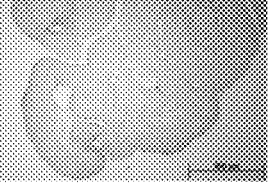

FIG. 3A illustrates Alizarin Red staining of fresh minced amnion tissue in osteogenic or control culture conditions at 4, 6, and 8 week time points. Positive staining was visible in test tissue at all three time points, and not in the control tissue at any time point. One representative image from each of two test wells shown at each time point. The images were obtained at 10× magnification.

Figure 3B:
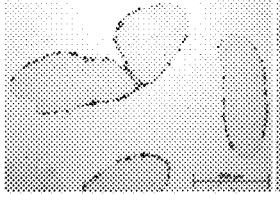
Figure 3B:
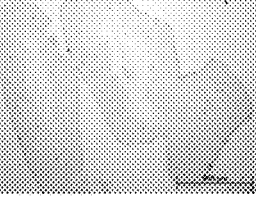
Figure 3B:
Figure 3B:
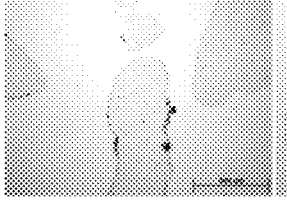
Figure 3B:
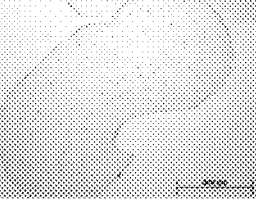
Figure 3B:
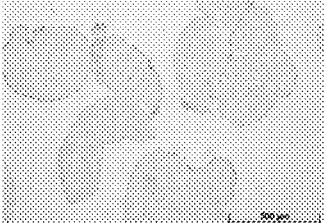
Figure 3B:
Figure 3B:
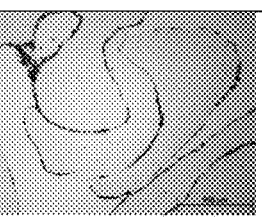
Figure 3B:
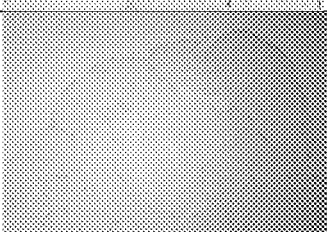

FIG. 3B illustrates Von Kossa staining of fresh minced amnion tissue in osteogenic or control culture conditions at 4, 6, and 8 week time points. Positive staining was visible in test tissue at all three time points, and not in the control tissue at any time point. One representative image from each of two test wells shown at each time point. The images were obtained at 10× magnification.

FIG. 3C illustrates H&E staining of fresh minced amnion tissue in osteogenic or control culture conditions at 4, 6, and 8 week time points. One representative image from each of two test wells shown at each time point at 40× magnification. The H&E staining of the fresh minced amnion tissue showed cells present in the tissue at all time points, both in the epithelial layer as well as in the stromal layer below. There are no major differences in cell numbers or distribution between the control and test well tissue samples, nor between different time points. However, nodules of H&E staining indicating mineralization can be observed in the epithelial layer of tissue cultured in osteogenic media. The H&E nodules are further supporting evidence that the minced tissue in osteogenic media underwent osteogenic differentiation over the course of the study.

Figure 3D:
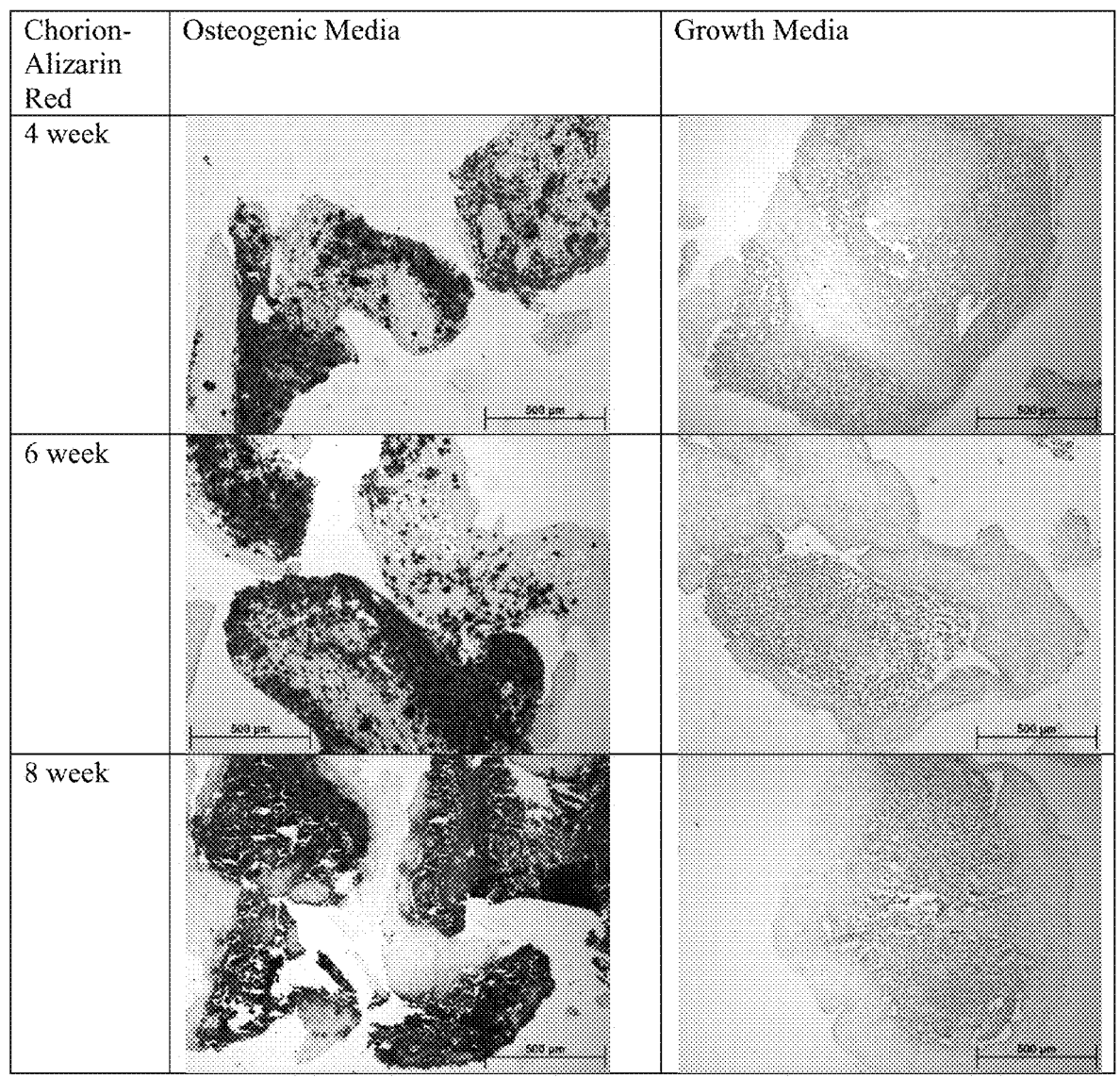

FIG. 3D illustrates Alizarin Red staining of fresh minced chorion tissue in osteogenic or control culture conditions at 4, 6, and 8 week time points. Positive staining was visible in test tissue at all three time points and increases over time while control remains negative at all time points. The images were obtained at 10× magnification.

By 4 weeks, tissue from the test well containing minced chorion tissue showed strong positive Alizarin Red and Von Kossa staining, permeating throughout the tissue interior. The staining was not evenly distributed but was rather concentrated in some areas and negative in others. Areas with many cells tended to have strong staining, whereas areas relatively devoid of cells did not have any positive staining. The relative intensity and amount of positive Alizarin Red and Von Kossa staining increased from the 4 week to 8 week time point. While early staining showed small concentrations of positive Alizarin Red or Von Kossa, the 8 week had nearly solid red portions of tissue completely stained with Alizarin Red and large swatches of dense Von Kossa staining, indicating very strong mineralization in large portions of the tissue. Areas that are not stained either had few or no cells visible, suggesting that only relatively acellular areas were not mineralized by 8 weeks. The control well tissue did not show any significant positive staining at any time.

The intensity and extent of mineralization in the chorion appears to be stronger than that of the amnion, with positive staining that was not limited to the tissue surface. The chorion can thus be concluded to have successfully undergone osteogenic differentiation in this tissue differentiation study.

Figure 3E:
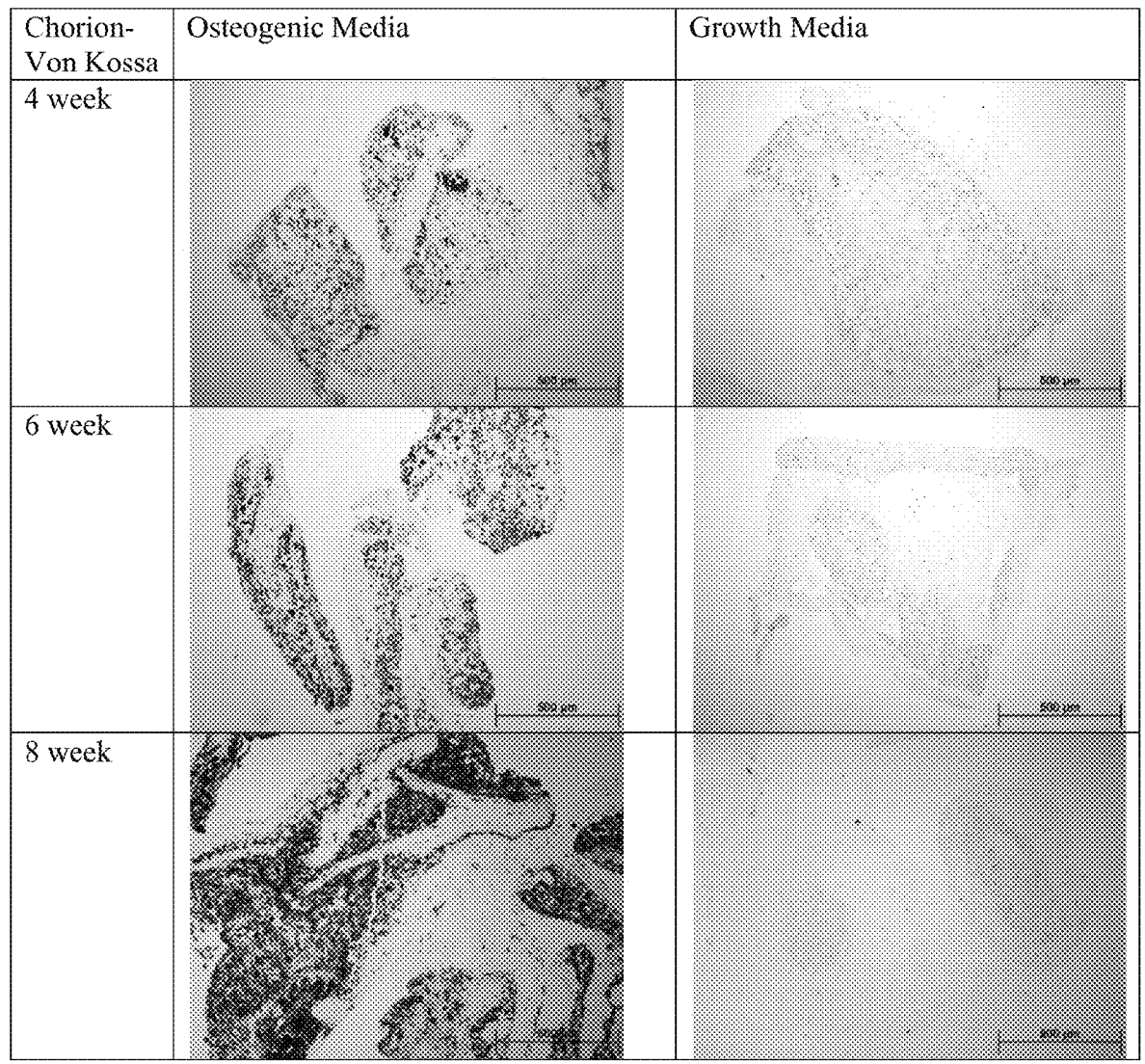

FIG. 3E illustrates Von Kossa staining of fresh minced chorion tissue in osteogenic or control culture conditions at 4, 6, and 8 week time points. Positive staining was visible in test tissue at all three time points and increases over time while control remains negative at all time points. Images were obtained using a 10x objective.

Figure 3F:
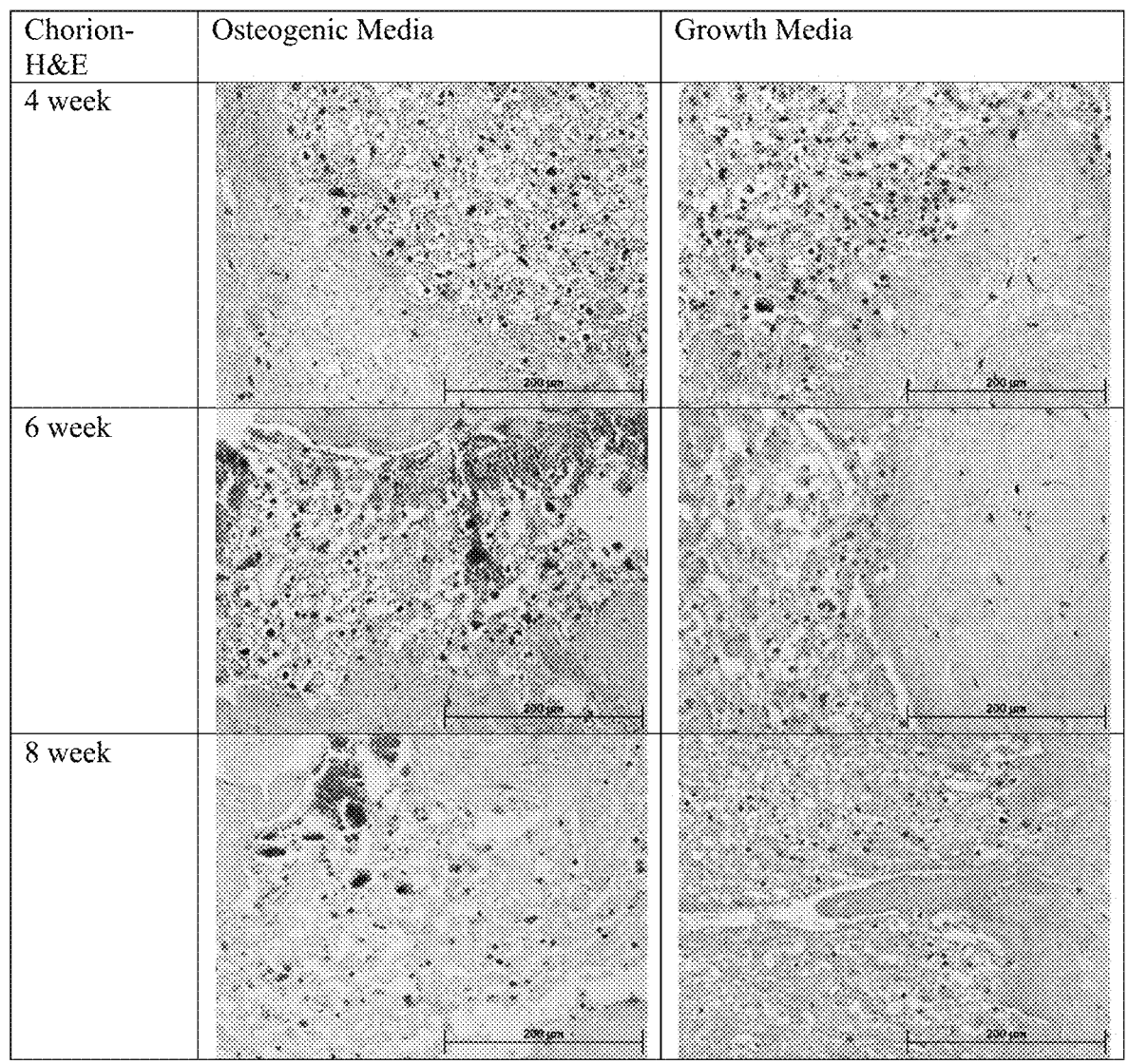

FIG. 3F illustrates H&E staining of fresh minced chorion tissue in osteogenic or control culture conditions at 4, 6, and 8 week time points. Images were obtained at 40× magnification. The H&E staining of the fresh minced chorion tissue revealed at least two distinct regions of chorion: a dense layer of matrix with cell distribution similar to that of the stromal layer in amnion and a looser layer mostly consisting of cells. Over the three time points, the dense layer did not appear to change significantly in either the osteogenic or control media wells. The looser layer of cells, on the other hand, mineralized in osteogenic media over time which was visualized by the nodules of H&E.

In conclusion, the fresh minced tissue samples of amnion and chorion were successfully cultured in osteogenic media for 4, 6, and 8 weeks and generally demonstrated to have mineralization at each time point by positive staining of Alizarin Red and Von Kossa. Control wells of minced amnion and chorion cultured in complete DMEM/F12 media demonstrated no positive staining of either Alizarin Red or Von Kossa at any time point. H&E staining showed that cells were still present in the test and control tissue samples after 8 weeks in osteogenic media. The positive Alizarin Red and Von Kossa staining indicated that the fresh minced tissue from both amnion and chorion was capable of undergoing direct tissue osteogenic differentiation. There was some variability in the amount of mineralization present between amnion samples over time, but the chorion tissue was strongly osteogenic and had increasingly intense positive staining over time.

Example 3—Osteogenic Differentiation Potential of Amnion and Chorion Tissue after Cryopreservation In this example, amnion and chorion tissue was analyzed to determine if the tissues can undergo osteogenic differentiation after 1 month of cryopreservation. The experiment was conducted according to the following procedure.

Tissue from each donor was processed and cryopreserved according to procedures disclosed herein. Briefly, the amnion and chorion membranes were separated, washed, and cut into 2×2 cm sheets. Each sheet was minced and the minced pieces packaged into a separate cryovial, cryopreserved, and placed into liquid nitrogen storage for 1 month. At the 1 month time point, the vials were removed from the vapor phase liquid nitrogen storage tank (cryotank) and placed in a floater into the 37° C. water bath to thaw. The cryoprotectant solution was decanted by gently inverting the vial. 5% dextrose solution was added to the vial until full and the vial was left without agitation for 5 minutes. After 5 minutes, the vial was inverted to remove the dextrose solution and the tissue was transferred into a well plate. The well plate was gently shaken by hand to slightly disperse the minced tissue pieces and a sterile mesh was placed into each well to keep the pieces from floating around.

Complete DMEM/F12 media was added to each of the wells containing amnion tissue. The media in the wells was changed with fresh complete DMEM/F12 media every 3-4 days. After 2 weeks in DMEM/F12 media, the media in 3 of the 4 wells was switched to complete osteogenic media and changed with fresh media every 3-4 days, while the 4th well was kept in DMEM/F12 media as a negative control. At each time point (2, 4, and 6 weeks of osteogenic media) one amnion piece cultured in osteogenic media was collected and placed into a vial of formalin and fixed overnight. The tissue sample in the control well was collected at the 6 week time point. After fixation, the sample was placed into 75% ethanol for storage. The amnion samples were analyzed for Alizarin Red, Von Kossa, and hematoxylin and eosin (H&E) staining. The Alizarin Red and Von Kossa slides were analyzed for indications of mineralization in the tissue and the H&E slides were analyzed for differences in cell presence in the tissue. Complete DMEM/F12 and osteogenic media were generated according to procedures outlined in Example 1.

By 2 weeks, positive Alizarin Red and Von Kossa staining were visible in the amnion tissue, though there was variability between the duplicate test tissue samples in the intensity of Alizarin Red staining. Overall the strongest Alizarin Red staining was observed at the last time point, 6 weeks, while Von Kossa staining was strong throughout the time points. Both Alizarin Red and Von Kossa stains were mostly constrained to the epithelial layer, with some stromal layer Alizarin Red staining at 6 weeks. These observations were corroborated by the H&E staining which shows mineralized nodules in the 6 week osteogenic media tissue along the epithelial layer but less mineralization in the stromal layer. At all time points and for both the osteogenic and growth media tissue, cells could be observed in both the epithelial layer as well as in the stromal layer of amnion.

Overall, osteogenic differentiation was demonstrated in the post-cryopreservation (postcryo) minced amnion tissue by 2 weeks with an increase in stain intensity from weeks 2 to 6. The Von Kossa staining also appeared to be more ubiquitous than Alizarin Red, staining nearly the entirety of the epithelial layer of amnion while Alizarin Red staining was more local and occurred in nodules rather than staining positive in the entire epithelial surface. The control wells did not show any significant positive staining at any time. The trend of osteogenic differentiation seemed to be similar to that of fresh minced amnion, with weaker staining in the beginning that increases over time. However, the postcryo minced amnion had stronger Von Kossa staining earlier than fresh minced amnion as well as stronger Alizarin Red staining at 6 weeks though the fresh minced amnion at 8 weeks ultimately has the strongest Alizarin Red staining (the postcryo study ended at 6 weeks).

Figure 4A:
Figure 4A:
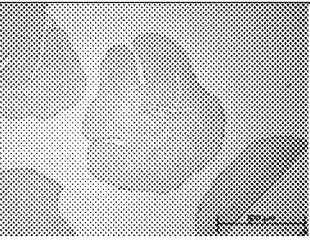
Figure 4A:
Figure 4A:
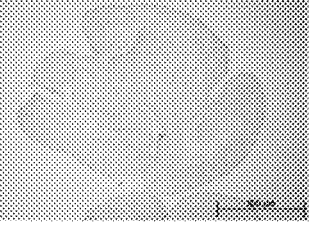
Figure 4A:
Figure 4A:
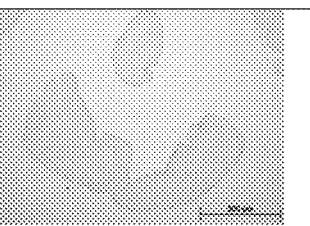
Figure 4B:
Figure 4B:
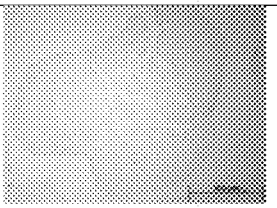
Figure 4B:
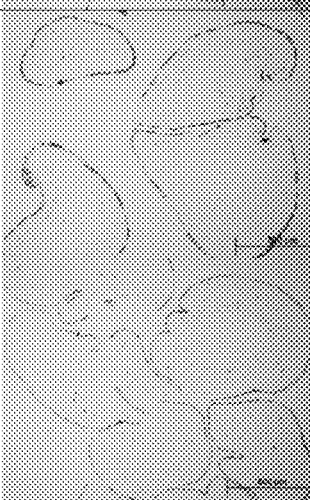
Figure 4B:
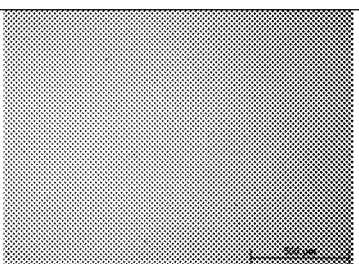
Figure 4B:
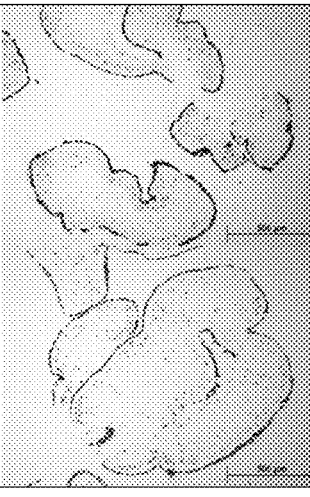
Figure 4B:
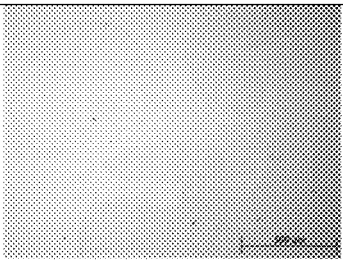

FIG. 4A illustrates Alizarin Red staining of postcryo minced amnion tissue in osteogenic or control culture conditions at 4, 6, and 8 week time points. Positive staining was visible in test tissue at all three time points, and not in the control tissue at any time point. One representative image from each of two test wells shown at each time point. Images were obtained at 10× magnification. FIG. 4B illustrates Von Kossa staining of postcryo minced amnion tissue in osteogenic or control culture conditions at 2, 4, and 6 week time points. Positive staining was visible in test tissue at all three time points, and not in the control tissue at any time point. One representative image from each of two test wells is shown at each time point. Images were obtained at 10× magnification.

Figure 4C:
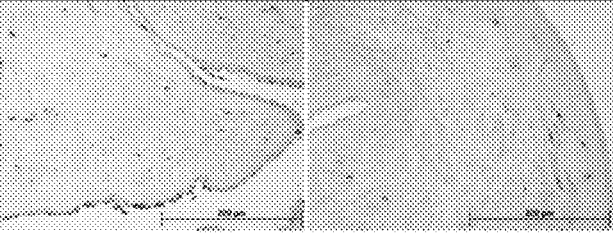
Figure 4C:
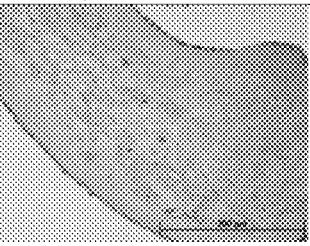
Figure 4C:
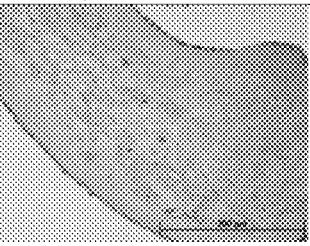
Figure 4C:
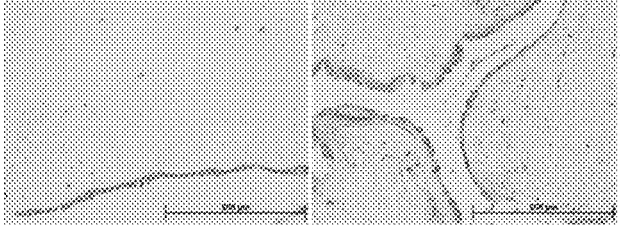
Figure 4C:
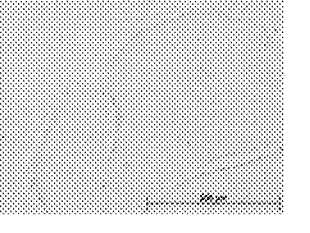
Figure 4C:
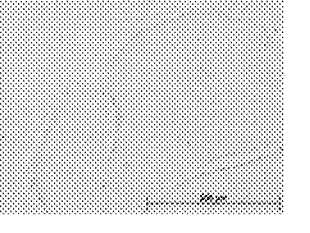
Figure 4C:
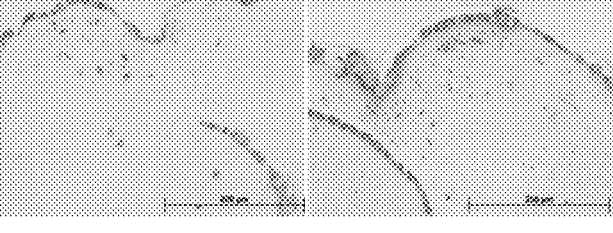
Figure 4C:
Figure 4C:

FIG. 4C illustrates H&E staining of postcryo minced amnion tissue in osteogenic or control culture conditions at 2, 4, and 6 week time points. One representative image from each of two test wells is shown at each time point. Images were obtained at 40× magnification.

By 2 weeks, positive Alizarin Red and Von Kossa staining were visible in the chorion tissue. Interestingly, week 4 staining showed significantly less Alizarin Red and Von Kossa staining, with one of two test tissue samples having effectively no positive Alizarin Red or Von Kossa staining at all when compared to the corresponding control tissue. At week 6, one of the Alizarin Red stains remained negative while the other test sample stained strongly for Alizarin Red, more so than week 2 samples. The Von Kossa stain also increased from week 4 to 6, with both test tissue samples showing levels of staining stronger than week 2 samples. The H&E stains showed cells present in the chorion throughout the time points, with nodules of mineralization observed in the week 4 samples. Week 6 had significant mineralization visible, as expected of the time point with the strongest Alizarin Red and Von Kossa staining.

Overall, osteogenic differentiation is demonstrated in the postcryo minced chorion tissue by 2 weeks with an increase in stain intensity from weeks 2 to 6. The control wells did not show any significant positive staining at any time. Compared to the fresh minced chorion, the stains at each postcryo time point were weaker than the corresponding stains at the fresh time point, with the exception of Von Kossa at 6 weeks where the stains were relatively similar. Whereas fresh minced chorion had noticeably much stronger osteogenic differentiation than fresh amnion tissue, the difference between the two tissues postcryo was less pronounced.

Figure 4D:
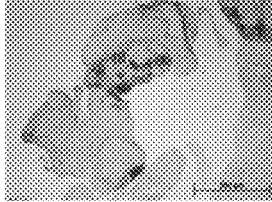
Figure 4D:
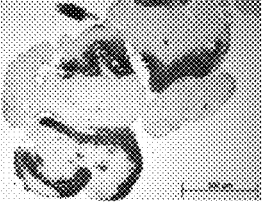
Figure 4D:
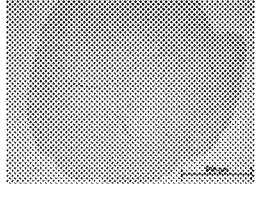
Figure 4D:
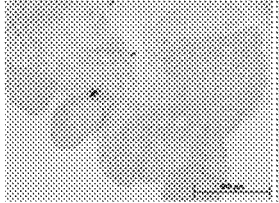
Figure 4D:
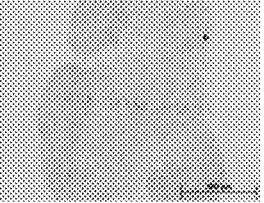
Figure 4D:
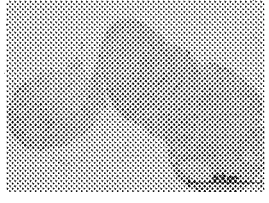
Figure 4D:
Figure 4D:
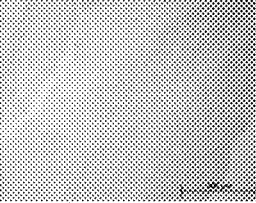
Figure 4D:
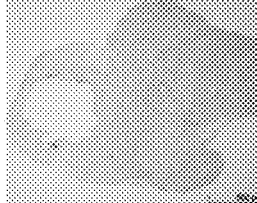

FIG. 4D illustrates Alizarin Red staining of fresh minced chorion tissue in osteogenic or control culture conditions at 2, 4, and 6 week time points. One representative image from each of two test wells is shown at each time point. Images were obtained at 10× magnification.

FIG. 4E illustrates Von Kossa staining of fresh minced chorion tissue in osteogenic or control culture conditions at 2, 4, and 6 week time points. Positive staining is present at all three time points while control remains negative at all time points. One representative image from each of two test wells is shown at each time point. Images were obtained at 10× magnification.

Figure 4F:
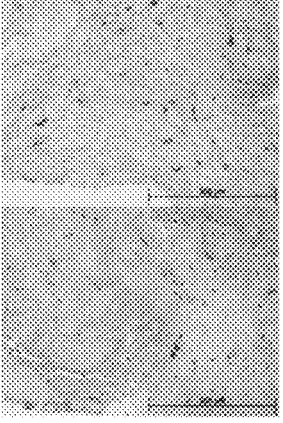
Figure 4F:
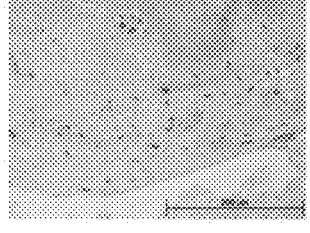
Figure 4F:
Figure 4F:
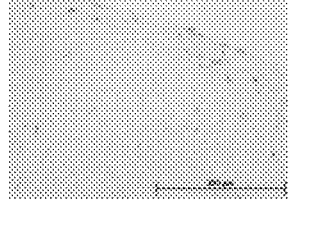
Figure 4F:
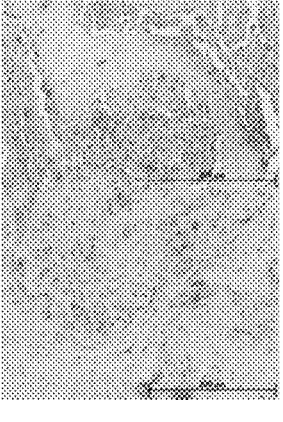
Figure 4F:
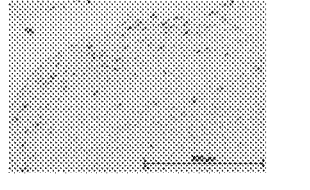

FIG. 4F illustrates H&E staining of fresh minced chorion tissue in osteogenic or control culture conditions at 2, 4, and 6 week time points. One representative image from each of two test wells is shown at each time point. Images were obtained at 40× magnification.

In conclusion, postcryo minced tissue samples of amnion and chorion were successfully cultured in osteogenic media for 2, 4, and 6 weeks and demonstrated to have mineralization at the first time point by positive staining of Alizarin Red and Von Kossa. Control wells of minced amnion and chorion cultured in complete DMEM/F12 media exhibited no positive staining of either Alizarin Red or Von Kossa at any time point. H&E staining showed that cells were still present in the test and control tissue samples after 6 weeks in media, with mineralized nodules apparent in some of the test H&E slides. The positive Alizarin Red and Von Kossa staining indicate that the postcryo minced tissue from both amnion and chorion was capable of undergoing direct tissue osteogenic differentiation. Both the amnion and chorion tissue had weaker staining compared to that of fresh tissue though the chorion had a relatively larger decrease from fresh to postcryo tissue staining of both Alizarin and Von Kossa.

Example 4—Chondrogenic Potential of Amnion Cells

In this example amnion tissues were utilized to investigate the chondrogenic differentiation potential of the cells in various configurations (e.g., minced, sheet). These experiments were conducted according to the following procedure.

In one experiment, amnion tissue from a placental donor was minced and transferred with forceps into a tissue culture (TC)-treated 24 well plate. There were 3 pieces of minced tissue total, with each piece of minced tissue placed into a separate well. The planned time point was 4 weeks. In a second experiment, minced tissue pieces from a different donor amnion were transferred with forceps into 2 TC-treated 48 well plates. Each well plate had 3 minced tissue pieces each in separate wells. One extra piece of minced tissue was available, and was placed into one of the well plates in a separate well for a third time point. The planned time points were 2 weeks and 4 weeks, with an extra minced piece planned for 6 weeks. For both experiments, cells were fed with complete chondrogenic media, replaced every 3-4 days. At each time point, each of the corresponding minced tissue pieces were removed from the well plates with forceps and placed into separate microcentrifuge tubes with 10% neutral buffered formalin (enough to cover the tissue) to fix for 3 days. After 3 days, each minced tissue piece was transferred with forceps into new separate microcentrifuge tubes with 70% ethanol (enough to cover the tissue) for storage until sent to a histology lab for Safranin 0 staining. Slides sent from the histology lab were analyzed for positive Safranin 0 staining, a solid red/orange-red color.

Complete Lonza Chondrogenic Media for the experiment was generated using the following procedure. First, TGF-β1 was reconstituted per manufacturer's instructions and stored in the −20° C. freezer. Next the contents of each component in the Chondrogenic SingleQuots kit except GA-1000 were added to 185 mL of basal medium per manufacturer's instructions. Then 1% PenStep final v/v was substituted for the GA-1000 (gentamycin). The supplemented Chondrogenic Media was then stored refrigerated in the dark. Immediately before chondrogenic medium was used, TGF-β1 was added to the medium at 0.05% v/v to make complete chondrogenic media.

Figure 5A:
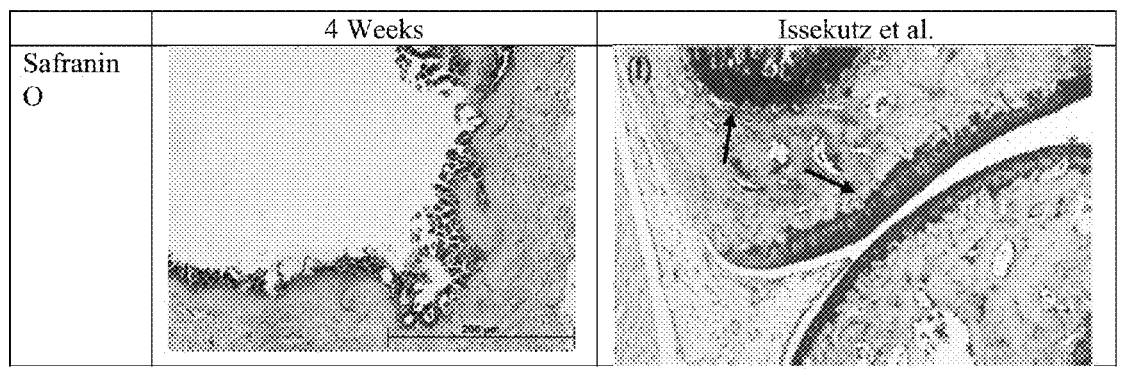
FIGS. 5A-5B illustrate chondrogenic differentiation of isolated amnion cells in various configurations.

As illustrated in FIG. 5A, from the first experiment, Safranin 0 staining was observed along the periphery of the tissue after chondrogenic differentiation of minced amnion tissue. The color does appear to be similar to images of positive Safranin 0 staining (FIG. 5A, arrows) as reported by Issekutz et al. Immunol Cell Biol. 2003 October; 81(5):397-408.

Figure 5B:
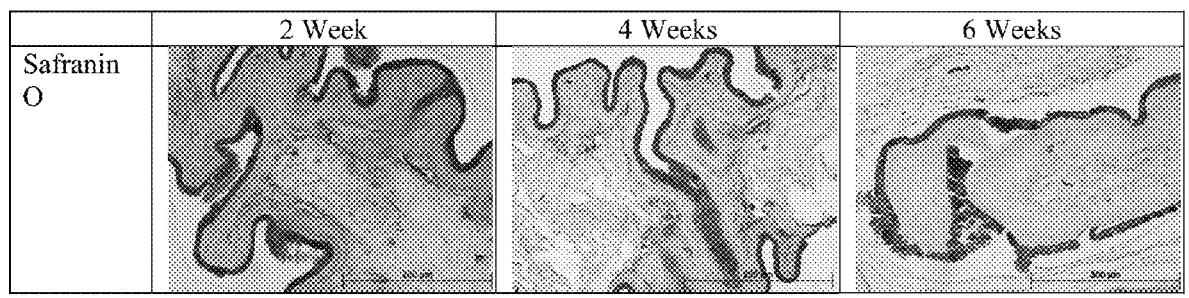

From the second experiment, there appears to be positive Safranin 0 staining at the periphery of the minced amnion tissue following chondrogenic differentiation, as illustrated in FIG. 5B. There does not seem to be significant differences in the amount of positive Safranin O staining between the three time points.

In conclusion, the minced amnion tissue samples from two distinct donors appeared to have a detectable level of chondrogenic differentiation around the periphery of the tissue pieces, as suggested by positive Safranin O staining. Overall, this study demonstrated that amnion tissue is capable of undergoing chondrogenic differentiation.

Example 5—Osteogenic Differentiation Potential of Amnion Cells in Various Configurations In this example amnion cells were utilized to investigate the osteogenic differentiation potential of the cells in various configurations (e.g., monolayer, minced, sheet). The experiment was conducted according to the following procedures.

Monolayer Osteogenic Differentiation

First, cells isolated from a donor amnion were plated into 9 wells each of 3 TC-treated 24 well plates at 10,000 cells/cm2 (20,000 cells per well) for monolayer osteogenic differentiation. There were 9 seeded wells per well plate for n=3 for each of 3 different stains (Alizarin Red, von Kossa, Alkaline Phosphatase (ALP) stains) in triplicate. The planned time points were 2 weeks, 4 weeks, and 6 weeks. Amnion cells isolated from the same donor were plated into 9 wells each of 2 TC-treated 24 well plates at 20,000 cells per well. There were 9 seeded wells per well plate for n=3 for each of 3 different stains (Alizarin Red, von Kossa, Alkaline Phosphate (ALP) stains) in triplicate. The planned time points were 2 weeks and 4 weeks. All plates were fed with complete DMEM/F12, replaced every 3-4 days, until confluent. After the cells were confluent, wells were fed with complete osteogenic media without β-glycerophosphate, replaced every 3-4 days until evidence of cell multilayering was apparent through visual inspection by inverted microscope. After evidence of cell multilayering, all wells were switched to complete osteogenic media with β-glycerophosphate, replaced every 3-4 days. At each time point, the corresponding 24 well plate of cells was fixed and stained with Alizarin Red, von Kossa, and ALP (3 wells per stain). Von Kossa Staining Protocol 1 (see below for details) was followed for stains performed initially. Afterwards, Von Kossa Staining Protocol 2 (see below for details) was followed to obtain a darker stain color. Alkaline Phosphatase Staining Protocol 1 (see below for details) was followed for stains performed initially. Afterwards, Alkaline Phosphatase Staining Protocol 2 (see below for details) was followed.

Next, amnion cells isolated from a donor amnion were plated into 9 wells each of 3 TC-treated 24 well plates at 7,500 cells/cm2 (15,000 cells per well) to investigate mono layer osteogenic differentiation. There were 9 seeded wells per well plate for n=3 for each of 3 different stains (Alizarin Red, von Kossa, Alkaline Phosphatase (ALP) stains) in triplicate. The planned time points were 1 week, 2 weeks, and 4 weeks. However, due to reagent availability the 1 week time point was actually processed on day 9. Cells were plated at a lower density in order to decrease cell aggregation at the center of the wells previously evident after initial seeding of the amnion cells. All plates were fed with complete DMEM/F12, replaced every 3-4 days, until confluent. All wells were fed with complete osteogenic media without β-glycerophosphate, replaced every 3-4 days, until evidence of cell multilayering was apparent through visual inspection by inverted microscope. After evidence of cell multilayering, all wells were switched to complete osteogenic media with β-glycerophosphate, replaced every 3-4 days. At each time point, the corresponding 24 well plate was fixed and stained with Alizarin Red, von Kossa, and ALP (3 wells per stain). Von Kossa Staining Protocol 2 was followed. Alkaline Phosphatase Staining Protocol 2 was followed.

Minced Osteogenic Differentiation

Tissue from a donor amnion was minced and transferred from culture into 3 TC-treated 24 well plates. One piece of minced tissue was placed into each of 3 wells per plate for n=3. The planned time points were 2 weeks, 4 weeks, and 6 weeks. All wells were fed with complete osteogenic media with β-glycerophosphate, replaced every 3-4 days. At each time point, the corresponding 24 well plate was set aside for staining. Each minced tissue piece was placed into a microcentrifuge tube with 10% neutral buffered formalin for 3 days. After 3 days, each minced tissue piece was transferred into 70% ethanol for storage until sent to a histology lab for staining.

Sheet Osteogenic Differentiation

Amnion sheets from a placental donor were transferred from culture into a TC-treated 12 well plate. There were 2 sheets, each in a separate well. The end points for the experiment were 4 and 8 weeks. Sheets from another donor amnion were transferred from culture into a TC-treated 12 well plate. There were 2 sheets in separate wells. The planned time point was 4 weeks for both sheets. All wells were fed with complete osteogenic media with β-glycerophosphate, replaced every 3-4 days. At each time point, the corresponding 12 well plate was set aside for staining. Each sheet was placed into 10% neutral buffered formalin for 3 days. After 3 days, each sheet was transferred into 70% ethanol for storage until sent to a histology lab for staining.

Fixation and Staining

Tissue fixation was performed according to the following procedure. Media was aspirated from each well. Wells were washed twice with PBS to remove residual media. A 10% neutral buffered formalin was added to each well for 15 minutes to fix cells. After fixing, the formalin was removed from the wells and each well was washed twice in water.

Alizarin Red staining was performed according to the following procedure. A 2% Alizarin Red solution was prepared by mixing 2 g Alizarin Red in 100 mL water. The pH of the solution was adjusted to between 4.1 and 4.3 using HCl. Cells were covered in Alizarin Red solution for 1-2 minutes. Alizarin Red solution was removed and the wells washed with water until excess dye was removed. Calcium deposits (excluding oxalate) were stained orange-red by the Alizarin Red stain and visible under a microscope.

Von Kossa staining was performed, in some embodiments, by the following Von Kossa Protocol 1. The following solutions were prepared: 5% silver nitrate solution (5 g silver nitrate to 100 mL water), 5% sodium thiosulfate (Hypo) solution (5 g sodium thiosulfate to 100 mL water), 5% silver nitrate solution was added to each well designated for von Kossa until the well bottom was covered. The well plates were placed under a 15W incandescent bulb or the biosafety hood UV lamp to stain for 1 hour. The silver nitrate solution was removed and the wells were rinsed with water until residual silver nitrate solution was removed. A 5% Hypo solution was added to each of the wells for 5 minutes at room temperature. The wells were then rinsed with water until residual Hypo solution was removed. The Von Kossa stain appeared brown-black and was visible under a microscope.

Alternatively, Von Kossa staining was performed by Von Kossa Protocol 2. Fresh 2% silver nitrate solution was prepared (2 g silver nitrate to 100 mL water) and used within one week of preparation. A 2% silver nitrate solution was added to each well designated for von Kossa until the well bottom was covered. The well plates were covered in aluminum foil to incubate in a dark environment for 10 minutes. The aluminum foil was removed and the wells were rinsed twice with water. The well plates were left in fresh Millipore water and exposed to a 60 W incandescent light bulb for 15 minutes. Aluminum foil was placed beneath the well plate to help reflect light. The silver nitrate solution was removed and the wells were rinsed twice with water. Von Kossa stain appeared brown-black and was visible under a microscope.

Alkaline Phosphatase staining was performed, in some embodiments, by the following Alkaline Phosphatase Protocol 1. Alkaline dye mixture was prepared by adding the following solutions in order: 0.2 mL of FBB-alkaline solution was added to 0.2 sodium nitrite solution and mixed. The mixture was added to 9 mL of water. A 0.2 mL naphthol AS-BI alkaline solution was added to the mixture. The tube containing the dye mixture was wrapped in aluminum foil to protect from light. The prepared dye mixture was added to each well designated for ALP staining until the bottom was covered. The wells were incubated for 15 minutes at room temperature. After 15 minutes, the wells were rinsed with water until excess dye was removed. Where alkaline phosphatase was expressed, the ALP stain appeared as blue-purple patches visible under a microscope.

Alternatively, Alkaline Phosphatase staining was performed by Alkaline Phosphatase Protocol 2. Alkaline dye mixture was prepared by adding the following solutions in order: A0.2 mL of FRV-alkaline solution was added to 0.2 sodium nitrite solution and mixed. The mixture was allowed to sit for 2 minutes and then added to 9 mL of water. 0.2 mL naphthol AS-BI alkaline solution was added to the mixture. The tube containing the dye mixture was wrapped in aluminum foil to protect from light. The prepared dye mixture was added to each well designated for ALP staining until the bottom was covered. The well plates were covered with aluminum foil and incubated in the dark for 15 minutes at room temperature. After 15 minutes, the wells were rinsed with water until excess dye was removed. Where alkaline phosphatase was expressed, the ALP stain appeared as red-violet patches visible under a microscope.

Amnion Cell Monolayer Osteogenic Differentiation 1

Figure 6A:
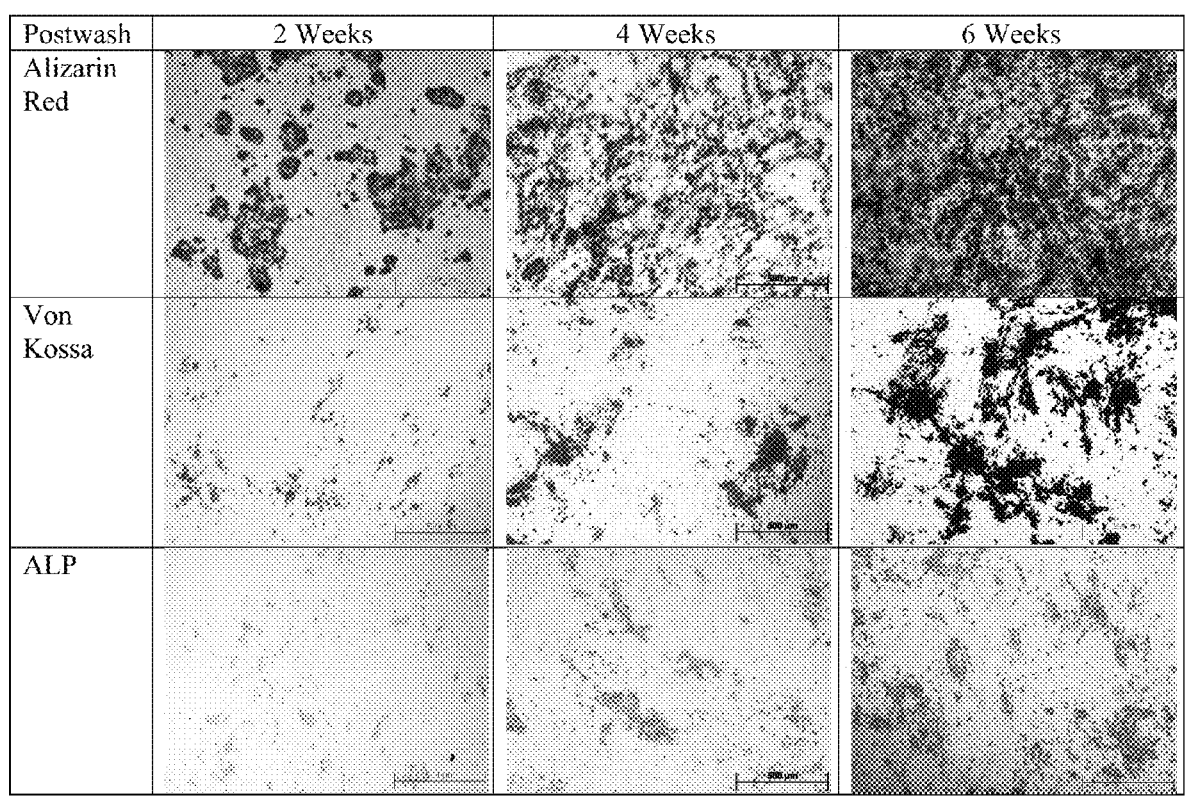
FIGS. 6A-6G illustrate osteogenic differentiation of isolated amnion cells in various configurations.

As illustrated in FIG. 6A, Alizarin Red and von Kossa staining increased from 2 weeks through 6 weeks. Alizarin Red stains calcium deposits red, while von Kossa stains calcium phosphate brown-black. The stains suggest increasing mineralization of the wells by calcium deposition over the course of the osteogenic differentiation study.

Amnion Cell Monolayer Osteogenic Differentiation 2

Figure 6B:
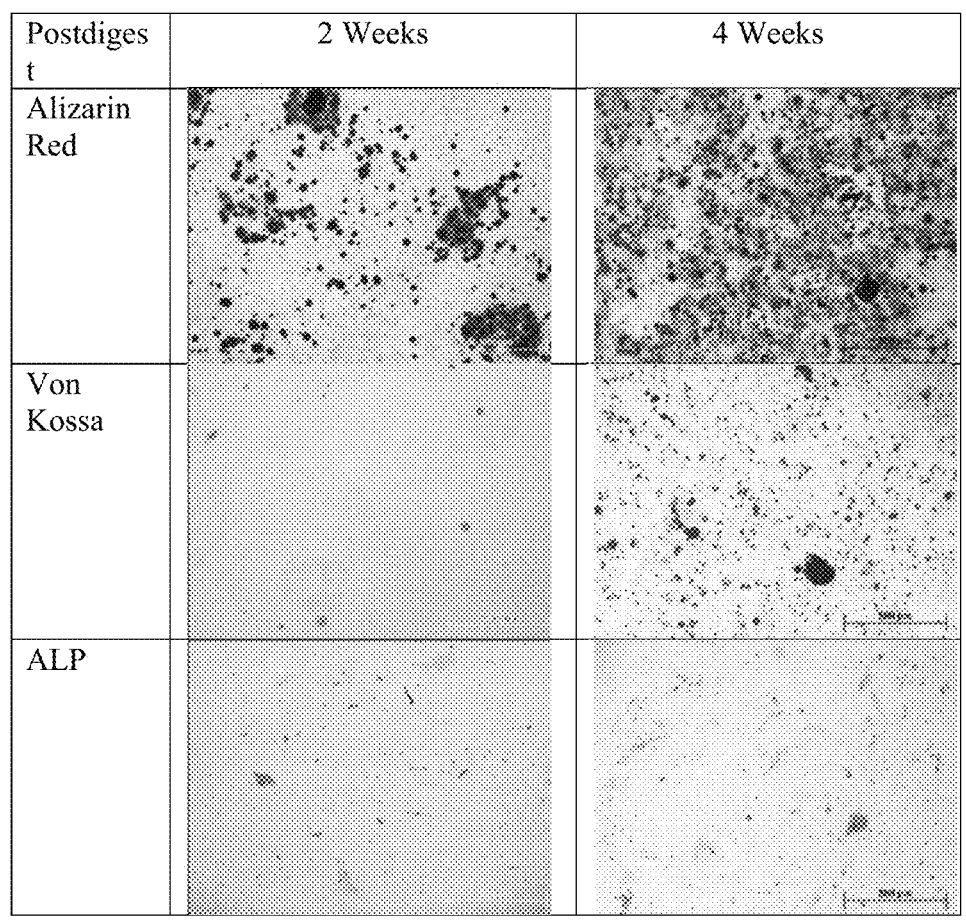

As illustrated in FIG. 6B, Alizarin Red and von Kossa staining increased from 2 weeks to 4 weeks, which suggest increasing mineralization of the wells by calcium deposition. Compared to the Osteogenic Differentiation 1 wells, the Osteogenic Differentiation 2 wells followed a similar trend of increased stain and had comparable Alizarin Red staining, but less Von Kossa staining at the same time points. The Alizarin Red and von Kossa stains were also more diffuse and evenly spread out rather than concentrated in patches as in the Osteogenic Differentiation 1 wells.

Amnion Cell Monolayer Osteogenic Differentiation 3

Figure 6C:
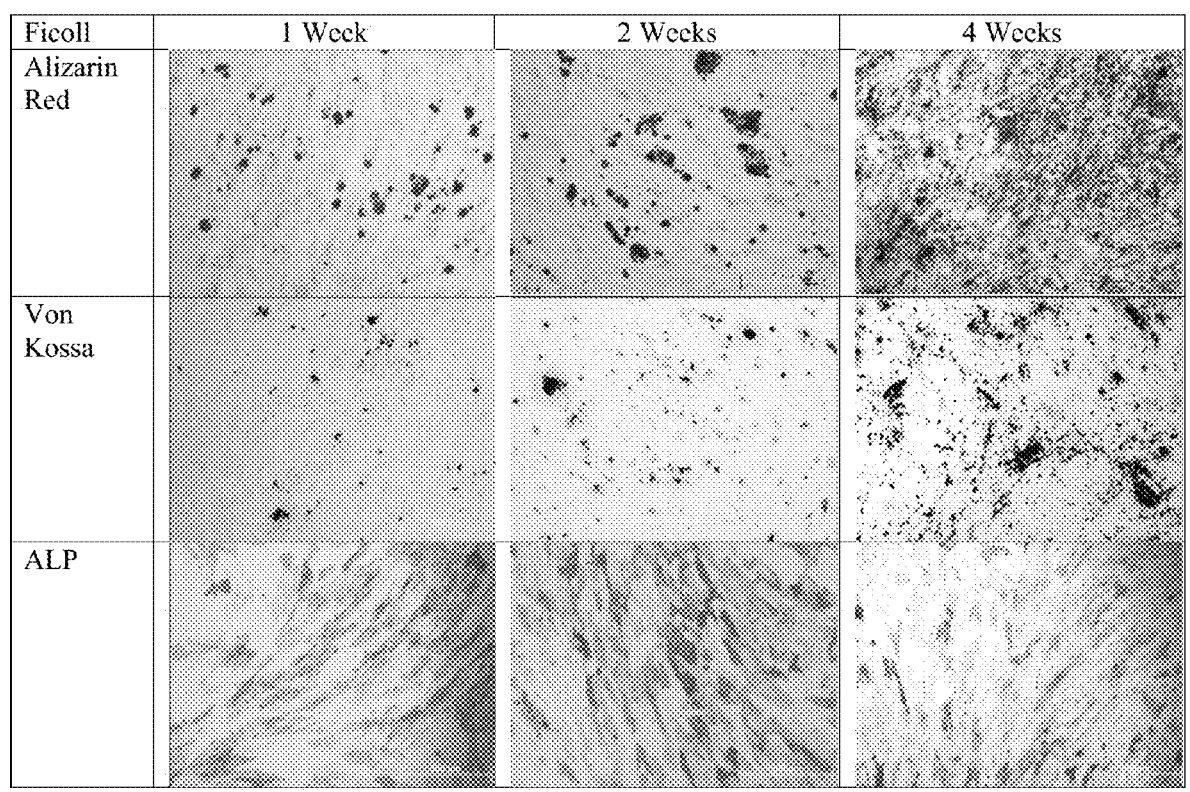

As illustrated by FIG. 6C, calcium deposits were evident by 9 days (1 week time point) in differentiation media. Both Alizarin Red and Von Kossa staining showed an increasing amount of red and black staining, respectively, from 1 week to 4 weeks. The 2 week Alizarin Red staining appeared to be comparable to Osteogenic Differentiation 2 wells, but the Von Kossa staining was stronger and more similar to the Osteogenic Differentiation 1 wells. However, by 4 weeks the Ficoll cells seemed to be more strongly stained with Alizarin Red and both Alizarin Red and Von Kossa stains are comparable to Osteogenic Differentiation 1 wells. The Alizarin Red and Von Kossa stains were more diffuse and spread out than Osteogenic Differentiation 1 wells at all time points, and their distribution is comparable to Osteogenic Differentiation 2 wells. The ALP staining was as expected, with high levels peaking at 9-14 days (week 1 and week 2) then decreasing over time afterwards as shown at the week 4 time point. Overall, this experiment demonstrated that isolating cells by tissue digestion and separation did not negatively impact their osteogenic differentiation capability, and that osteogenic differentiation may be evident as early as within 9 days.

Amnion Sheet Osteogenic Differentiation

Figure 6D:
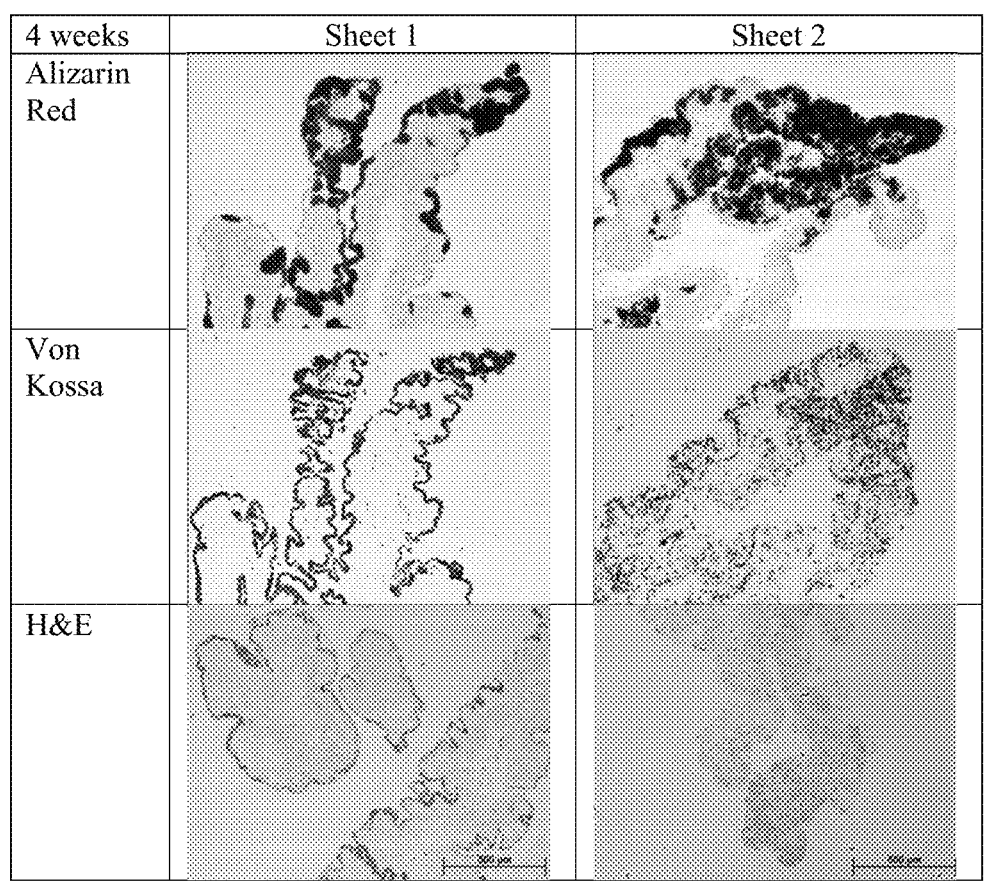

As illustrated in FIG. 6D, Sheet 1 appeared to have more Alizarin Red stain than Sheet 2 at 4 weeks and was strongly concentrated within one area, both along the surface and deep within the tissue bulk. The Von Kossa stain was more diffuse for Sheet 1, with staining both within the tissue and along the edges. The Von Kossa staining along the outer layer seemed to be stronger for Sheet 2 than for Sheet 1, with a more solid line of stained calcium phosphate along the outer edge. Overall, these findings indicate that cells within amnion sheet tissue retain osteogenic differentiation capability.

Amnion Sheet Osteogenic Differentiation

Figure 6E:
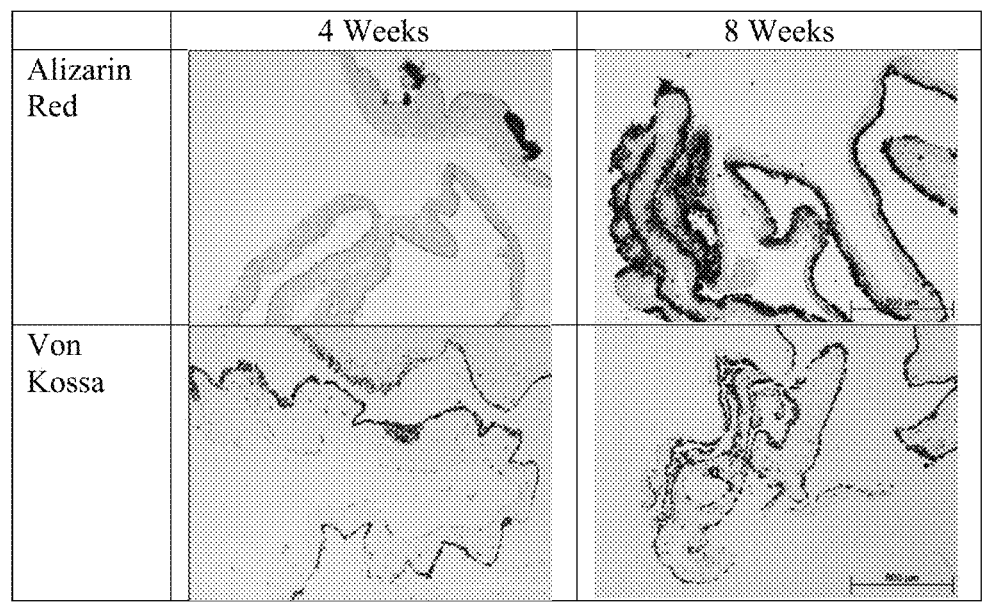

As shown in FIG. 6E, at 8 weeks, the amnion sheet had mineralized considerably compared to what was observed at 4 weeks. Positive Alizarin Red staining could be observed all along the tissue, with some areas of stronger staining where several tissue surfaces in close proximity were exposed. Von Kossa has also increased staining from 4 to 8 weeks, with some areas strongly positive at 8 weeks while other edges only have a thin line of Von Kossa staining.

Figure 6F:
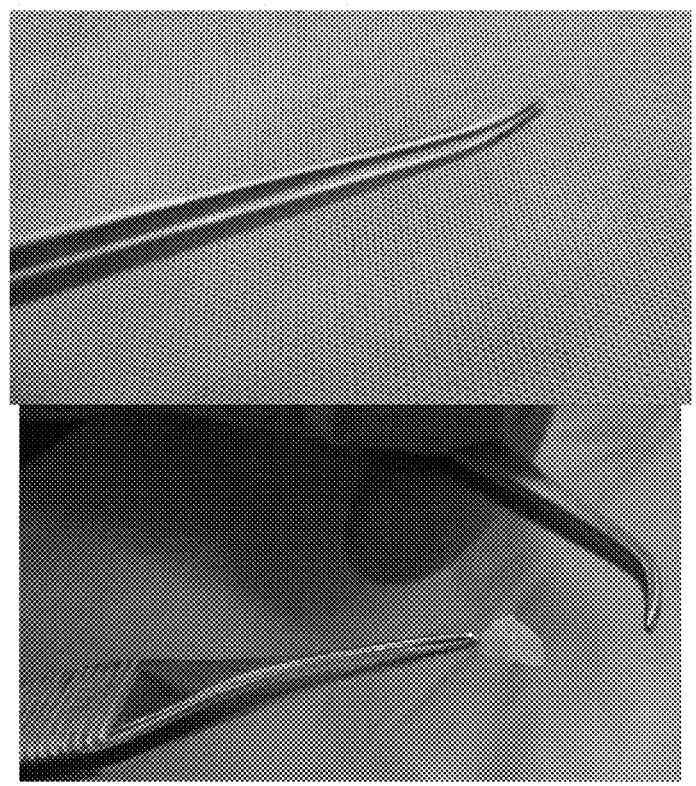

The 8 week sheet was cut in half during collection and only one half was sent for histology. The other half was kept for 16 weeks to observe the extent of mineralization after a very long period of time in osteogenic media. During sheet collection, it was noticed that the sheet appeared to be more rigid than normal amnion. Amnion pieces generally curl up and flop downward when picked up with forceps (FIG. 6F, top panel), yet this sheet could be kept relatively flat and was able to stay upright even when held with forceps horizontally (FIG. 6F, bottom panel).

Minced Amnion Osteogenic Differentiation

Figure 6G:
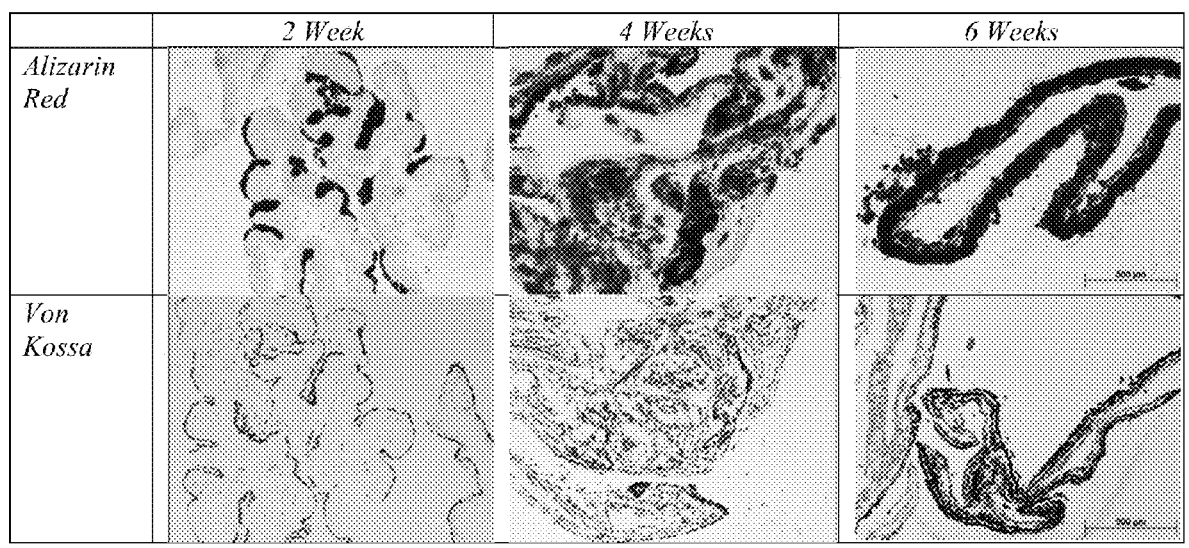

As illustrated in FIG. 6G, Alizarin Red and Von Kossa staining could be observed in the 2 week time points, showing that mineralization had begun within 2 weeks of osteogenic induction. At 4 weeks, both the Alizarin Red and the Von Kossa stains permeated throughout the tissue, staining the tissue positive both along the tissue edges as well as within the minced tissue itself. This was a significant change from 2 weeks where only the edges were positive. This distribution of positive staining was also similar to the positive staining of the amnion sheet at 4 weeks. At 6 weeks, nearly the entirety of the visible tissue was positive for Alizarin Red and Von Kossa.

The minced tissue also behaved like the sheet after several weeks in osteogenic media. The tissue did not droop when held horizontally, and when forceps were used to push the tissue downward, the minced tissue returned to the horizontal position after the forceps were removed.

In conclusion, the example demonstrated that amnion-derived cells (from explants or tissue digestion) are capable of osteogenic differentiation in as little as 9 days and could mineralize considerably, as shown by the significant amount of Alizarin Red visible (which stains for calcium) and was supported by Von Kossa and Alkaline Phosphatase staining.

The study also showed that the amnion tissue itself may become mineralized in a variety of configurations (minced, sheet remains of explants, minced remains of explants) with varying degrees and rates of osteogenic differentiation. An interesting observation was the increased rigidity of tissue after culture in osteogenic media. Both sheet and minced tissue were able to retain their shape and position even after manipulation with forceps. Overall, it can be concluded that amnion cells do have potential for osteogenic differentiation.

Example 6—Histology of Osteogenic Differentiation of Amnion Tissue

In this example, histology of osteogenic differentiation of amnion tissue sheets were cut into two portions and were compared at 8 week and 16 week (4 month) time points. Amnion sheet osteogenic differentiation was performed per procedures of Example 5.

Figure 7A:
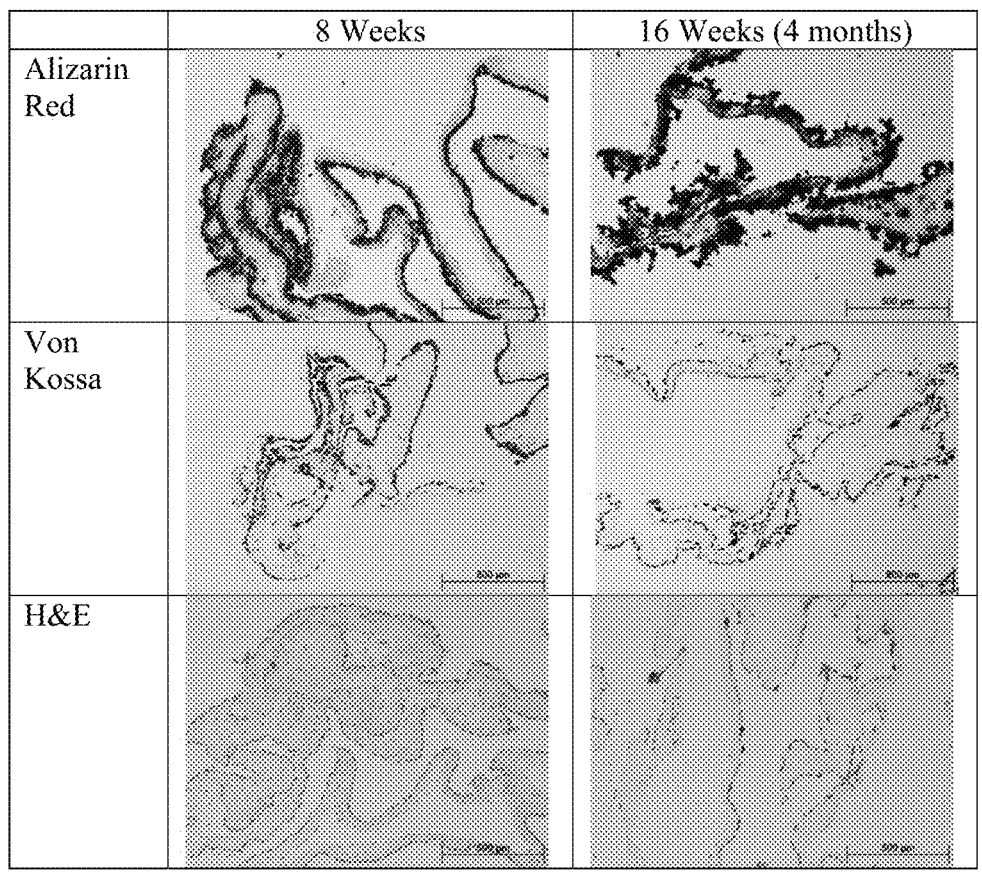
FIGS. 7A-7B illustrate osteogenic differentiation of amnion in a sheet configuration.

As illustrated in FIG. 7A, at 8 weeks, the amnion sheet had positive Alizarin Red staining all along the tissue in the epithelial layer, with some areas of stronger staining where several tissue surfaces in close proximity were exposed due to tissue folding. Von Kossa also showed positive staining along the epithelial layer.

Figure 7B:
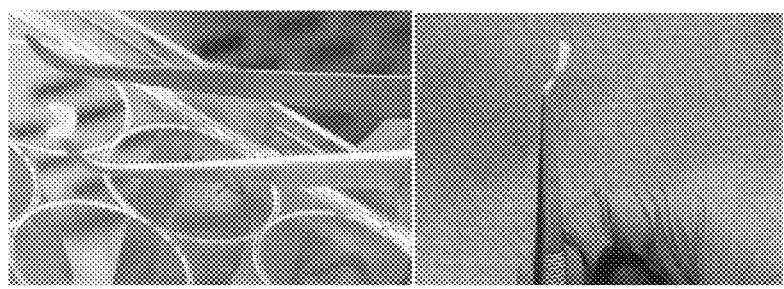

The other half of the sheet was kept in osteogenic media until the 16 week time point. During sheet collection, it was noticed that the sheet appeared to be more rigid than normal amnion. The amnion sheet could be slightly molded and kept a curved shape when bent with forceps, as illustrated in FIG. 7B, left panel. The sheet was also able to stay vertical when held with forceps without any drooping, as illustrated in FIG. 7B, right panel.

The Alizarin Red staining was very strongly positive all throughout the tissue with particularly red areas both in the epithelial surface as well as within the tissue. The stain appeared to be stronger in the 16 week time point, with larger areas of red as well as darker red stains. The Von Kossa stain was also evident at 16 weeks along the epithelial surface of the amnion sheet.

Example 7—Adipogenic and Osteogenic Differentiation Potential of Amnion Tissue

In this example amnion tissue was utilized to investigate the adipogenic and osteogenic differentiation potential. The experiment was conducted according to the following procedures.

First, 8 mm biopsy punches of amnion tissue from a donor were plated into 15 wells each of 3 TC-treated 48 well plates for 5 time points. One well plate was designated as the control plate, osteogenic plate, and adipogenic plate. The experimental end points were 2, 4, 6, 8, 16 weeks. Osteogenic plates were fed with complete osteogenic media with β-glycerophosphate, adipogenic plates were fed with complete adipogenic media, and control plates were fed with complete growth media, replaced every 3-4 days. At each time point, three biopsy tissue samples from the control, osteogenic, and adipogenic well plates were placed into 10% neutral buffered formalin for 1 day. After 1 day, each punch was transferred into 70% ethanol for storage until sent to a histology lab for staining.

DMEM/F12 complete growth media was generated by the following procedure. EGF and bFGF were reconstituted per manufacturer's instructions and stored in the −20° C. freezer. DMEM/F12 basal media was supplemented with 1% PenStrep, 1% Glutamax, and 10% HI-FBS final v/v, then sterile filtered and stored refrigerated in the dark. Complete growth media was made by adding 0.1% EGF and 0.1% bFGF v/v to supplement DEMEM/F12 immediately before use.

Complete adipogenic media was generated by the following procedure. One bottle of adipogenic supplement was combined with one bottle of adipogenic basal medium. A volume of 1% PenStrep was added to the combined components to make complete adipogenic media.

Complete osteogenic media was generated by the following procedure. Osteogenic Stimulatory Supplements, β-glycerophosphate, dexamethasone, and ascorbic acid were aliquotted and stored per manufacturer's instructions. The following components were added to 42.5 mL of Mesenult MSC Basal Medium: 7.5 mL osteogenic stimulatory supplements, dexamethasone, 2504, ascorbic acid, 1754, β-glycerophosphate, a volume of 1% PenStrep final v/v was added to the supplemented Osteogenic Media. The complete Osteogenic Media was stored refrigerated in the dark.

Figure 8A:
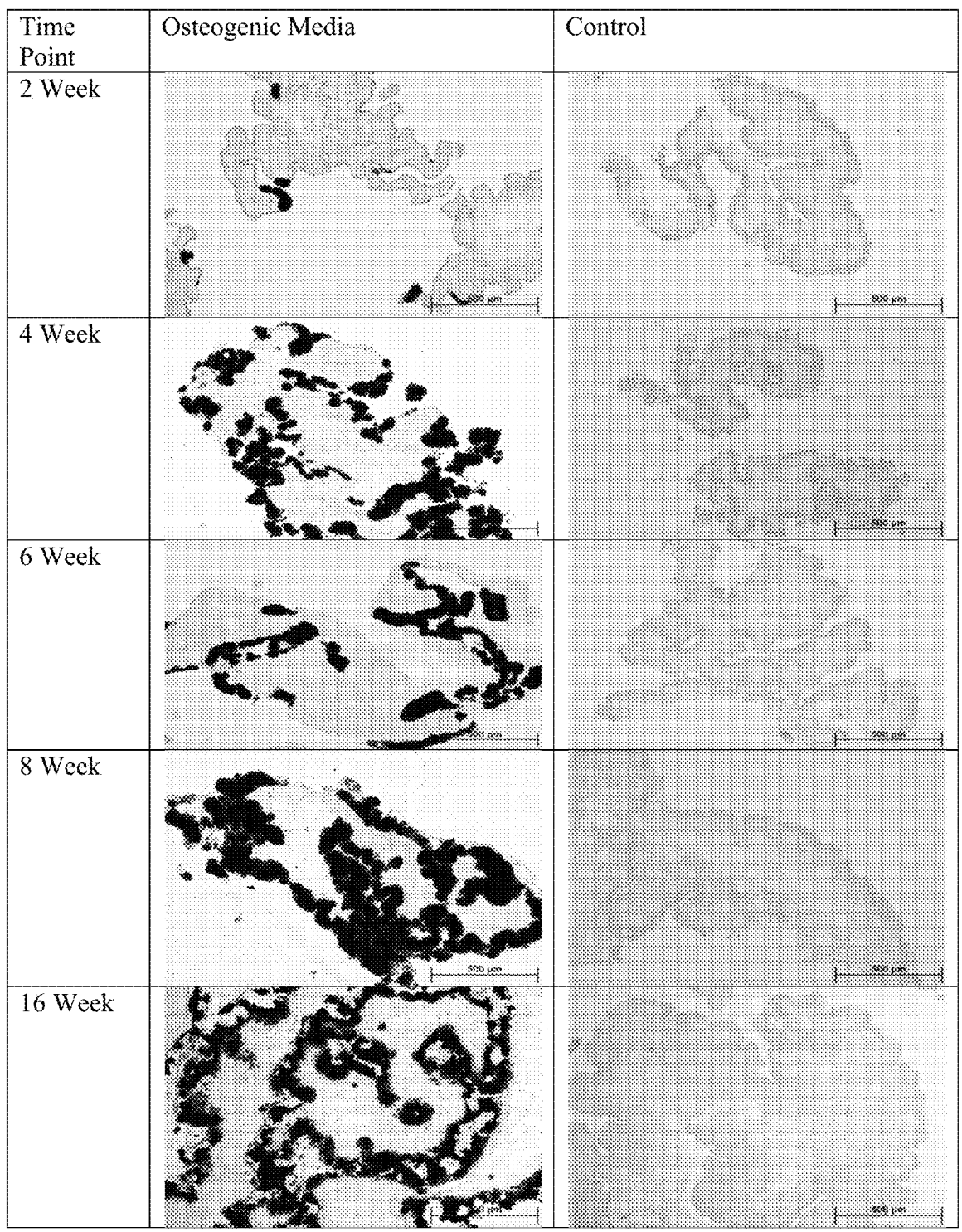
FIGS. 8A-8E illustrate osteogenic and adipogenic differentiation of amnion tissue.

As illustrated in FIG. 8A, control amnion tissue samples cultured in growth media did not have any positive Alizarin Red staining throughout the 5 time points. By 2 weeks, some Alizarin Red staining could be observed in the tissue samples cultured in osteogenic media at the epithelial surface layer. At week 4 and week 6, the amount of Alizarin Red had increased, and the sizes of the stained nodules were also larger. Significant amounts of positive Alizarin Red staining could be observed at week 8, with some nodules reaching deep into the amnion mesenchymal layers from the epithelial surface layer. This is indicative of mineralization not only at the surface by amnion epithelial cells, but also in the mesenchymal cell layers of the tissue. By week 16, there was a thick, continuous layer of Alizarin Red staining along the epithelial surface layer that reached into the tissue.

Figure 8B:
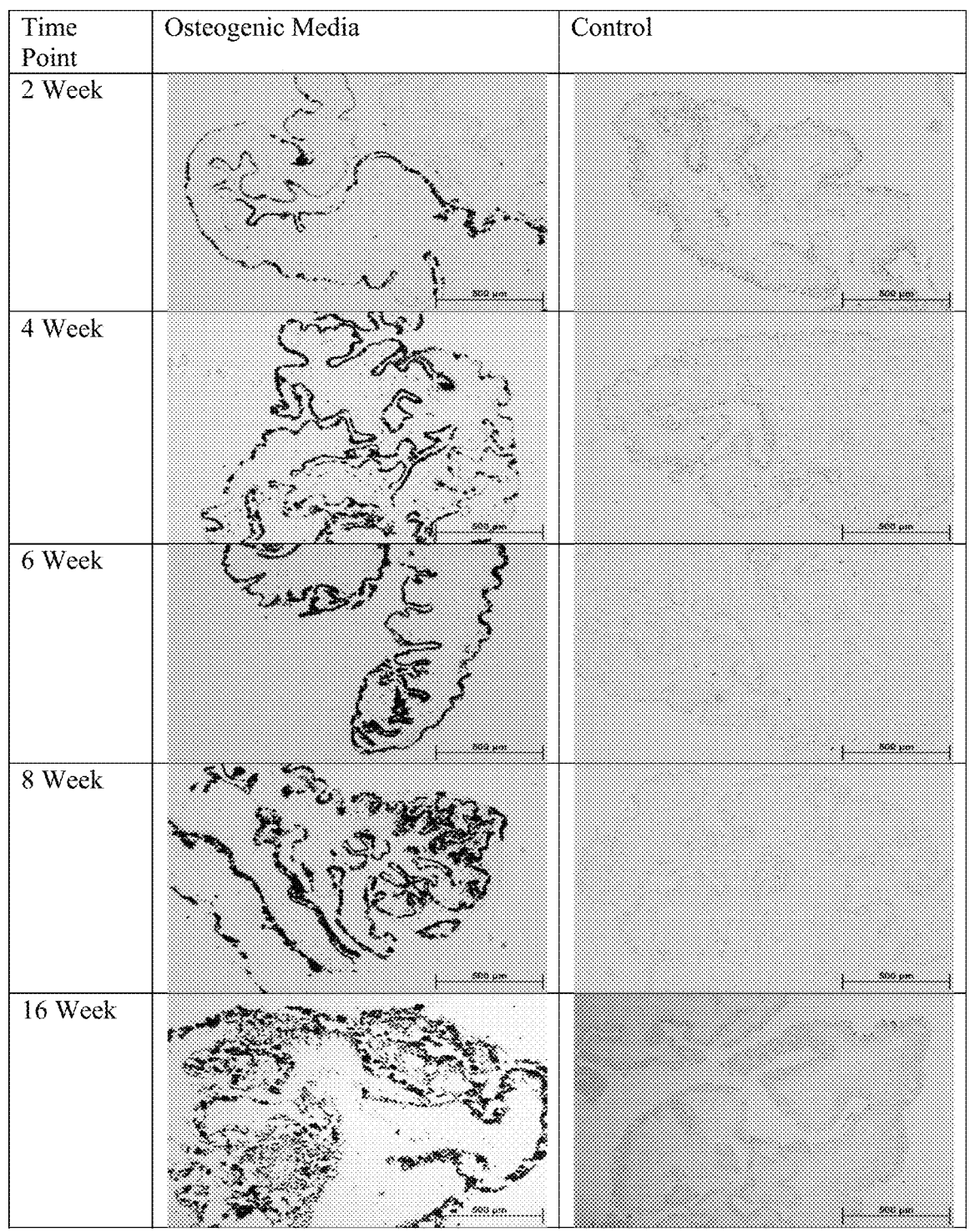

FIG. 8B illustrates Von Kossa staining of tissue samples cultured in osteogenic media vs. tissue in growth media. Images were obtained at 10× magnification. Similar trends were observed in the tissue samples cultured in osteogenic media and stained with Von Kossa. By week 2, some Von Kossa staining was visible along the epithelial surface layer of the amnion tissue. Weeks 4 and 6 demonstrated an increase in the thickness of the stain in the tissue, and the Von Kossa stain was more continuous along the epithelial layer. Week 8 Von Kossa staining showed penetration of the stain into the deeper layers of the amnion, suggesting that the mesenchymal layers had also mineralized to some extent. At week 16, there were regions of the tissue that contained numerous scattered Von Kossa stain, which may be a sign of larger mineralized nodules. Von Kossa staining was not observed at any of the time points for control tissue samples.

Figure 8C:
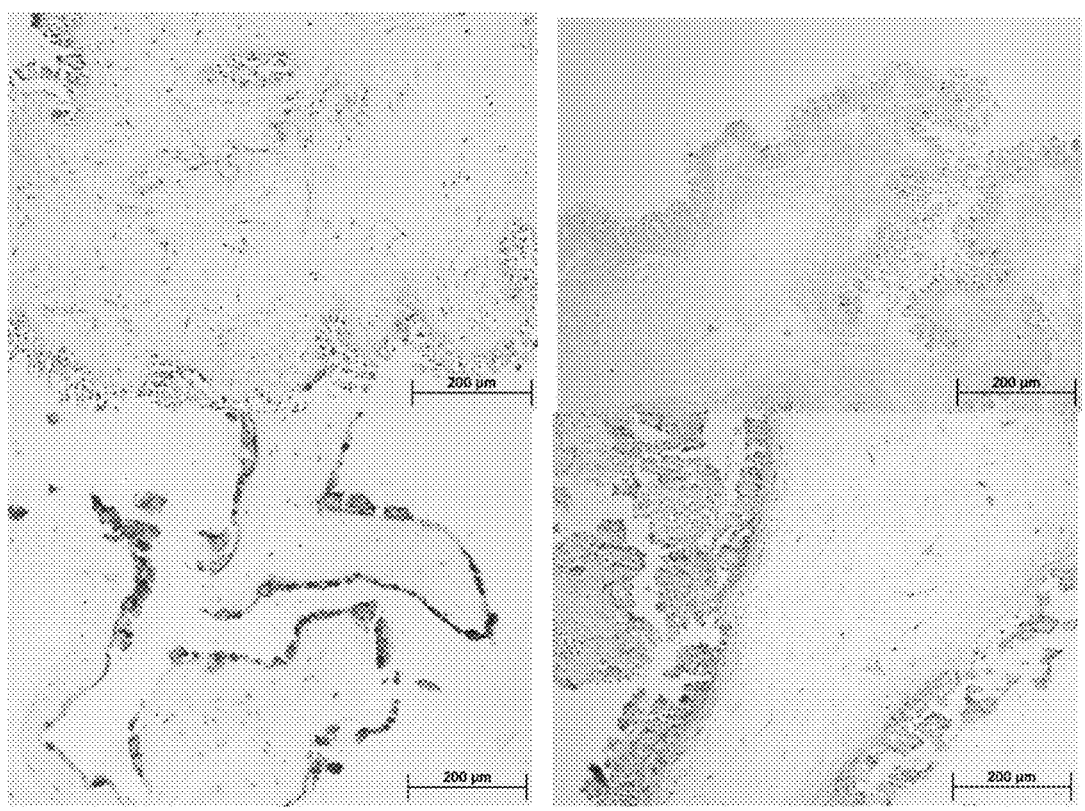

H&E staining was also performed on the test and control tissue samples. By week 6, the control tissue still had many cells along the epithelial surface layer, as well as mesenchymal cells deeper within the tissue (FIG. 8C, top left panel). By week 16, nearly all the cells in the mesenchymal layers were gone and only some stained nuclei were visible in the epithelial layer (FIG. 8C, top right panel). The later samples of osteogenic tissue contain nodules of H&E stain in the epithelial layer that obfuscate any nuclei stained in those regions (FIG. 8C, bottom left panel). However, a number of mesenchymal cells can be seen in the tissue. By week 16, the nodules were even larger so it was still not possible to discern epithelial cells in the osteogenic tissue through H&E staining, but it was noted that there were similar numbers of mesenchymal cells (FIG. 8C, bottom right panel) as compared to the osteogenic tissue at week 6. Looking at only the mesenchymal cells, the loss of mesenchymal cells over time in the control tissue but not in osteogenic tissue was anticipated, as the cells were in osteogenic differentiation media and thus not expected to be as proliferative or motile as they would be in growth media.

Figure 8D:
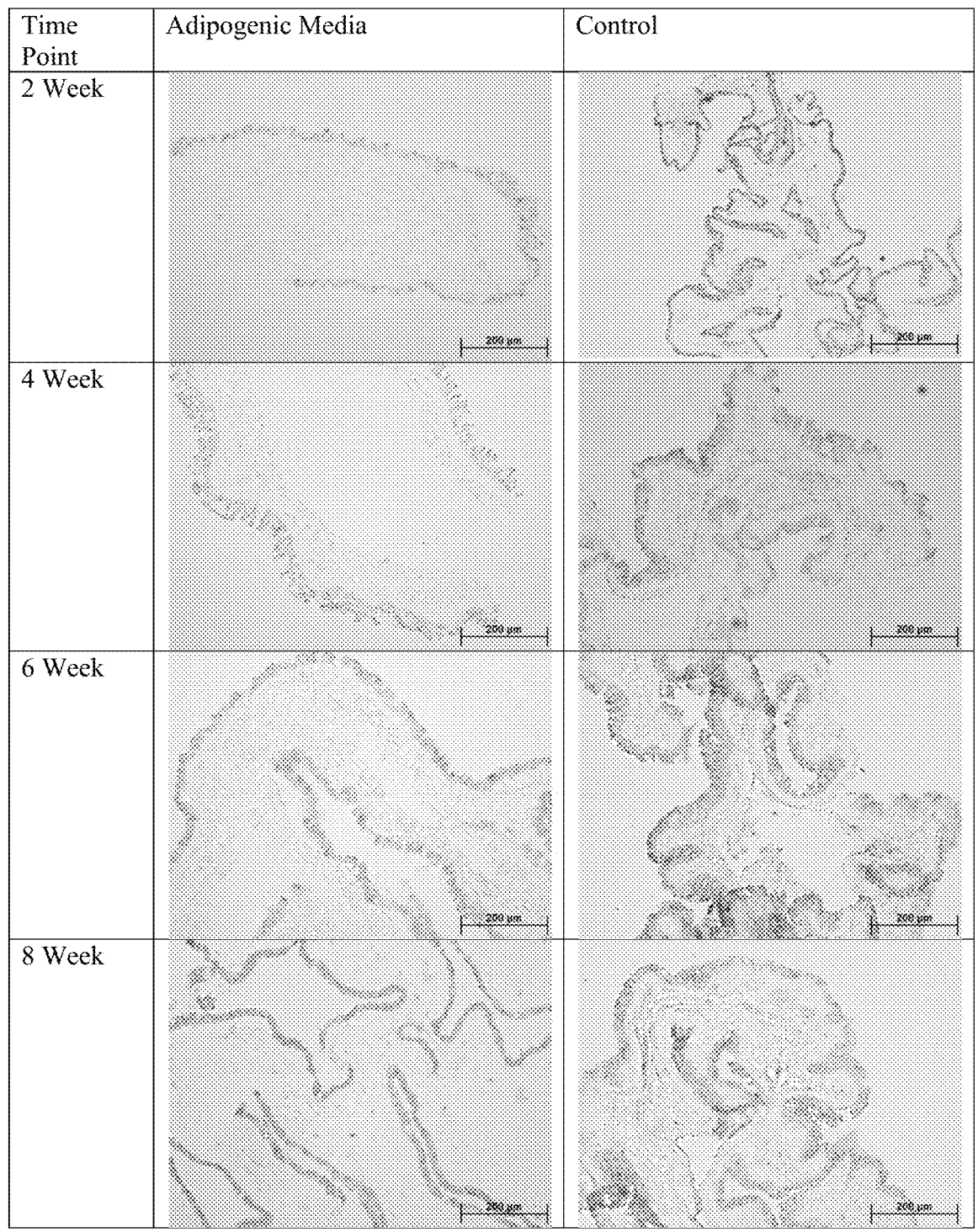
Figure 8E:
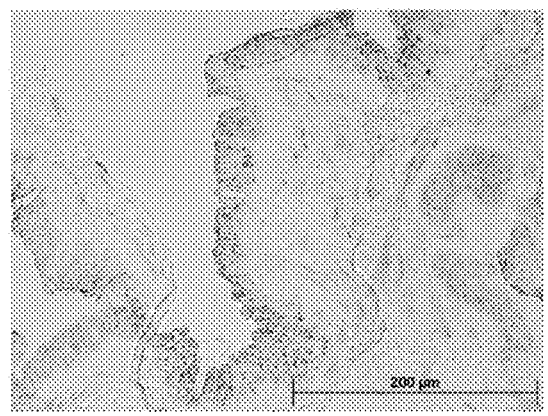

FIG. 8D illustrates Oil Red O staining of the tissue samples cultured in adipogenic media vs. tissue in growth media. The images were obtained at 20× magnification. As illustrated in FIG. 8D, Oil Red O staining was also positive at week 2 on onward for adipogenic test tissue samples, although the corresponding control tissue had comparable staining. From week 2 to week 8, there was a slight increase in intensity of the Oil Red 0 staining in adipogenic tissue samples, but the Oil Red O was always only at the epithelial surface layer for all tissue samples. FIG. 8E illustrates a 40× magnification image of control tissue stained with Oil Red O at week 4. Individual stained droplets can be distinguished in the epithelial layer of the amnion.

In conclusion, fresh amnion tissue samples cultured in osteogenic or adipogenic media for up to 16 weeks were compared to tissue samples cultured in control growth media. Positive staining for Alizarin Red and Von Kossa indicative of osteogenic differentiation appeared at the first time point, week 2, for osteogenic test tissue samples and progressively increased in intensity and prevalence both at the epithelial cell layer at the surface of the tissue as well as at the mesenchymal cell layers within the tissue until week 16. During that time, it was also noted that the number of mesenchymal cells within the osteogenic tissue samples did not decrease significantly over time, but that there was a noticeable decrease in epithelial and mesenchymal cells over time in the control tissue samples.

Example 8—Osteogenic Differentiation Potential of Amnion Tissue after 6 Weeks of Hypothermic Storage In this example, the osteogenic differentiation potential of amnion tissue sheets was investigated following 6 weeks of hypothermic storage. The experiment was conducted according to the following procedures.

Tissue differentiation and staining was performed by the following procedure. Amnion tissue from one placental donor was separated, washed, and cut into 2×2 cm sheets. Sheets were packaged in groups of 4 into a separate Kapak per time point with supplemented DMEM/F12 (lacking growth factors) and stored hypothermically (e.g., in the 4° C. refrigerator). At the 6 week time point, one set of 4 samples set aside for cell culture was retrieved from storage and cut into approximately 1×2 cm sized pieces using a scalpel. The amnion tissue was designated as osteogenic (2 sample pieces) or control (1 sample piece) and each piece was placed into a separate well of a 24 well plate. A volume of 1 mL of complete osteogenic or DMEM/F12 growth media was added to each of the corresponding wells. The media in the wells was changed with the appropriate fresh complete media twice a week. After 4 weeks, all five tissue pieces were collected, placed into separate vials of formalin, and fixed overnight. After fixation, the samples were placed into separate vials with 75% ethanol for storage. The amnion samples were analyzed for Alizarin Red (osteogenic), von Kossa (osteogenic), and hematoxylin and eosin (H&E) staining (all samples). The control sample was sectioned multiple times and stained to serve as negative control to both the osteogenic and the chondrogenic tissue samples. The slides were analyzed for positive staining indicative of mineralization (Alizarin Red and von Kossa, osteogenic).

Figure 9A:
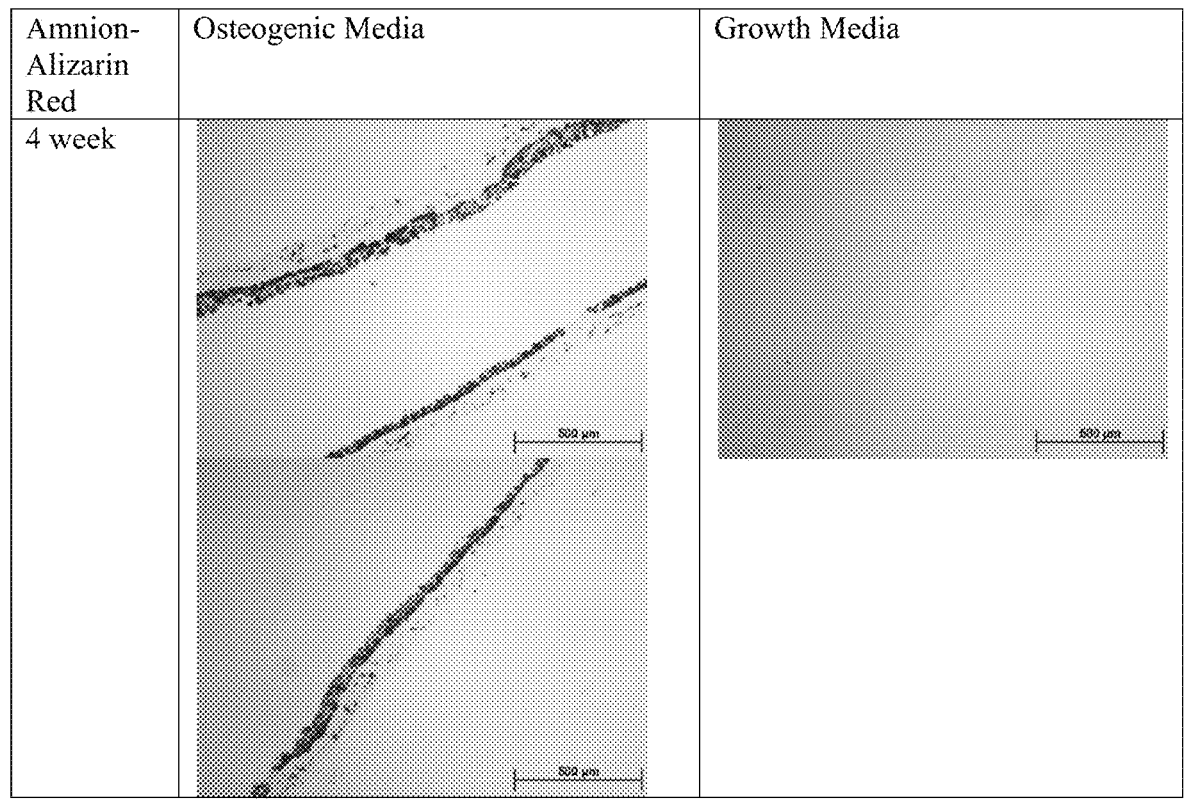
FIGS. 9A-9C illustrate osteogenic differentiation of amnion tissue.
Figure 9B:
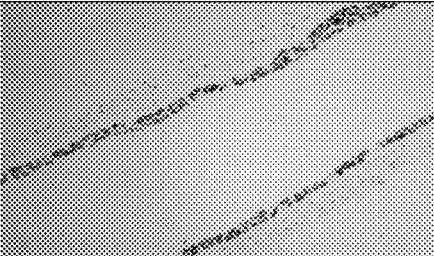
Figure 9B:
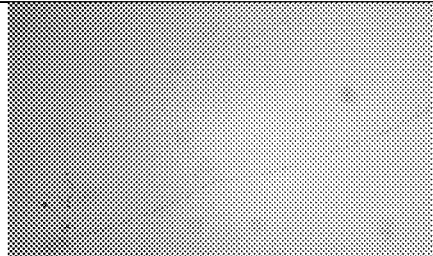
Figure 9C:
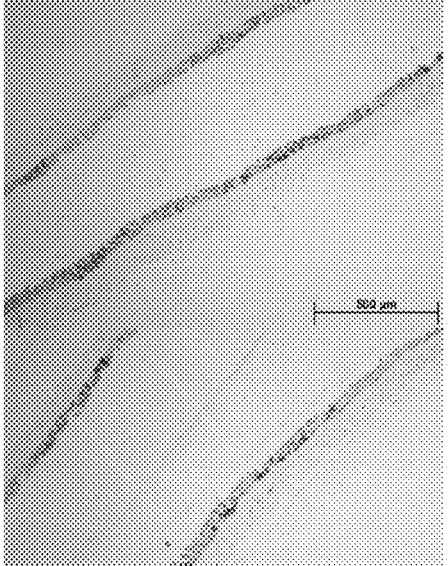
Figure 9C:
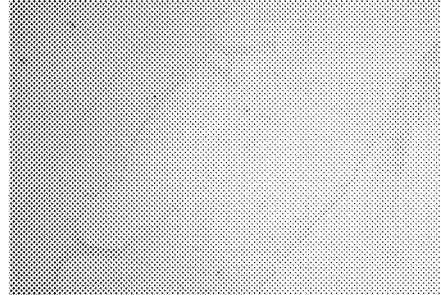

FIG. 9A illustrates Alizarin Red staining, FIG. 9B illustrates Von Kossa staining, and FIG. 9C illustrates H&E staining of hypothermically stored amnion tissue in osteogenic or control culture conditions. The images were obtained at 10× magnification. By 4 weeks, positive Alizarin Red and Von Kossa staining were visible in the amnion tissue. Both Alizarin Red and Von Kossa stains were mostly constrained to the epithelial layer, with some fibroblast layer Alizarin Red staining. This was also reflected in the H&E stain for these tissue samples, showing dark mineralized nodules along the epithelial layer. These results indicated that the tissue was still functionally capable of osteogenic differentiation within 4 weeks even after 6 weeks of refrigerated storage.

In addition, the mineralization of the osteogenic tissue samples is corroborated by the nodules in the corresponding H&E stains. By demonstrating osteogenic differentiation over time, this experiment reveals that it may be possible to store amnion tissue at refrigerated temperatures for weeks and retain functionality, without the extra effort needed to cryopreserve the tissue.

In conclusion, the amnion tissue samples stored at refrigerated temperature for 6 weeks without media exchanges were tested for osteogenic differentiation potential. The control tissue did not stain at all, indicating lack of cells or structure for unknown reasons. However, compared to previous stains and images from journal articles, the Alizarin Red and von Kossa appear to be positive. This suggests that the tissue was functional and underwent osteogenic differentiation even after refrigerated storage for 6 weeks. These results demonstrate the potential for a functional amnion tissue form that can be stored as refrigerated tissue as opposed to cryopreserved tissue.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Also, the phraseology and terminology used herein is for the purpose of description and should not be regarded as limiting.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for the use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. "Consisting essentially of" means inclusion of the items listed thereafter and which is open to unlisted items that do not materially affect the basic and novel properties of the invention.

INCORPORATION BY REFERENCE

All publications, patents and sequence database entries mentioned herein are hereby incorporated by reference in their entireties as if each individual publication or patent was specifically and individually indicated to be incorporated by reference.

We claim:

1. An artificially primed tissue graft, comprising:
a tissue obtained from a donor; and
viable cells that are endogenous to the tissue and remain resident in the tissue, wherein the viable cells have been primed with one or more stimuli comprising simulated hypoxia to produce the artificially primed tissue graft, wherein when used to treat a patient the artificially primed tissue graft provides a benefit compared to non-primed tissue, said benefit comprising an increased amount of angiogenic growth factors in the artificially primed tissue graft, wherein the angiogenic growth factors comprise epidermal growth factor (EGF), hepatocyte growth factor (HGF), and placental growth factor (PGF).

2. The artificially primed tissue graft of claim 1, wherein the simulated hypoxia was induced by exposing the tissue and resident endogenous viable cells to a medium ingredient that simulates hypoxia, or both.

3. The artificially primed tissue graft of claim 1, wherein the medium ingredient comprises deferoxamine.

4. The artificially primed tissue graft of claim 1, wherein exposure to simulated hypoxia occurred for a period of time from about 5 hour to about 100 hours.

5. The artificially primed tissue graft of claim 4, wherein said period of time is from about 20 hours to about 100 hours.

6. The artificially primed tissue graft of claim 4, wherein said period of time is from about 20 hours to about 30 hours.

7. The artificially primed tissue graft of claim 1, wherein the tissue obtained from a donor comprises placental tissue.

8. The artificially primed tissue graft of claim 7, wherein the placental tissue comprises amnion tissue.

* * * * *